(12) United States Patent
Shi et al.

(10) Patent No.: US 8,183,050 B2
(45) Date of Patent: May 22, 2012

(54) DETECTION OF LYSOPHOSPHATIDYLCHOLINE FOR PROGNOSIS OR DIAGNOSIS OF A SYSTEMIC INFLAMMATORY CONDITION

(75) Inventors: Song Shi, Reisterssrown, MD (US);
Thomas Gentle, St. Michael, MN (US);
Richard Moore, Glenville, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 515 days.

(21) Appl. No.: 11/541,412

(22) Filed: Sep. 28, 2006

(65) Prior Publication Data

US 2007/0111316 A1 May 17, 2007

Related U.S. Application Data

(60) Provisional application No. 60/721,833, filed on Sep. 28, 2005, provisional application No. 60/762,911, filed on Jan. 26, 2006, provisional application No. 60/841,407, filed on Aug. 30, 2006.

(51) Int. Cl.
*G01N 1/00* (2006.01)
*G01N 33/00* (2006.01)

(52) U.S. Cl. ............... 436/86; 436/71; 436/85; 436/87; 436/171; 424/78.05

(58) Field of Classification Search .............. 436/171, 436/86
See application file for complete search history.

(56) References Cited

U.S. PATENT DOCUMENTS

| | | | |
|---|---|---|---|
| 6,190,872 B1 | 2/2001 | Slotman | |
| 6,248,553 B1 * | 6/2001 | Small et al. | ...... 435/25 |
| 2003/0228648 A1 | 12/2003 | Laskin et al. | |
| 2007/0021465 A1 | 1/2007 | Al-Abed et al. | |
| 2011/0118569 A1 | 5/2011 | Shi et al. | |

FOREIGN PATENT DOCUMENTS

| | | |
|---|---|---|
| EP | 1 940 231 B1 | 5/2011 |
| JP | 09033525 A | 2/1997 |
| WO | WO 2007/038758 A2 | 4/2007 |
| WO | WO2009/123737 A2 | 10/2009 |

OTHER PUBLICATIONS

"Phosphatidylcholine and Related Lipids: Structure, Occurrence, Biochemistry and Analysis", Published online by W.W. Christie, Scottish Crop Research Institute(and Mylnefield Lipid Analysis), Invergowrie, Dundee(DD25DA), Scotland (Apr. 3, 2005).*
Das, "Can Sepsis and Other Critical Illnesses be Predicted and Prognosticated?", Advances in Sepsis, 5(2):52-59 (2006).
Drobnik et al., "Plasma Ceramide and Lysophosphatidylcholine Inversely Correlate with Mortality in Sepsis Patients", Journal of Lipid Research, 44:754-761 (2003).
Mehta, "Lysophosphatidylcholine: An Enigmatic Lysolipid", Am. J. Physiol. Lung Cell. Mol. Physiol., 289:L174-L175 (2005).
Wang et al., "Lipid Unites Disparate Syndromes of Sepsis", Nature Medicine, 10(2):124-125 (Feb. 2004).

(Continued)

*Primary Examiner* — Krishnan S Menon
*Assistant Examiner* — Rebecca M Fritchman
(74) *Attorney, Agent, or Firm* — Jones Day

(57) ABSTRACT

The present invention provides methods and compositions useful for the diagnosis or prognosis of a systemic inflammatory condition such as sepsis.

96 Claims, 23 Drawing Sheets

OTHER PUBLICATIONS

Yan et al., "Therapeutic Effects of Lysophosphatidylcholine in Experimental Sepsis", Nature Medicine, 10(2):161-167 (Feb. 2004).
"Phosphatidylcholine and Related Lipids: Structure, Occurrence, Biochemistry and Analysis", Published online by W.W. Christie, Scottish Crop Research Institute (and Mylnefield Lipid Analysis), Invergowrie, Dundee (DD2 5DA), Scotland (Feb. 6, 2006).
EPO Extended European Search Report dated Dec. 3, 2008, in European Patent Application No. 06825270.9, tiled Sep. 27, 2006.
Brunkhorst et al., 2002, "Aktuelle Aspekte Zur Sepsisdiagnose//Diagnostic Approach to Sepsis—State of Art." Zentralblatt Fuer Chirurgie, Barth, Leipzig, DE, vol. 127(3):165-173.
Das, Undurti N., 2004, "Role of Lipids in Sepsis," Crit. Care & Shock, Indonesian Society of Critical Care Medicine, ID, vol. 7(2):87-92.
Jackson et al., 2004, "Lysophospholipid Acyltransferases in Monocyte Inflammatory Responses and Sepsis," Immunobiology, Urban andFischer Verlag, DC, vol. 209(1-2):31-38.
Takala et al., 2002, "Markers of Inflammation in Sepsis," Annals of Medicine, Finnish Medical Society Duodecim, Helsinki, FI, vol. 34(7-08):614-623.
EPO Communication pursuant to Article 94(3) EPC dated Apr. 6, 2009, in European Application No. 06 825 270.9, filed Sep. 27, 2006.
Annex to Form PCT/ISA/206 "Communication Relating to the Results of the Partial International Search" dated Jul. 10, 2009, in International Application No. PCT/US2009/002065, filed Apr. 2, 2009.
Lissauer et al., 2007, "Decreased Lysophosphatidylcholine Levels are Associated with Sepsis Compared to Uninfected Inflammation Prior to Onset of Sepsis," *J. Surgical Res.* 137(2):206.
Abstract XP00253397 of Lissauer et al. (Lissauer et al., 2007, "Decreased Lysophosphatidylcholine Levels are Associated with Sepsis Compared to Uninfected Inflammation Prior to Onset of Sepsis," *J. Surgical Res.* 137(2):206).
Tang et al., 2007, "Accuracy of Procalcitonin for Sepsis Diagnosis in Critically Ill Patients: Systematic Review and Meta-Analysis," *Lancet Infectious Diseases* 7(3):210-217.
EPO Communication pursuant to Article 94(3) EPC dated Jun. 6, 2010, in European Application No. 06 825 270.9, filed Sep. 27, 2006.
International Search Report dated Nov. 4, 2009, for International Application No. PCT/US2009/002065, filed Apr. 2, 2009.
Written Opinion dated Nov. 4, 2009, for international Application No. PCT/US2009/002065, filed Apr. 2, 2009.
Bone et al., 1992, "American College of Chest Physicians/Society of Critical Care Medicine Consensus Conference: Definitions for Sepsis and Organ Failure and Guidelines for the Use of Innovative Therapies in Sepsis," *Crit. Care Med.* 20 (6): 864-74.
Jacoby et al., 2001, "Platelet Activation and Function after Trauma," *J. Trauma* 51(4): 639-47.
Desborough et al., 2000, "The Stress Response to Trauma and Surgery," *Br. J. Anaesth.* 85: 109-17.
International Search Report dated Jul. 25, 2007, for International Application No. PCT/US2006/038177, filed Sep. 27, 2006.
Written Opinion dated Apr. 1, 2008, for International Application No. PCT/US2006/038177, filed Sep. 27, 2006.
Response to the Communication pursuant to Article 94(3) EPC, filed Aug. 10, 2009, in European Application No. 06 825 270.9.
Levy et al., 2003, "2001 SCCM/ESICM/ACCP/ATS/SIS International Sepsis Definitions Conference," *Intensive Care Med.* 29(4):530-538.

\* cited by examiner

DETECTION OF LYSOPHOSPHATIDYLCHOLINE FOR PROGNOSIS OR DIAGNOSIS OF A SYSTEMIC INFLAMMATORY CONDITION

The instant Application claims benefit under 35 U.S.C. 119 of U.S. Provisional Applications Nos. 60/721,833, filed Sep. 28, 2005, 60/762,911, filed Jan. 26, 2006, and 60/841,407, filed Aug. 30, 2006, the contents of which are hereby incorporated by reference in their entireties.

1. FIELD OF THE INVENTION

The present invention relates to methods and compositions useful, for example, for diagnosis or prognosis of a systemic inflammatory condition in a subject. The systemic inflammatory condition can be, for example, systemic inflammatory response syndrome, sepsis, severe sepsis, septic shock, multiple organ dysfunction or mortality.

2. BACKGROUND OF THE INVENTION

Early detection of a disease condition typically allows for a more effective therapeutic treatment with a correspondingly more favorable clinical outcome. In many cases, however, early detection of disease symptoms is problematic due to the complexity of the disease; hence, a disease may become relatively advanced before diagnosis is possible. Systemic inflammatory conditions represent one such class of diseases. These conditions, particularly sepsis, typically, but not always, result from an interaction between a pathogenic microorganism and the host's defense system that triggers an excessive and dysregulated inflammatory response in the host. The complexity of the host's response during the systemic inflammatory response has complicated efforts towards understanding disease pathogenesis (reviewed in Healy, 2002, *Ann. Pharmacother.* 36:648-54). An incomplete understanding of the disease pathogenesis, in turn, contributes to the difficulty in finding useful diagnostic biomarkers. Early and reliable diagnosis is imperative, however, because of the remarkably rapid progression of sepsis into a life-threatening condition.

The development of sepsis in a subject follows a well-described course, progressing from systemic inflammatory response syndrome ("SIRS")-negative, to SIRS-positive, and then to sepsis, which may then progress to severe sepsis, septic shock, multiple organ dysfunction ("MOD"), and ultimately mortality.

Documenting the presence of the pathogenic microorganisms that are clinically significant to sepsis has proven difficult. Causative microorganisms typically are detected by culturing a subject's blood, sputum, urine, wound secretion, in-dwelling line catheter surfaces, etc. Causative microorganisms, however, may reside only in certain body microenvironments such that the particular material that is cultured may not contain the contaminating microorganisms. Detection may be complicated further by low numbers of microorganisms at the site of infection. Low numbers of pathogens in blood present a particular problem for diagnosing sepsis by culturing blood. In one study, for example, positive culture results were obtained in only 17% of subjects presenting clinical manifestations of sepsis (Rangel-Frausto et al., 1995, *JAMA* 273:117-123). Diagnosis can be further complicated by contamination of samples by non-pathogenic microorganisms. For example, only 12.4% of detected microorganisms were clinically significant in a study of 707 subjects with septicemia (Weinstein et al., 1997, *Clinical Infectious Diseases* 24:584-602).

The difficulty in early diagnosis of sepsis is reflected by the high morbidity and mortality associated with the disease. Sepsis currently is the tenth leading cause of death in the United States and is especially prevalent among hospitalized patients in non-coronary intensive care units (ICUs), where it is the most common cause of death. The overall rate of mortality is as high as 35%, with an estimated 750,000 cases per year occurring in the United States alone. The annual cost to treat sepsis in the United States alone is on the order of billions of dollars.

Most existing sepsis scoring systems or predictive models predict only the risk of late-stage complications, including death, in patients who already are considered septic and do not predict the development of sepsis itself. Often, the diagnosis of sepsis is based on clinical suspicion with an empirical score system such as, APACHE II (Knaus et al., 1985, *Crit. Care Med.* 13:818-829), followed by blood culture. It can take 48 hours or longer to confirm any systemic infections. By then, it is often too late to save some patients. If the diagnosis or prognosis of sepsis can be made early, the treatment can be made available to prevent or slow the progress of sepsis into severe sepsis or septic shock.

A need, therefore, exists for methods of diagnosing systemic inflammatory conditions, including sepsis, using techniques that have satisfactory specificity and sensitivity, sufficiently early to allow effective intervention and prevention.

3. SUMMARY OF THE INVENTION

In one aspect, the present invention is based, in part, on the discovery that the amount of total lysophosphatidylcholine in a sample from a patient can be used for rapid, sensitive and accurate diagnosis or prognosis of a systemic inflammatory condition in a subject. In aspects of the invention, total lysophosphatidylcholine in a sample from a patient is used to assess presence of or risk for the systemic inflammatory condition. As shown in the examples below, the methods and compositions of the invention can be used for the diagnosis or prognosis of the systemic inflammatory condition. The systemic inflammatory condition can be any systemic inflammatory condition known to those of skill in the art including systemic inflammatory response syndrome ("SIRS"), sepsis, severe sepsis, septic shock, multiple organ dysfunction ("MOD") and mortality.

In certain embodiments, total lysophosphatidylcholine in a sample of the subject is evaluated to assess presence or risk for a systemic inflammatory condition. As described herein, it has been discovered that the amount of total lysophosphatidylcholine in a sample from a patient can correlate with the onset of a systemic inflammatory condition and can even indicate the condition in advance of its onset. As a result, in certain embodiments, total lysophosphatidylcholine in a sample from the patient can be used as a prognosis for a systemic inflammatory condition. The evaluation can proceed according to any technique for evaluating total lysophosphatidylcholine known to those of skill in the art. Exemplary techniques are described herein. However, the present invention provides methods based on any technique of evaluating total lysophosphatidylcholine apparent to those of skill in the art.

In another aspect, the present invention is based, in part, on the discovery of a class of lysophosphatidylcholine biomarkers that are useful for rapid, sensitive and accurate diagnosis or prognosis of a systemic inflammatory condition in a subject. In aspects of the invention, evaluation of a biomarker of the invention in the subject is used to assess presence of or risk for the systemic inflammatory condition. As shown in the examples below, the methods and compositions of the invention can be used for the diagnosis or prognosis of the systemic inflammatory condition with accuracy up to 80% or more in a time as short as, for example, eight or even six hours. The systemic inflammatory condition can be any systemic inflammatory condition known to those of skill in the art including systemic inflammatory response syndrome ("SIRS"), sepsis, severe sepsis, septic shock and multiple organ dysfunction ("MOD").

In certain embodiments, the biomarker is a 1-O-acyl-2-lyso-sn-glycero-3-phosphocholine. The acyl group can be any acyl group known to those of skill in the art. In certain embodiments, the acyl group is $C_{14}$-$C_{22}$ acyl. In further embodiments, the acyl group is $C_{16}$-$C_{18}$ acyl. In particular embodiments, the acyl group is $C_{16}$ acyl. In a preferred embodiment, the acyl group is palmitoyl. In further particular embodiments, the acyl group is $C_{18}$ acyl. In a preferred embodiment, the acyl group is stearoyl. The biomarker can be any form of the biomarker from the subject, for instance any salt or solvate of the biomarker that can be identified by those of skill in the art.

In certain embodiments, the biomarker is a compound according to formula (I):

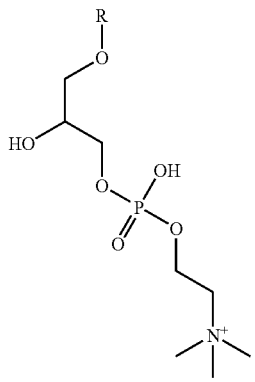

(I)

or a salt or solvate thereof. In formula (I), R can be any acyl group known to those of skill in the art. In certain embodiments, R is $C_{14}$-$C_{22}$ acyl. In further embodiments, R is $C_{16}$-$C_{18}$ acyl. In particular embodiments, R is $C_{16}$ acyl. In a preferred embodiment, R is palmitoyl. In further particular embodiments, R is $C_{18}$ acyl. In a preferred embodiment, R is stearoyl.

Exemplary salts of formula (I) are provided by formula (Ia):

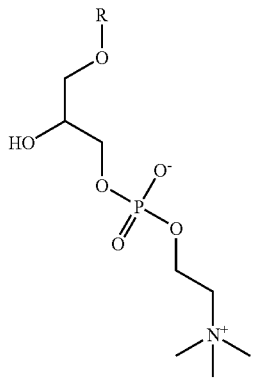

(Ia)

wherein said salt can be coordinated with any physiological organic or inorganic anion, or any physiological organic or inorganic cation, or both, known to those of skill in the art. Exemplary physiological anions include chloride, bromide, phosphate, acetate, carbonate, bicarbonate and sulfate. Exemplary physiological cations include sodium, potassium, calcium, magnesium and ammonium.

In certain aspects, the biomarker in the subject is evaluated to assess presence or risk for the systemic inflammatory condition. The evaluation can proceed according to any method of evaluating a biomarker known to those of skill in the art. In certain embodiments, the amount of the biomarker is measured in a fluid of a subject. However, the present invention provides methods based on any technique of evaluating a biomarker of the invention apparent to those of skill in the art.

In the following description, the term lysophosphatidylcholine can refer to total lysophosphatidylcholine or to a lysophosphatidylcholine biomarker, unless specified otherwise. Of course, the present invention provides prognosis or diagnosis based on total lysophosphatidylcholine, prognosis or diagnosis based on one or more lysophosphatidylcholine biomarkers of the invention, and prognosis or diagnosis based on total lysophosphatidylcholine along with one or more lysophosphatidylcholine biomarkers of the invention.

In some embodiments, a plurality of measurements of lysophosphatidylcholine in the subject are made over time. The time intervals can be, for instance, 3 hours, 4 hours, 6 hours, 12 hours, 24 hours or other intervals according to the judgment of the practitioner in the art. In these embodiments, the relative amounts of lysophosphatidylcholine are evaluated for the diagnosis or prognosis of the systemic inflammatory condition by a practitioner of skill in the art. In particular embodiments, decreasing amounts of lysophosphatidylcholine indicate increasing risk for the systemic inflammatory condition, and increasing amounts of total lysophosphatidylcholine indicate decreasing risk for the systemic inflammatory condition.

In advantageous embodiments, a single sample from the subject can be sufficient for the diagnosis or prognosis of the systemic inflammatory condition. The amount of lysophosphatidylcholine can be compared to one or more biomarkers present in the sample that are known to those of skill in the art to be maintained at a relatively constant amount in the sample in individuals similar to the subject. The amount of lysophosphatidylcholine of the invention can be assessed against this internal standard for the diagnosis or prognosis of the systemic inflammatory condition by the practitioner of skill. In particular embodiments, low amounts of lysophosphatidylcholine indicate increased risk for the systemic inflammatory condition, and high amounts of lysophosphatidylcholine indicate reduced risk for the systemic inflammatory condition.

In other embodiments, the evaluation is based on a comparison of the amount of lysophosphatidylcholine to a reference amount of lysophosphatidylcholine. The reference amount can be, for instance, the amount of lysophosphatidylcholine in a reference individual that manifests, or will manifest within a defined period of time, one or more symptoms of the known systemic inflammatory condition. The amount can be, for instance, an absolute value or an absolute value with a margin of error or a range of values, as determined by those of skill in the art. In certain embodiments, the reference individual exhibits, or will exhibit, symptoms of SIRS, sepsis, severe sepsis, septic shock or MOD or no symptoms of a systemic inflammatory condition. In particular embodiments, low amounts of lysophosphatidylcholine (e.g. relative to a reference amount) indicate increased risk for the systemic inflammatory condition, and high amounts of lysophosphatidylcholine indicate reduced risk for the systemic inflammatory condition.

Advantageously, the reference amount need not be determined by one carrying out a method of the invention. Instead, the reference amount of lysophosphatidylcholine can be identified by consulting data available to those of skill in the art. Such data can be obtained from any source available to those of skill in the art. In certain embodiments, sources can be developed with reference amounts of lysophosphatidylcholine collected by those of skill in the art according to methods described herein.

In certain embodiments, the reference amount is from a reference individual presenting symptoms of the systemic inflammatory condition. The reference individual can present symptoms of SIRS, sepsis, severe sepsis, septic shock, MOD or mortality or no symptoms of a systemic inflammatory condition. In certain embodiments, the reference amount can be evaluated at a time prior to or after presentation of symptoms. For instance, in an advantageous embodiment, a reference amount can be the amount measured in a SIRS-positive individual 12, 24, 36 or 48 hours prior to the onset of sepsis. Measurement of such reference amounts is within the skill of those in the art.

In further embodiments, reference amounts are from a plurality of individuals presenting symptoms of one or more systemic inflammatory conditions. The reference amounts can be calculated according to any suitable statistical method known to those of skill in the art. For instance, the reference amounts can be based on the statistical mean of reference amounts from reference individuals presenting a systemic inflammatory condition. In advantageous embodiments, comparison is made to a value or range of values for the amount of lysophosphatidylcholine. The value or range of values can be obtained as described herein and made available to a practitioner of the methods of the invention. In particular embodiments, low amounts of lysophosphatidylcholine (e.g. relative to a reference amount) indicate increased risk for the systemic inflammatory condition, and high amounts of lysophosphatidylcholine indicate reduced risk for the systemic inflammatory condition.

The comparison can be according to any technique for comparing amounts of biomarkers known to those of skill in the art. In one embodiment, the diagnosis or prognosis of a systemic inflammatory condition is based on the difference between the amount of lysophosphatidylcholine in the subject and the reference amount. In certain embodiments the difference between the amount of lysophosphatidylcholine in the subject and the reference amount correlates inversely with risk for the systemic inflammatory condition. In further embodiments, the reference amount is a cutoff—in other words, the subject can be assessed to have or have risk for the systemic inflammatory condition if the amount of lysophosphatidylcholine in the subject is less than a cutoff reference amount. Such cutoff reference amounts can be calculated according to methods described herein.

The amount of total lysophosphatidylcholine in the subject can be determined according to any technique known to those of skill in the art without limitation. In certain embodiments, one of skill can measure an amount that correlates to the amount of total lysophosphatidylcholine in a sample. For instance, in particular embodiments, one of skill can measure total free lysophosphatidylcholine, total bound lysophosphatidylcholine or total free and bound lysophosphatidylcholine in the sample to indicate the amount of total lysophosphatidylcholine in the sample. In other words, in certain embodiments, measurement of free or bound, or both free and bound, lysophosphatidylcholine can correlate to the amount of total lysophosphatidylcholine. In certain embodiments, the technique for evaluating total lysophosphatidylcholine is not critical for the invention and need not be carried out by one practicing the methods herein. For instance, in particular embodiments, methods of the invention can comprise the single step of comparing total lysophosphatidylcholine amount in a subject to a reference total lysophosphatidylcholine amount in order to assess risk for the systemic inflammatory condition without regard to how either amount is measured. In further embodiments, total lysophosphatidylcholine of the subject is evaluated by a technique described herein followed by comparing to a reference total lysophosphatidylcholine in order to assess risk for the systemic inflammatory condition. In certain embodiments, total lysophosphatidylcholine is evaluated by spectrometry, chromatography, immunoassay, electrophoresis or enzymatic assay as described in detail below.

In one aspect, the present invention provides fluorescent methods for assaying total lysophosphatidylcholine in a sample of a subject. In certain embodiments, the methods comprise contacting the sample of the subject with one or more reagents capable of generating a fluorescent product indicative of total lysophosphatidylcholine in the sample. The methods can be used to detect the presence of total lysophosphatidylcholine or to detect the amount of total lysophosphatidylcholine, or both, in the sample. In particular embodiments, the sample is contacted with a fluorogenic substrate of one or more of the reagents. This fluorogenic substrate can be converted to the fluorescent product indicating total lysophosphatidylcholine. In advantageous embodiments, the reagents comprise peroxidase, choline oxidase, glycerophosphatidylcholine diesterase and lysophospholipase. A useful fluorogenic substrate is 10-acetyl-3,7-dihydroxyphenoxazine, a compound that can be converted to the fluorescent product 7-hydroxy-3H-phenoxazin-3-one. Advantageously, such methods can provide the sensitivity necessary for detecting the low amounts of total lysophosphatidylcholine in subjects having, or at risk for, a systemic inflammatory condition.

The amount of the biomarker in the subject can be determined according to any technique known to those of skill in the art without limitation. In certain embodiments, the technique for evaluating the biomarker is not critical for the invention and need not be carried out by one practicing the methods herein. For instance, in particular embodiments, methods of the invention can comprise the single step of comparing the biomarker in a subject to a reference biomarker in order to assess risk for the systemic inflammatory condition without regard to how either biomarker is measured. In further embodiments, the biomarker of the subject is evaluated by a technique described herein followed by comparing the biomarker in a subject to a reference biomarker in order to assess risk for the systemic inflammatory condition. In certain embodiments, the biomarker is evaluated by spectrometry, chromatography, immunoassay or electrophoresis as described in detail below.

The amount of lysophosphatidylcholine can be measured in fluids or tissues of the subject as provided herein. Processes for preparing the fluid or tissue, for example, processes for extracting or purifying lysophosphatidylcholine are described herein. Further, techniques for measuring lysophosphatidylcholine are provided herein.

In another aspect, the present invention provides methods for monitoring a systemic inflammatory condition in a subject. In such methods, evaluation of lysophosphatidylcholine is used to monitor a systemic inflammatory condition in the subject. In such methods, changes in the amount of lysophosphatidylcholine indicate changes in the systemic inflammatory condition. For instance, in certain embodiments, increasing amounts of lysophosphatidylcholine indicate decreased severity or less risk for the systemic inflammatory condition, and decreasing amounts of lysophosphatidylcholine indicate increased severity or increased risk for the systemic inflammatory condition. In some embodiments, evaluation of lysophosphatidylcholine car indicate conversion from one systemic inflammatory condition to another such as SIRS, sepsis, severe sepsis, septic shock, MOD or mortality or no systemic inflammatory condition.

In another aspect, the present invention provides methods for monitoring treatment of a systemic inflammatory condition in a subject. In such methods, evaluation of lysophosphatidylcholine is used to monitor the systemic inflammatory condition in the subject. In such methods, changes in the amount of lysophosphatidylcholine indicate changes in the systemic inflammatory condition. For instance, in certain embodiments, increasing amounts of lysophosphatidylcholine indicate decreased severity or less risk for the systemic inflammatory condition, and decreasing amounts of total lysophosphatidylcholine indicate increased severity or increased risk for the systemic inflammatory condition. Advantageously, treatment of the systemic inflammatory condition can be adjusted based on the monitoring. In some embodiments, evaluation of lysophosphatidylcholine can indicate conversion from one systemic inflammatory condition to another such as SIRS, sepsis, severe sepsis, septic shock, MOD or mortality or no systemic inflammatory condition. In preferred embodiments, a subject that is SIRS-negative can be monitored for conversion to SIRS or sepsis or another inflammatory condition. In further preferred embodiments, a subject that is SIRS-positive can be monitored for conversion to sepsis or another systemic inflammatory condition, or for conversion to SIRS-negative.

In another aspect, the present invention provides kits for the diagnosis or prognosis of a systemic inflammatory condition. In some embodiments, the kits comprise a composition suitable for evaluation of lysophosphatidylcholine. The kits can further comprise a label or labeling with instructions for using evaluation of total lysophosphatidylcholine for diagnosis or prognosis of one or more systemic inflammatory conditions. In certain embodiments, the kit can comprise a label or labeling with reference amounts, or citations to such reference amounts, of lysophosphatidylcholine to facilitate prognosis or diagnosis of a systemic inflammatory condition with the composition of the kit.

4. BRIEF DESCRIPTION OF THE FIGURES

FIG. 1 provides an exemplary system of the invention;

FIG. 2 provides time course analyses of biomarker 496.3;

FIG. 3 provides time course analyses of biomarker 518.3;

FIGS. 4-2 illustrates evolution of feature inclusion parameters during optimization of methods of the invention;

FIGS. 4-3 illustrates sensitivity and specificity versus threshold in a performance model according to the invention;

FIGS. 4-4 and 4-5 illustrate evolution of feature inclusion parameters during optimization of methods of the invention;

FIGS. 4-6 illustrates sensitivity and specificity versus threshold in a performance model according to the invention;

FIGS. 4-7 through 4-9 illustrate evolution of feature inclusion parameters during optimization of methods of the invention;

FIGS. 5-1 illustrates sensitivity and specificity versus threshold in a performance model according to the invention;

FIGS. 5-2 illustrates evolution of feature inclusion parameters during optimization of methods of the invention;

FIGS. 5-3 illustrates sensitivity and specificity versus threshold in a performance model according to the invention;

FIGS. 5-4 and 5-5 illustrate evolution of feature inclusion parameters during optimization of methods of the invention;

FIGS. 5-6 illustrates sensitivity and specificity versus threshold in a performance model according to the invention;

FIGS. 5-7 through 5-9 illustrate evolution of feature inclusion parameters during optimization of methods of the invention;

Figures 1, 4:
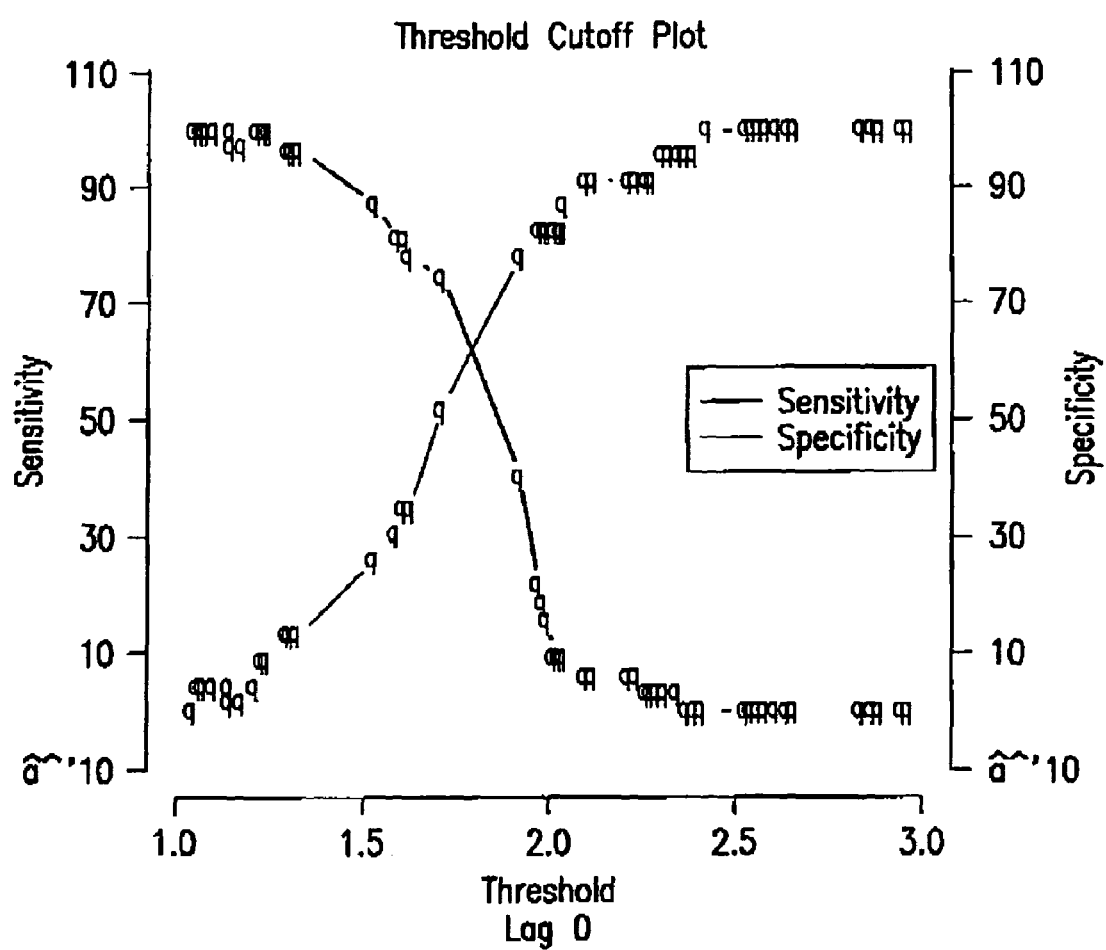
Figures 2, 4:
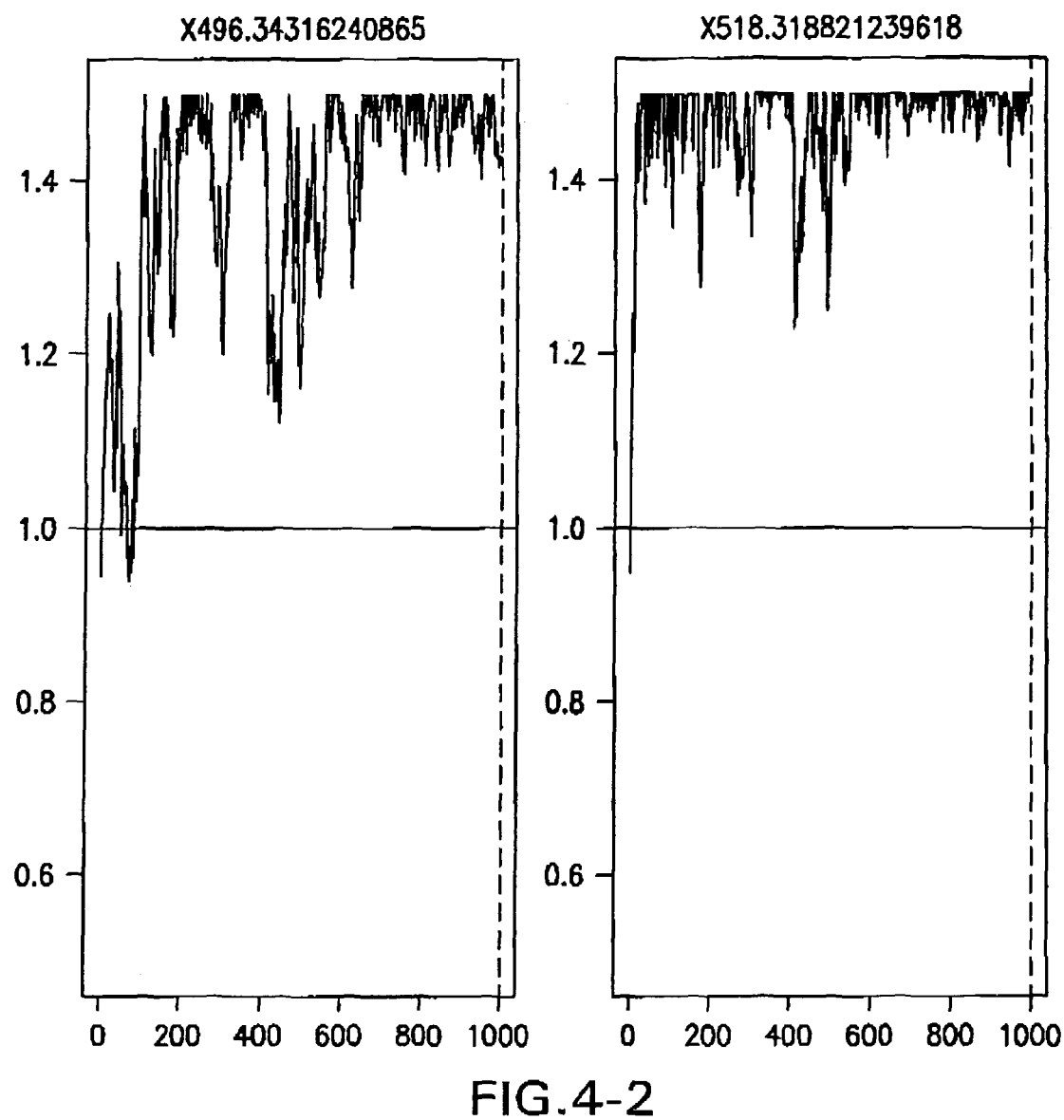
Figures 3, 4:
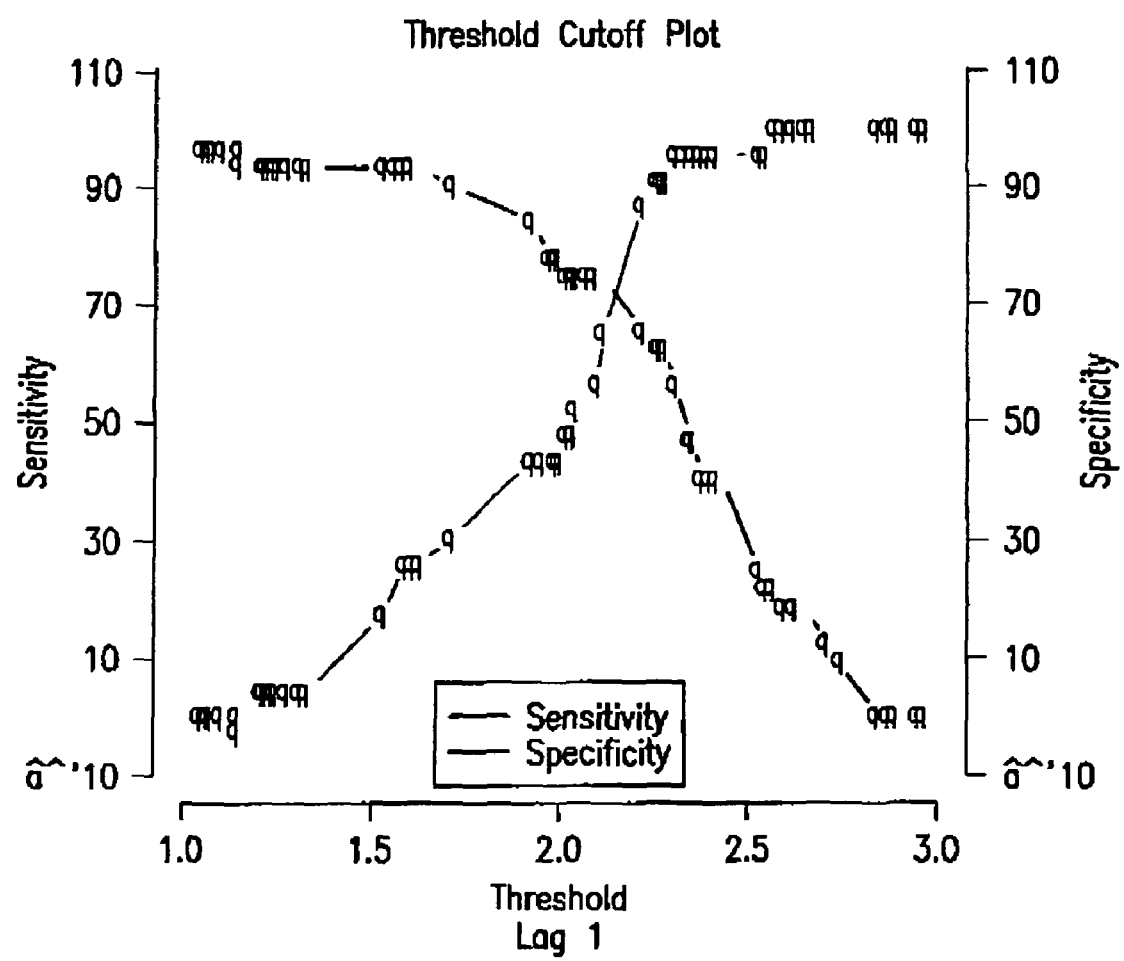
Figure 4:
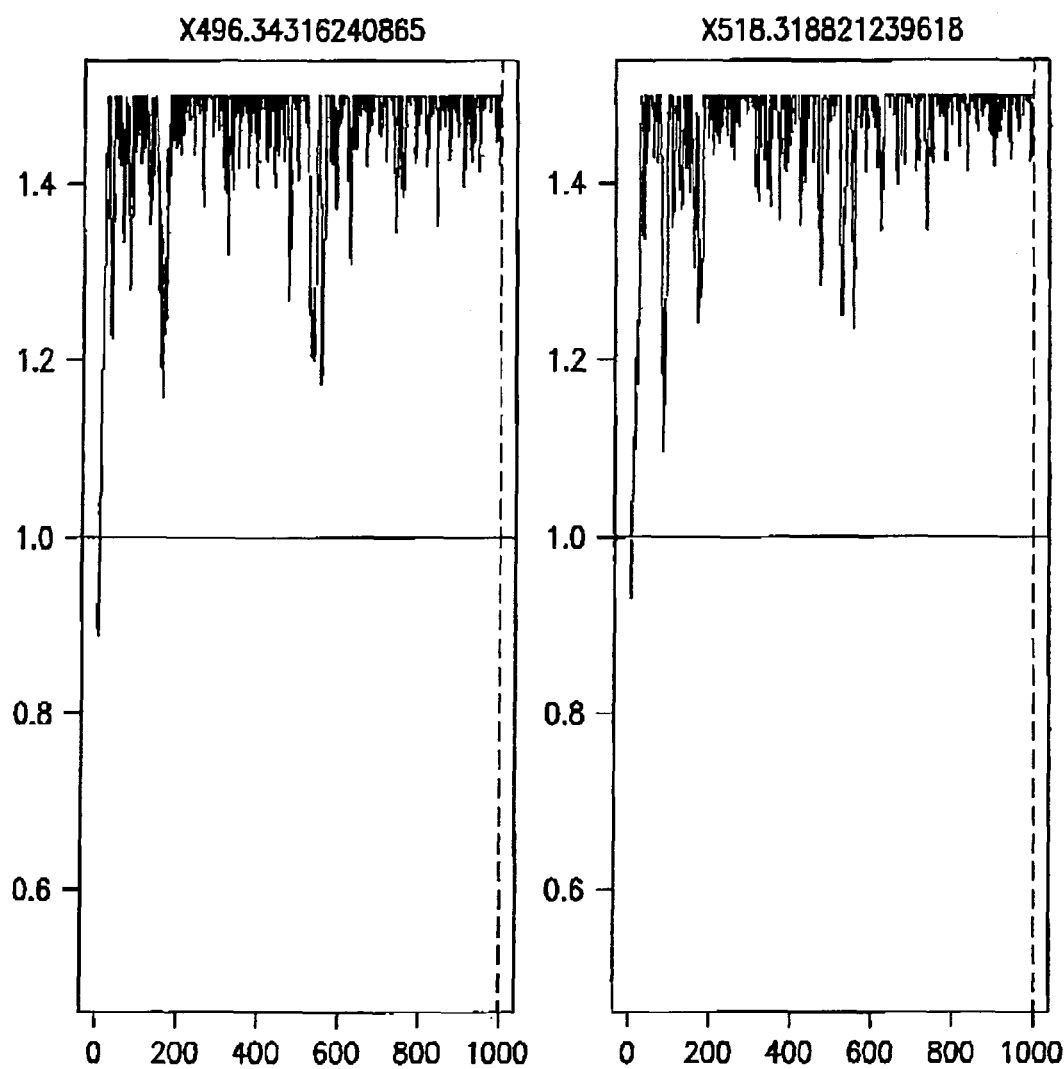
Figures 4, 5:
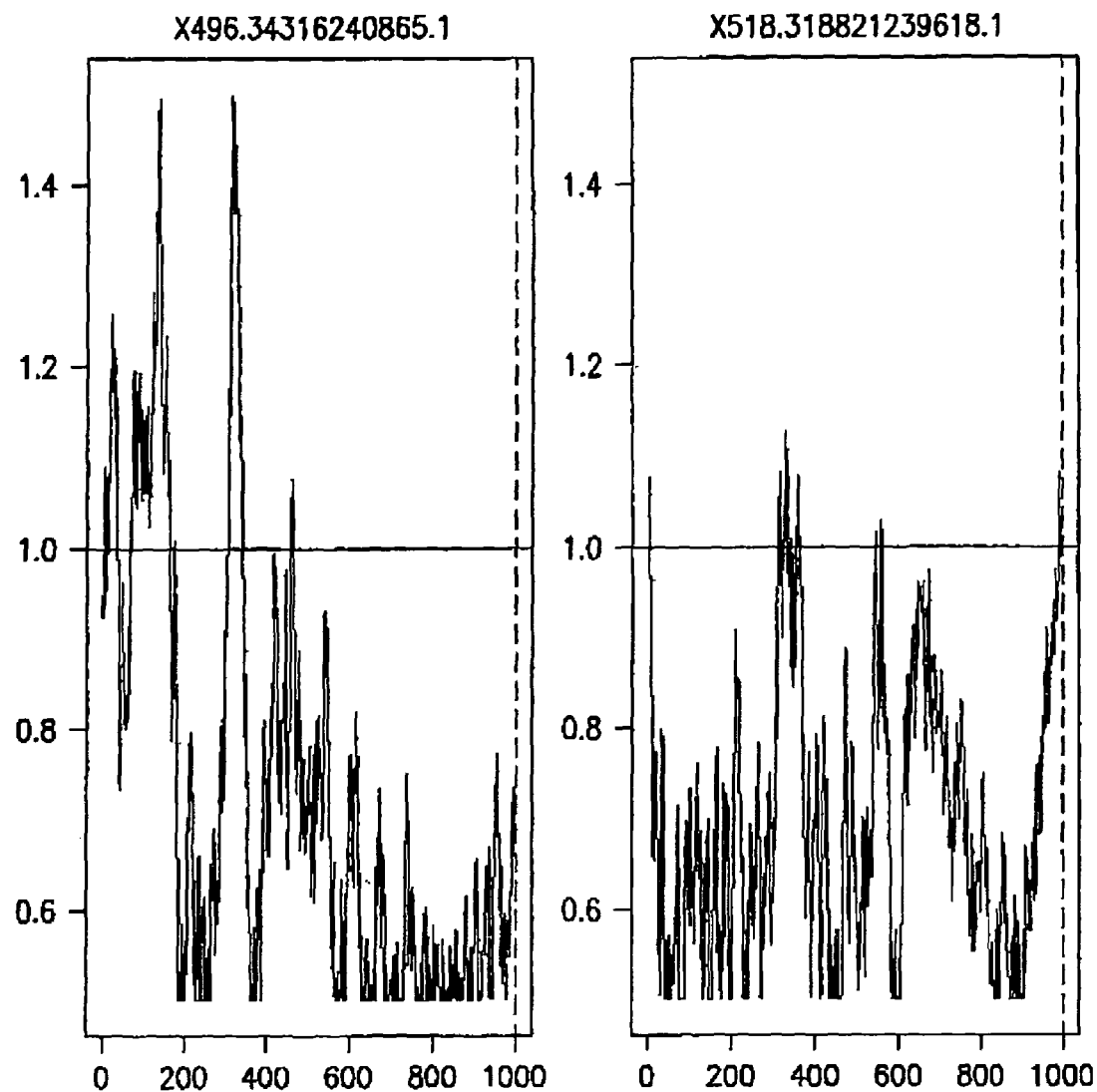
Figures 4, 5, 6:
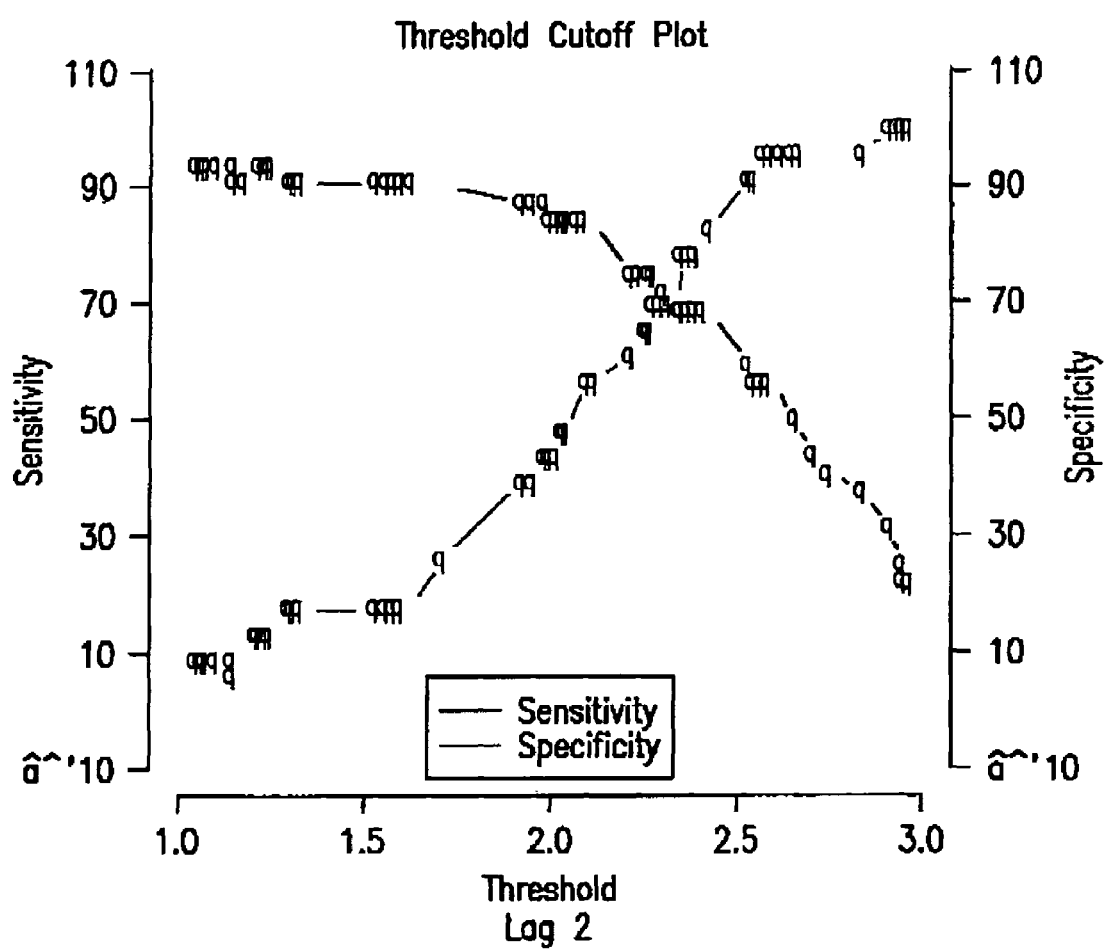
Figures 4, 5, 6, 7:
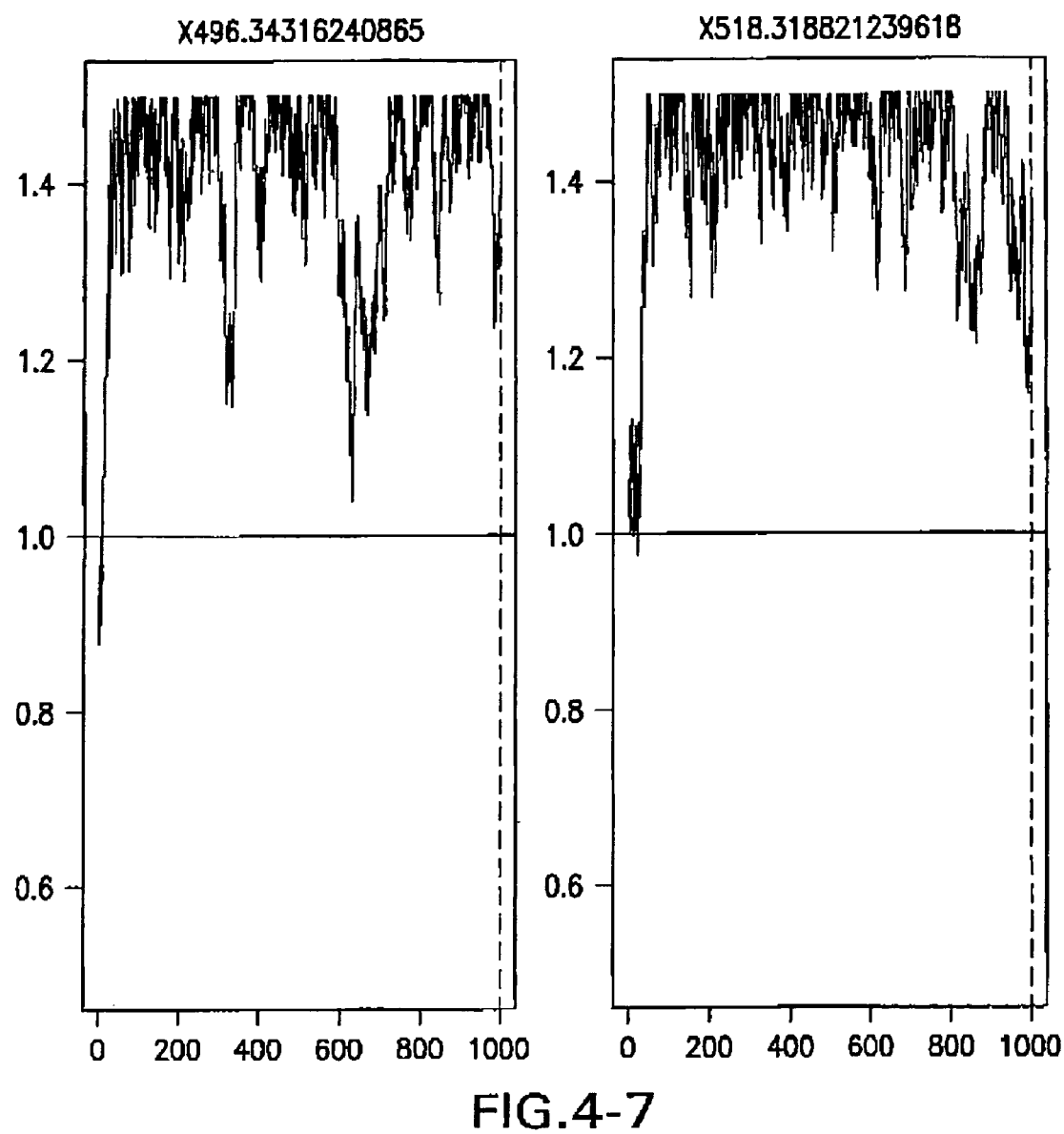
Figures 4, 5, 6, 7, 8:
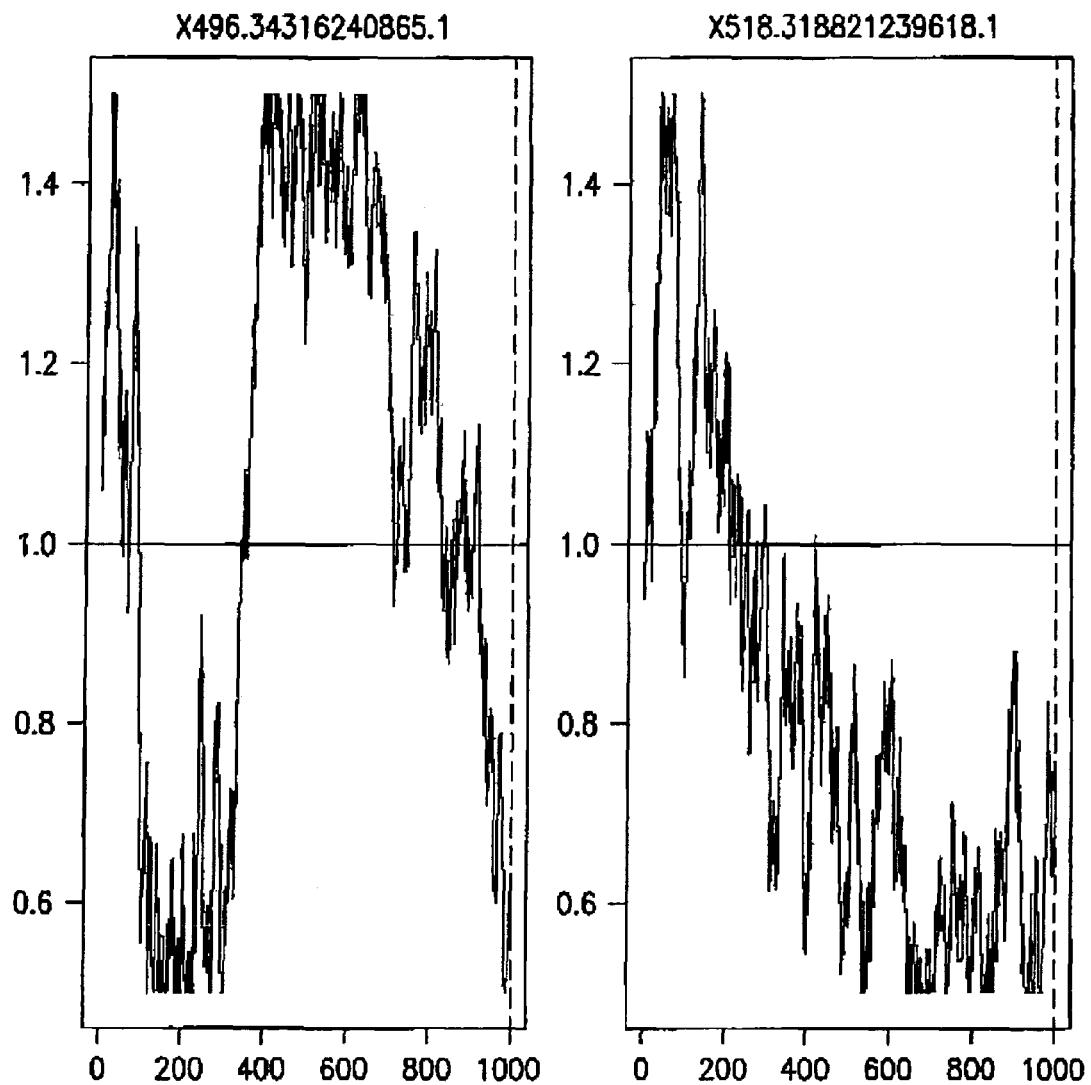
Figures 4, 5, 6, 7, 8, 9:
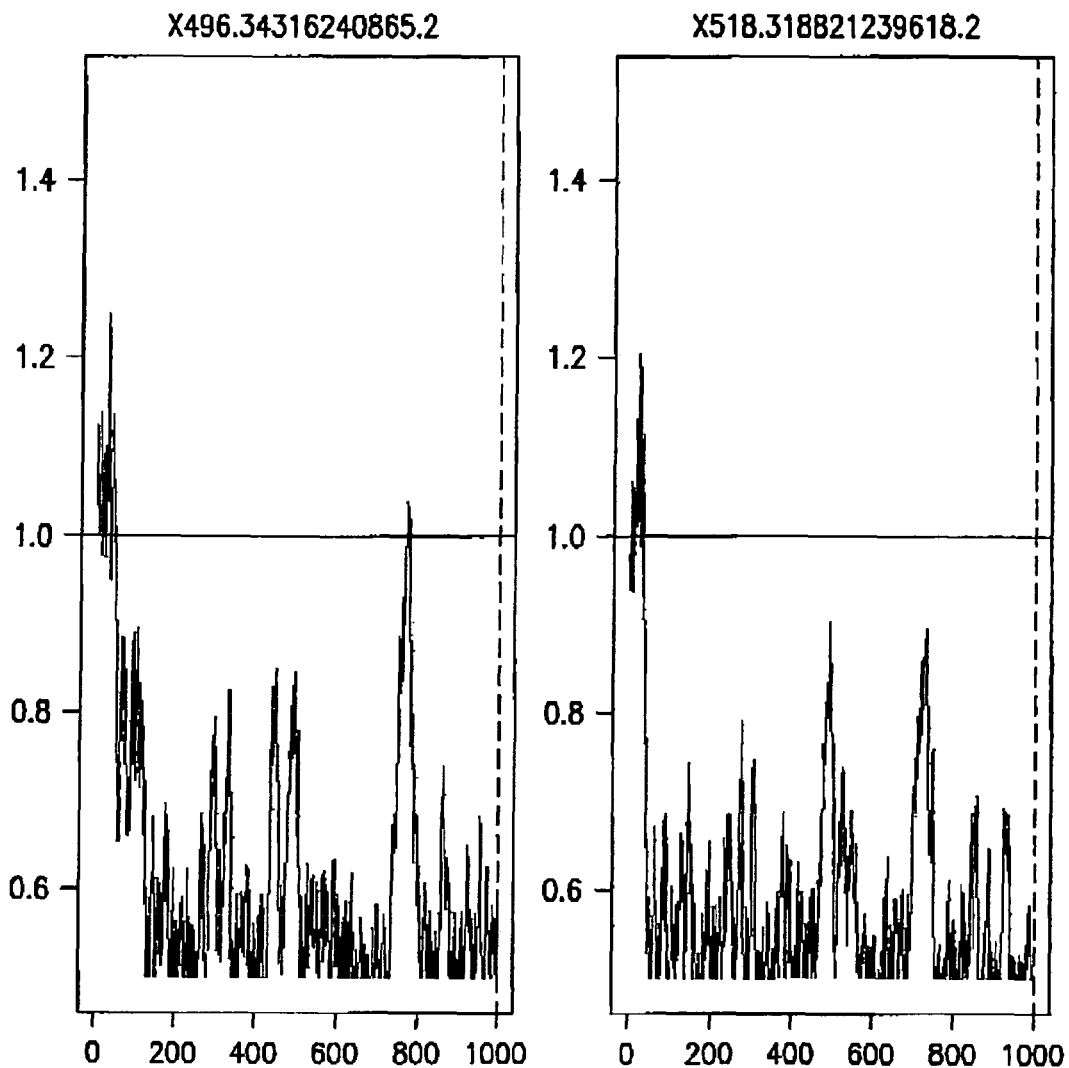
Figures 1, 5:
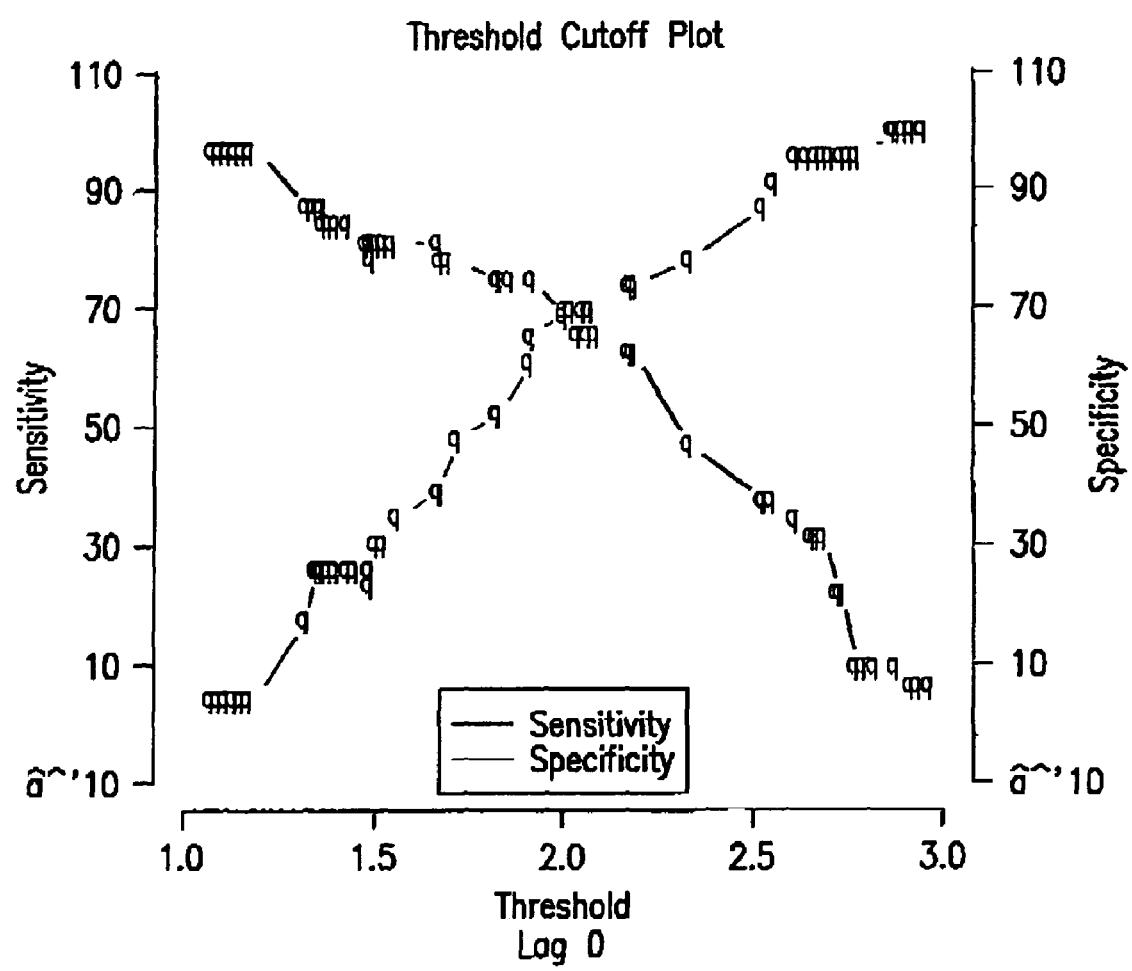
Figures 2, 5:
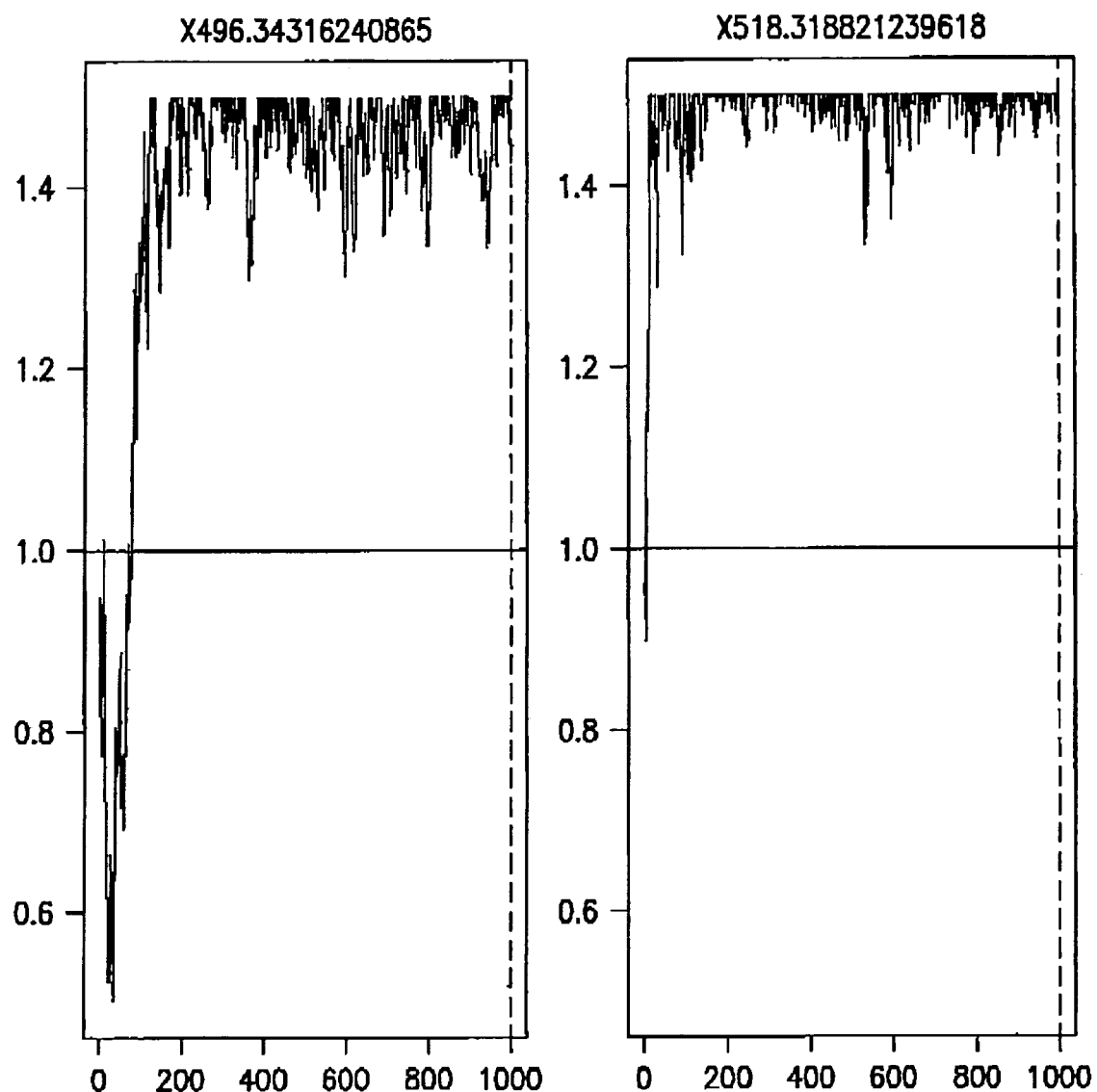
Figures 3, 5:
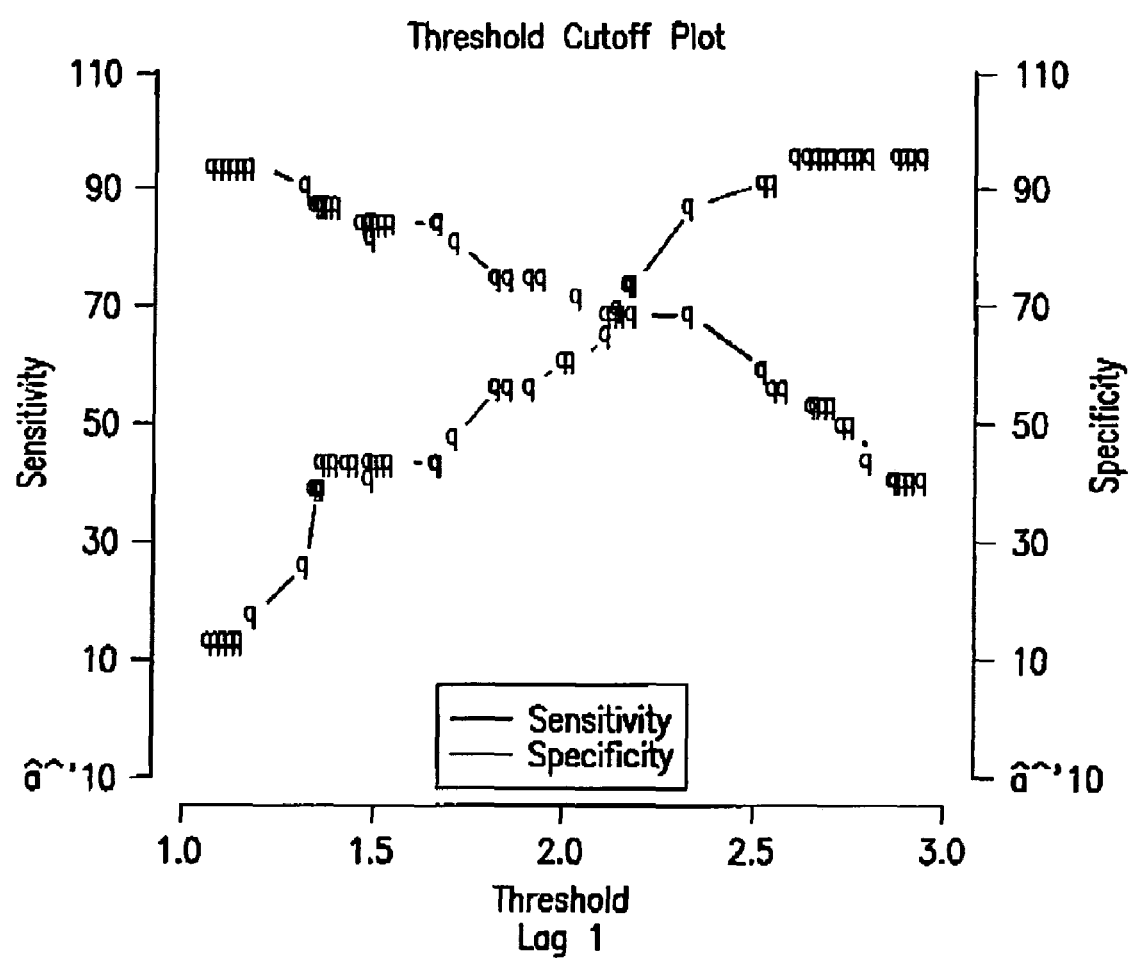
Figures 4, 5:
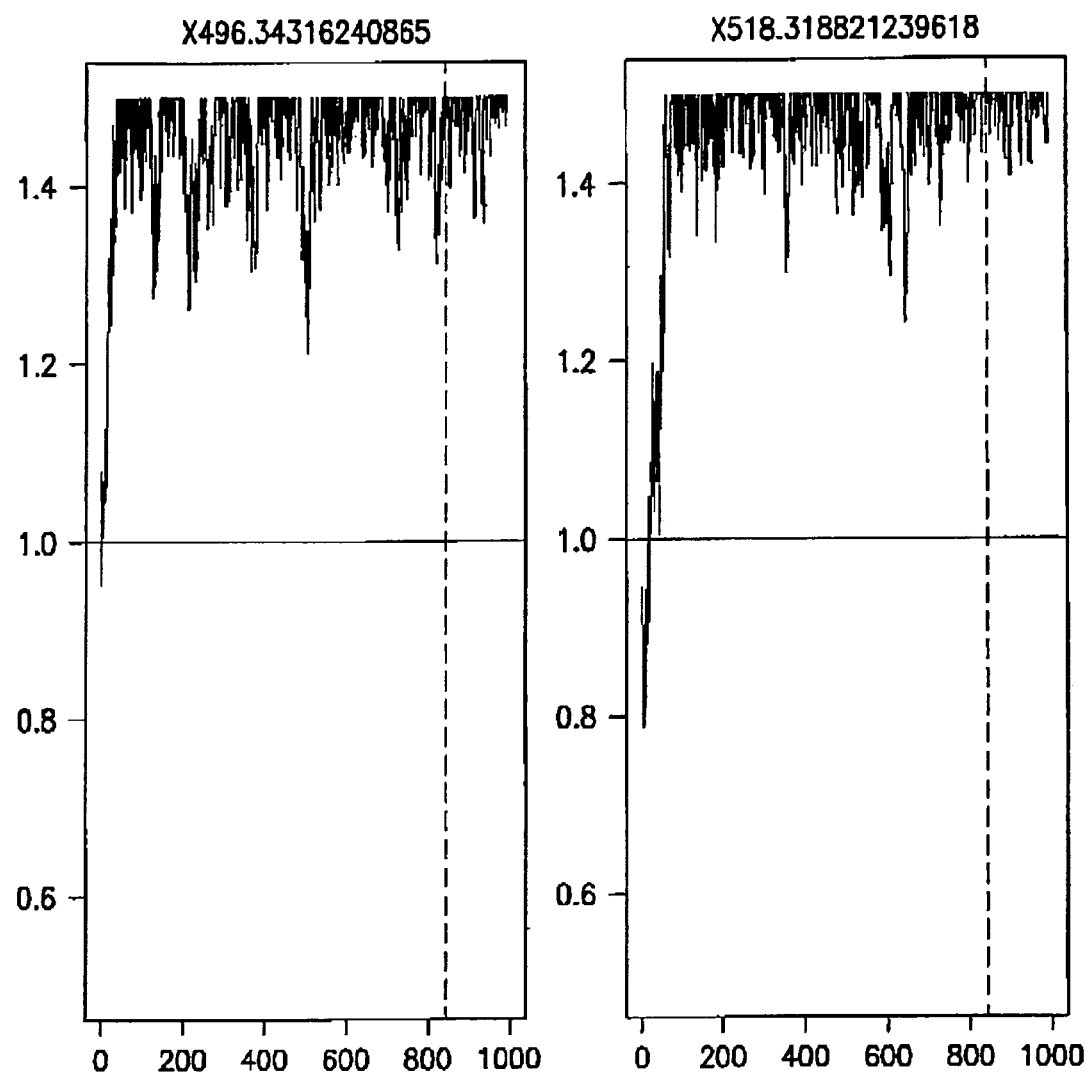
Figure 5:
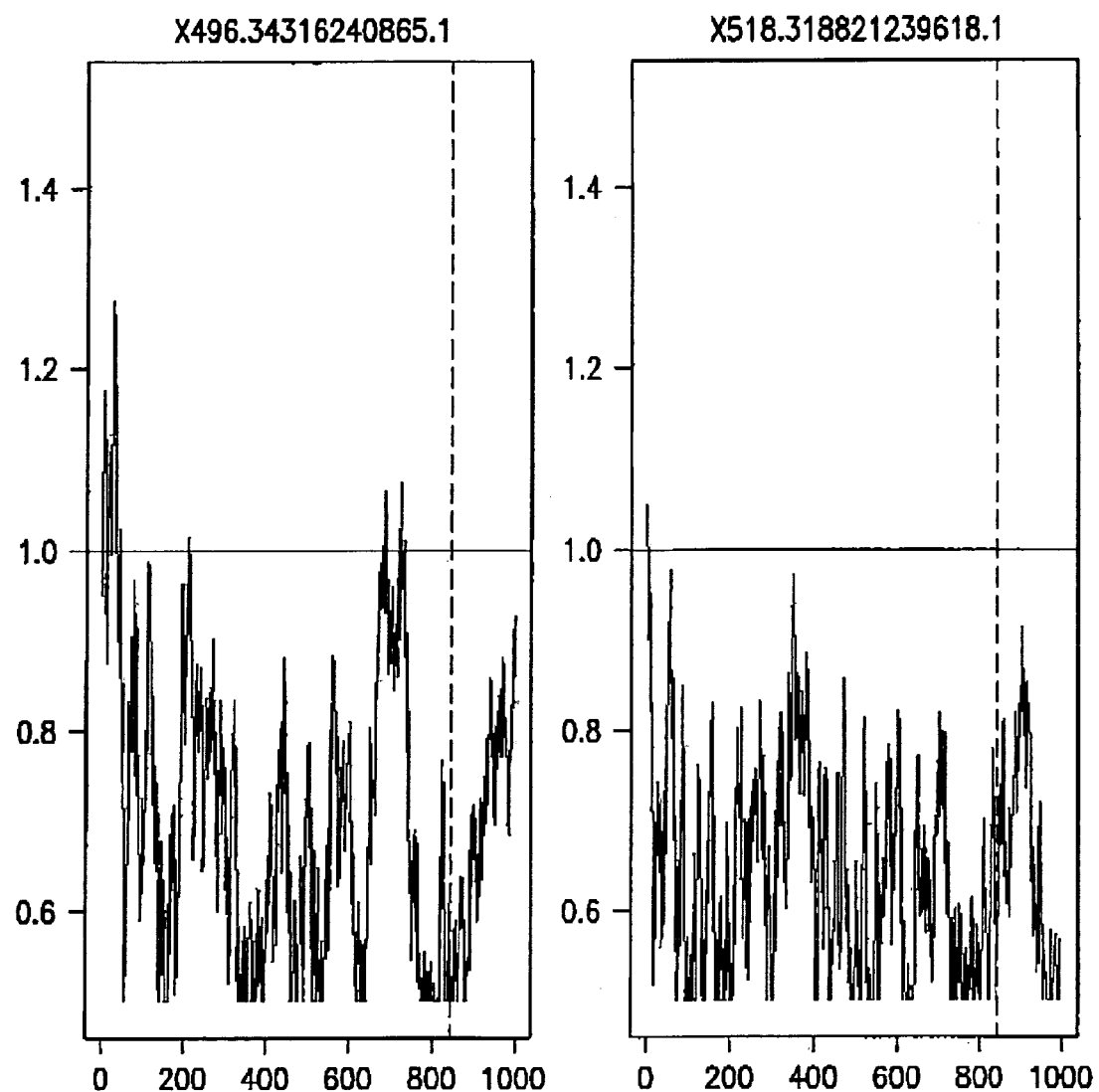
Figures 5, 6:
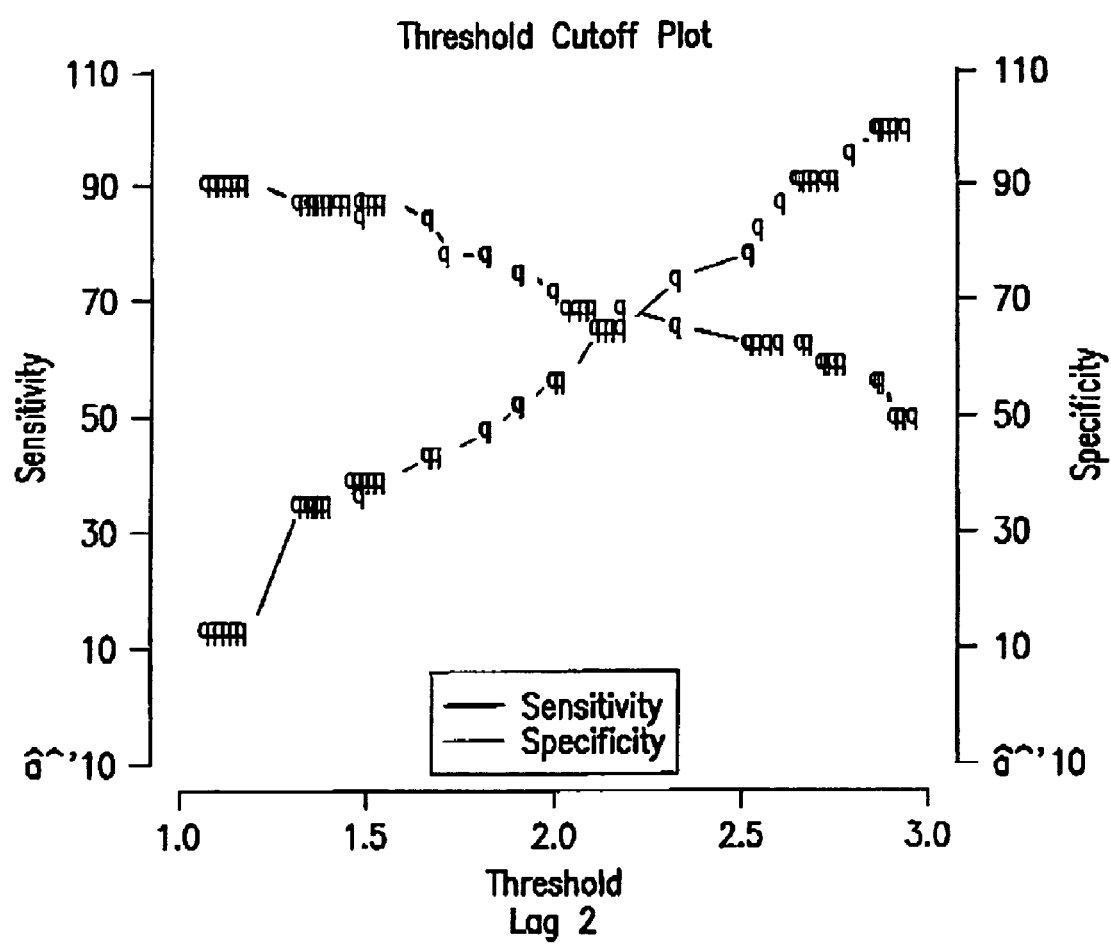
Figures 5, 6, 7:
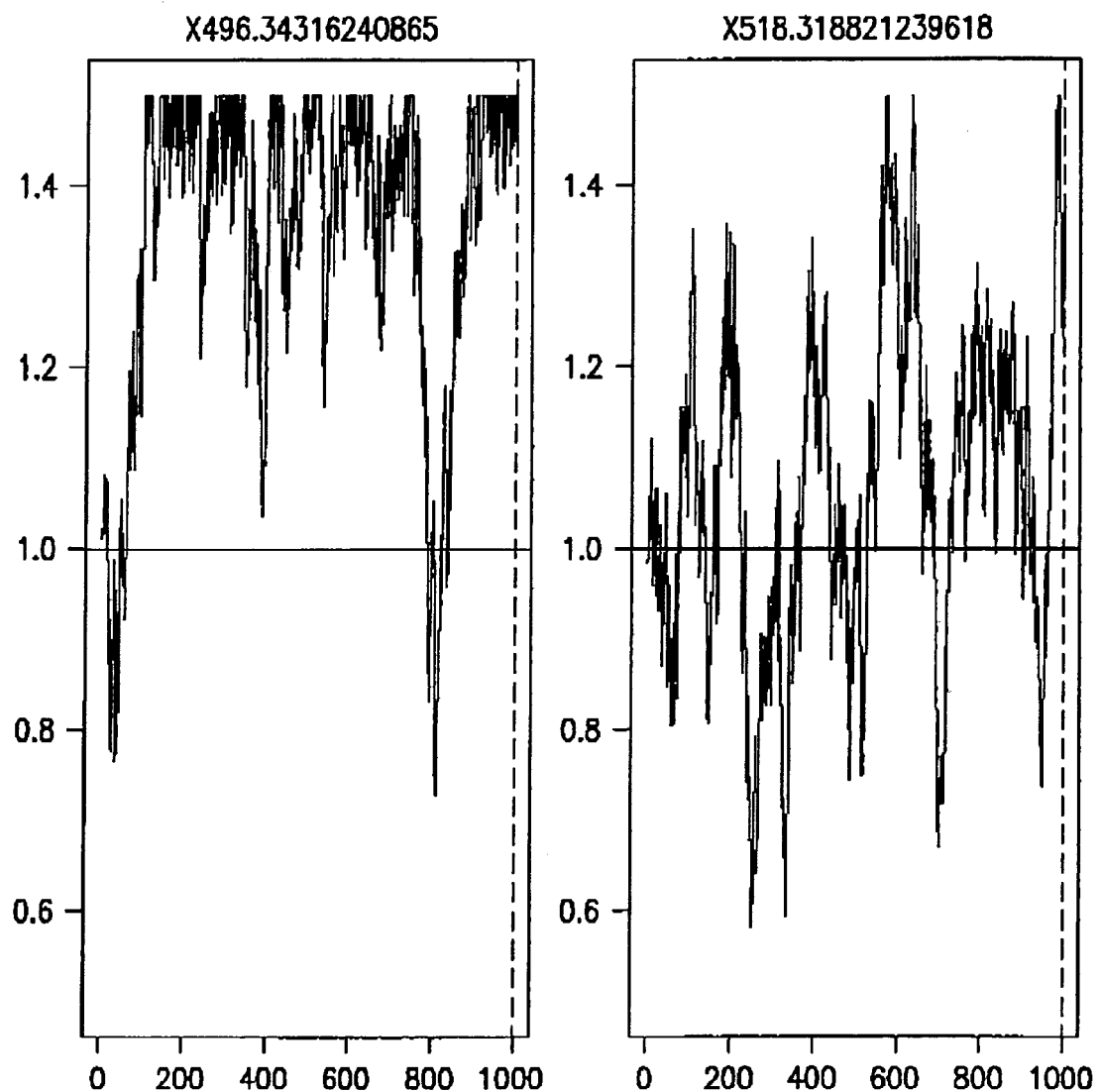
Figures 5, 6, 7, 8:
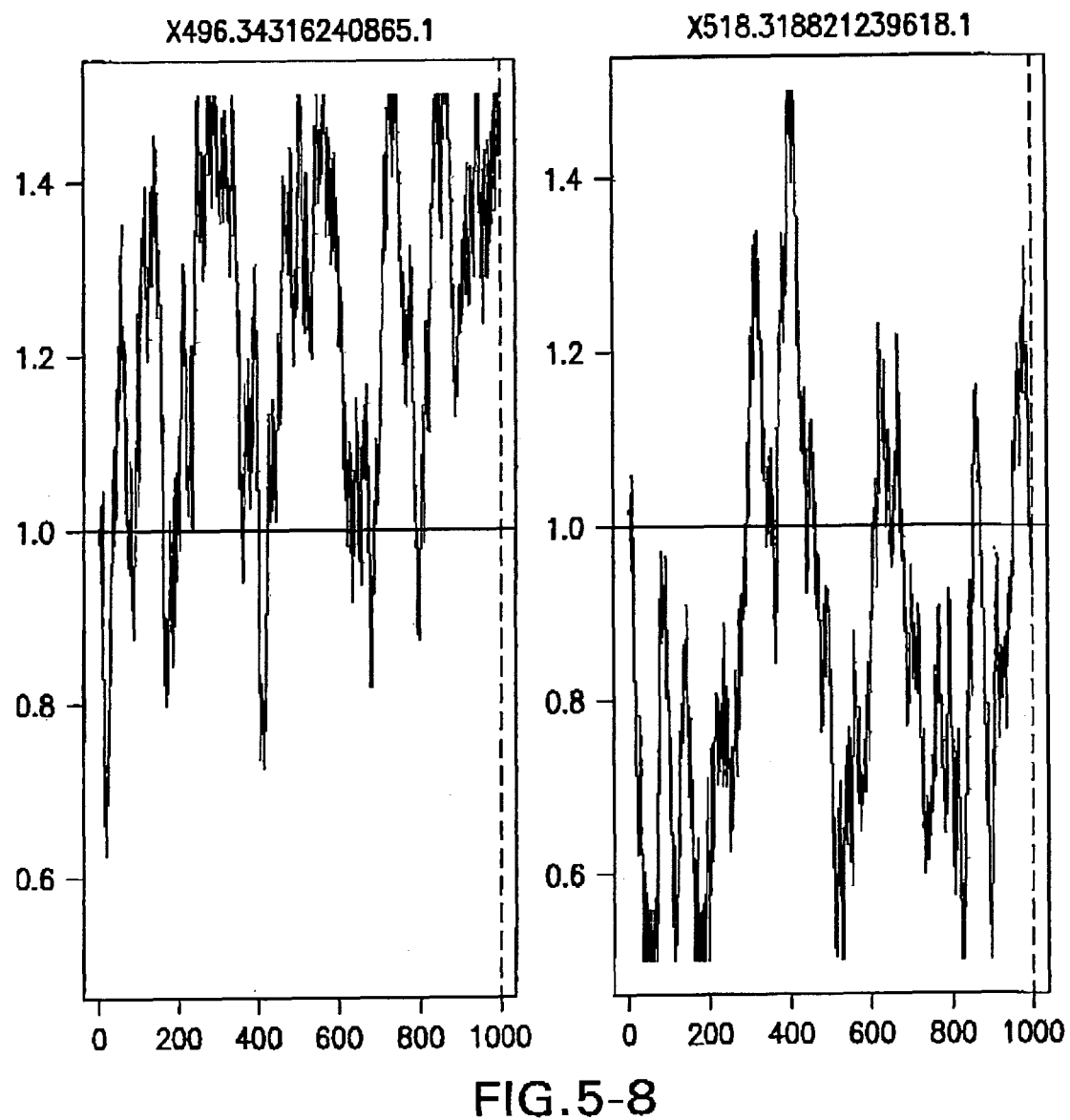
Figures 5, 6, 7, 8, 9:
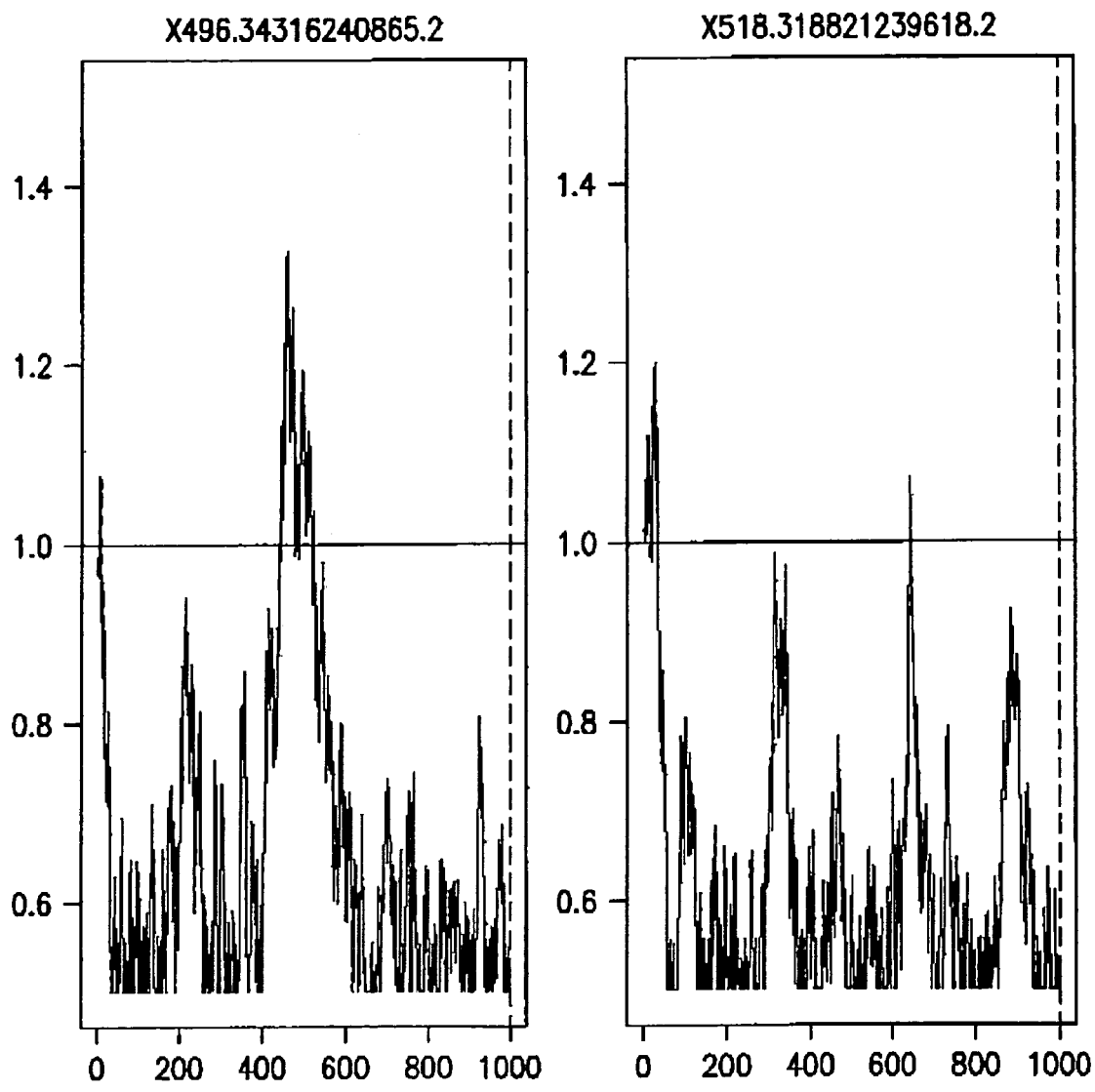
Figure 6:
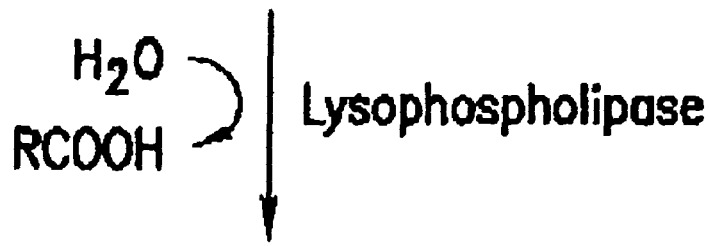
Figure 6:
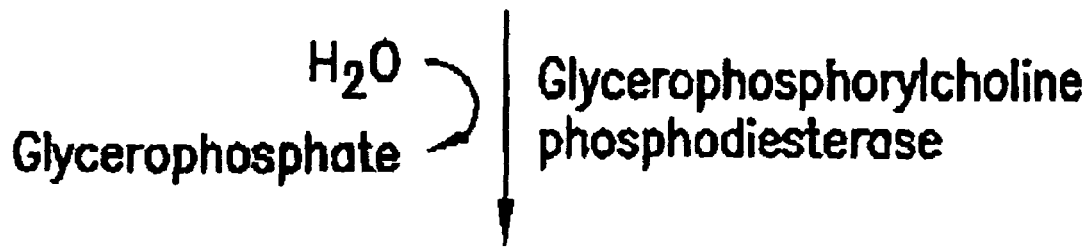
Figure 6:
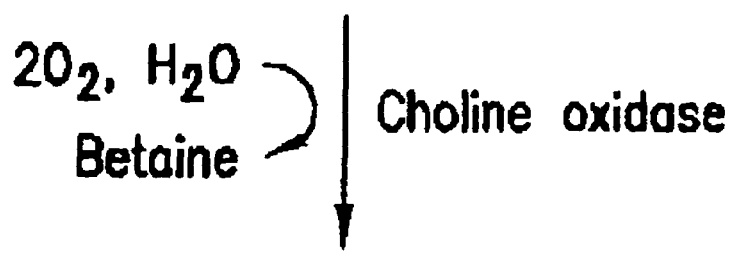
Figure 6:
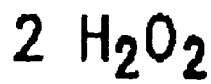
Figure 7:
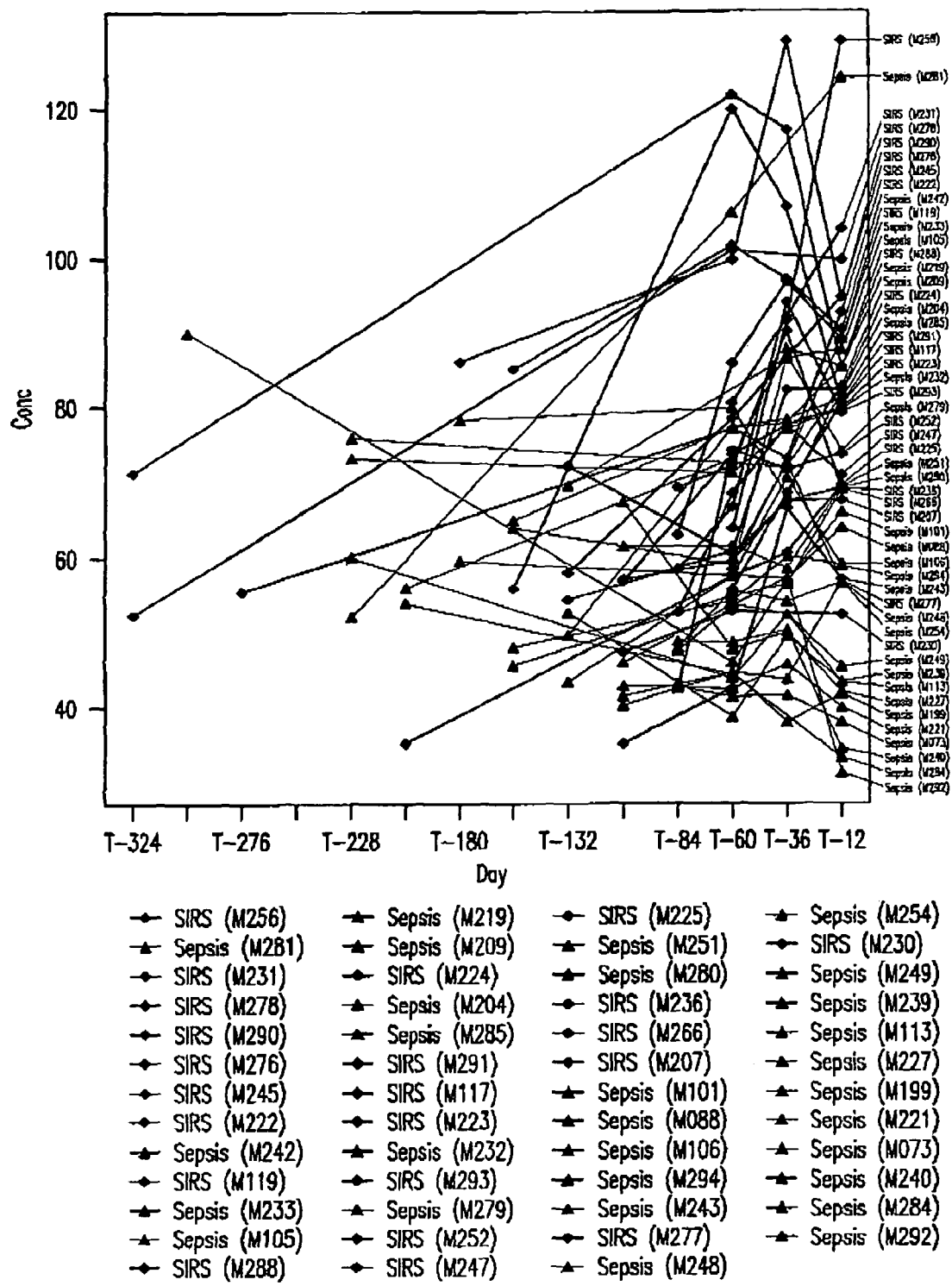

FIG. 6 provides a scheme for detection of lysophosphatidylcholine according to embodiments of the invention; and FIG. 7 provides lysophosphatidylcholine detected fluorescently in samples from patients that showed symptoms of SIRS or sepsis.

5. DETAILED DESCRIPTION OF THE INVENTION

5.1 Definitions

As used herein, the following terms shall have the following meanings:

The term "subject" refers to animals such as mammals, including, but not limited to, primates (e.g., humans), cows, sheep, goats, horses, dogs, cats, rabbits, rats, mice and the like. In preferred embodiments, the subject is human. The term "patient" is interchangeable with a human subject, unless noted otherwise.

"Systemic inflammatory response syndrome," or "SIRS," refers to a clinical response to a variety of severe clinical insults, as manifested by two or more of the following conditions within a 24-hour period:

body temperature greater than 38° C. (100.4° F.) or less than 36° C. (96.8° F.);

heart rate (HR) greater than 90 beats/minute;

respiratory rate (RR) greater than 20 breaths/minute, or $P_{CO2}$ less than 32 mmHg, or requiring mechanical ventilation; and white blood cell count (WBC) either greater than $12.0\times10^9$/L or less than $4.0\times10^9$/L or having greater than 10% immature band forms.

These symptoms of SIRS represent a consensus definition of SIRS that can be modified or supplanted by other definitions in the future. The present definition is used to clarify current clinical practice and does not represent a critical aspect of the invention (see, e.g., American College of Chest Physicians/Society of Critical Care Medicine Consensus Conference: Definitions for Sepsis and Organ Failure and Guidelines for the Use of Innovative Therapies in Sepsis, 1992, *Crit. Care. Med.* 20, 864-874, the entire contents of which are herein incorporated by reference).

A subject with SIRS has a clinical presentation that is classified as SIRS, as defined above, but is not clinically deemed to be septic. Methods for determining which subjects are at risk of developing sepsis are well known to those in the art. Such subjects include, for example, those in an intensive care unit ("ICU") and those who have otherwise suffered from a physiological trauma, such as a burn, surgery or other insult. A hallmark of SIRS is the creation of a proinflammatory state that can be marked by tachycardia, tachypnea or hyperpnea, hypotension, hypoperfusion, oliguria, leukocytosis or leukopenia, pyrexia or hypothermia and the need for volume infusion. SIRS characteristically does not include a documented source of infection (e.g., bacteremia).

"Sepsis" refers to a systemic host response to infection with SIRS plus a documented infection (e.g., a subsequent laboratory confirmation of a clinically significant infection such as a positive culture for an organism). Thus, sepsis refers to the systemic inflammatory response to a documented infection (see, e.g., American College of Chest Physicians Society of Critical Care Medicine, Chest, 1997, 101:1644-1655, the entire contents of which are herein incorporated by reference). As used herein, "sepsis" includes all stages of sepsis including, but not limited to, the onset of sepsis, severe sepsis, septic shock and multiple organ dysfunction ("MOD") associated with the end stages of sepsis.

The "onset of sepsis" refers to an early stage of sepsis, e.g., prior to a stage when conventional clinical manifestations are sufficient to support a clinical suspicion of sepsis. Because the methods of the present invention can be used to detect sepsis prior to a time that sepsis would be suspected using conventional technique's, in certain embodiments, the subject's disease status at early sepsis is confirmed retrospectively, when the manifestation of sepsis is more clinically obvious. The exact mechanism by which a subject becomes septic is not a critical aspect of the invention. The methods of the present invention can detect the onset of sepsis independent of the origin of the infectious process.

"Severe sepsis" refers to sepsis associated with organ dysfunction, hypoperfusion abnormalities, or sepsis-induced hypotension. Hypoperfusion abnormalities include, but are not limited to, lactic acidosis, oliguria, or an acute alteration in mental status.

"Septic shock" refers to sepsis-induced hypotension that is not responsive to adequate intravenous fluid challenge and with manifestations of peripheral hypoperfusion.

A "converter" or "converter subject" refers to a SIRS-positive subject who progresses to clinical suspicion of sepsis during the period the subject is monitored, typically during an ICU stay.

A "non-converter" or "non-converter subject" refers to a SIRS-positive subject who does not progress to clinical suspicion of sepsis during the period the subject is monitored, typically during an ICU stay.

A "biomarker" is a compound that is present in or derived from a biological sample. "Derived from" as used in this context refers to a compound that, when detected, is indicative of a particular molecule being present in the biological sample. For example, detection of a particular fragment of a compound can be indicative of the presence of the compound itself in the biological sample. A biomarker can, for example, be isolated from the biological sample, directly measured in the biological sample, or detected in or determined to be in the biological sample. A biomarker can, for example, be functional, partially functional, or non-functional.

As used herein, "conventional techniques" in the context of the diagnosis or prognosis of a systemic inflammatory condition are those techniques that classify a subject based on phenotypic changes without evaluating a biomarker according to the present invention.

"Predicting the development of sepsis" is a determination as to whether subject develops sepsis. Such a prediction is limited by the accuracy of the means used to make this determination. The present invention provides a method, e.g., by utilizing a decision rule(s), for making this determination with an accuracy that is 60% or greater. As used herein, the terms "predicting the development of sepsis" and "predicting sepsis" are interchangeable. In some embodiments, the act of predicting the development of sepsis (predicting sepsis) is accomplished by evaluating one or more biomarker profiles from a subject using a decision rule that is indicative of the development of sepsis and, is a result of this evaluation, receiving a result from the decision rule that indicates that the subject will become septic. Such an evaluation of one or more biomarker profiles from a test subject using a decision rule uses some or all the amounts in the one or more biomarker profiles to obtain such a result.

As used herein, the term "specifically," and analogous terms, in the context of an antibody, refers to peptides, polypeptides, and antibodies or fragments thereof that specifically bind to an antigen or a class of antigens, or fragments thereof, and do not specifically bind to other antigens or other fragments. A peptide or polypeptide that specifically binds to an antigen may bind to other peptides or polypeptides with lower affinity, as determined by standard experimental techniques, for example, by any immunoassay well-known to those skilled in the art. Such immunoassays include, but are not limited to, radioimmunoassays (RIAs) and enzyme-linked immunosorbent assays (ELISAs). Antibodies or fragments that specifically bind to an antigen may be cross-reactive with related antigens. Preferably, antibodies or fragments thereof that specifically bind to an antigen do not cross-react with other antigens. See, e.g., Paul, ed., 2003, Fundamental Immunology, 5th ed., Raven Press, New York at pages 69-105, which is incorporated by reference herein, for a discussion regarding antigen-antibody interactions, specificity and cross-reactivity, and methods for determining all of the above.

As used herein, a "reference population" is a population of subjects that can be used to construct a decision rule for evaluation of a biomarker of subjects at risk for developing a systemic inflammatory condition.

A "reference subject" is a subject that has been diagnosed, or will be diagnosed within a defined period of time, with a systemic inflammatory condition according to standards recognized by those of skill in the art. A reference subject is useful for establishing a reference amount of the biomarker that can be used to evaluate an amount of the biomarker in a test subject for the diagnosis or prognosis of a systemic inflammatory condition.

A "biomarker profile" comprises a plurality of one or more types of biomarkers (e.g., a polypeptide, peptide, lipid, nucleic acid, metabolite, mRNA, cDNA, a and/or a carbohydrate, etc.), or an indication thereof, together with a feature, such as a measurable aspect (e.g., abundance, expression level) of the biomarkers. A biomarker profile comprises at least two such biomarkers or indications thereof, where the biomarkers can be in the same or different classes, such as, for example, a nucleic acid and a carbohydrate. A biomarker profile may also comprise at least three, four, five, 10, 20, 30 or more biomarkers or indications thereof. In one embodiment, a biomarker profile comprises hundreds, or even thousands, of biomarkers or indications thereof. A biomarker profile can further comprise one or more controls or internal standards. In one embodiment, the biomarker profile comprises at least one biomarker, or indication thereof, that serves as an internal standard. In another embodiment, a biomarker profile comprises an indication of one or more types of biomarkers. The term "indication" as used herein in this context merely refers to a situation where the biomarker profile contains symbols, data, abbreviations or other similar indicia for a biomarker, rather than the biomarker molecular entity itself.

Each biomarker in a biomarker profile includes a corresponding "feature." A "feature", as used herein, refers to a measurable aspect of a biomarker. A feature can include, for example, the presence or absence of the biomarker in the biological sample, the abundance or amount of the biomarker in the sample, the ratio of amounts of molecules in the sample, etc. A feature may also be the difference between a measurable aspect of the corresponding biomarker that is taken from two samples, where the two samples are collected from a subject at two different time points. Those of skill in the art will appreciate that other methods of computation of a feature can be devised and all such methods are within the scope of the present invention. For example, a feature can represent the average of an abundance of a biomarker across biological samples collected from a subject at two or more time points. Furthermore, a feature can be the difference or ratio of the abundance of two or more biomarkers from a biological sample obtained from a subject in a single time point. A biomarker profile may also comprise at least three, four, five, 10, 20, 30 or more features. In one embodiment, a biomarker profile comprises hundreds, or even thousands, of features.

A "phenotypic change" is a detectable change in a parameter associated with a given state of the subject. For instance, a phenotypic change can include an increase or decrease of a biomarker in a bodily fluid, where the change is associated with SIRS, sepsis, the onset of sepsis or with a particular stage in the progression of sepsis. A phenotypic change can further include a change in a detectable aspect of a given state of the subject that is not a change in a measurable aspect of a biomarker. For example, a change in phenotype can include a detectable change in body temperature, respiration rate, pulse, blood pressure, or other physiological parameter. Such changes can be determined via clinical observation and measurement using conventional techniques that are well-known to the skilled artisan.

A "decision rule" is a method used to evaluate biomarker profiles. Such decision rules can take on one or more forms that are known in the art, as exemplified in Hastie et al., 2001, *The Elements of Statistical Learning*, Springer-Verlag, New York, which is hereby incorporated by reference in its entirety. A decision rule may be used to act on a data set of features to, inter alia, predict the onset of sepsis, to determine the progression of sepsis, or to diagnose sepsis. Exemplary decision rules that can be used in some embodiments of the present invention are described in further detail in Section 5.5, below.

"Predicting the development of sepsis" is a determination as to whether subject develops sepsis. Such a prediction is limited by the accuracy of the means used to make this determination. The present invention provides a method, e.g., by utilizing a decision rule(s), for making this determination with an accuracy that is 60% or greater. As used herein, the terms "predicting the development of sepsis" and "predicting sepsis" are interchangeable. In some embodiments, the act of predicting the development of sepsis (predicting sepsis) is accomplished by evaluating one or more biomarker profiles from a subject using a decision rule that is indicative of the development of sepsis and, as a result of this evaluation, receiving a result from the decision rule that indicates that the subject will become septic. Such an evaluation of one or more biomarker profiles from a test subject using a decision rule uses some or all the features in the one or more biomarker profiles to obtain such a result.

As used herein, a "training population" is a set of samples from a population of subjects used to construct a decision rule, using a data analysis algorithm, for evaluation of the biomarker profiles of subjects at risk for developing sepsis. In a preferred embodiment, a training population includes samples from subjects that are converters and subjects that are nonconverters.

As used herein, a "data analysis algorithm" is an algorithm used to construct a decision rule using biomarker profiles of subjects in a training population. Representative data analysis algorithms are described in Section 5.5. A "decision rule" is the final product of a data analysis algorithm, and is characterized by one or more value sets, where each of these value sets is indicative of an aspect of SIRS, the onset of sepsis, sepsis, or a prediction that a subject will acquire sepsis. In one specific example, a value set represents a prediction that a subject will develop sepsis. In another example, a value set represents a prediction that a subject will not develop sepsis.

As used herein, a "value set" is a combination of values, or ranges of values for features in a biomarker profile. The nature of this value set and the values therein is dependent upon the type of features present in the biomarker profile and the data analysis algorithm used to construct the decision rule that dictates the value set. For example, a biomarker profile of each member of a training population can be obtained. Each such biomarker profile includes a measured feature for each biomarker. These feature values can be used by a data analysis algorithm to construct a decision rule. The data analysis algorithm can be a decision tree, described below. A decision rule defines value sets. One such value set is predictive of the onset of sepsis. A subject whose biomarker feature values satisfy this value set is likely to become septic. For example, a value set can comprise the amount of biomarker A being less than a first value and the amount of biomarker B being less than a second value. Another such value set is predictive of a septic-free state. A subject whose biomarker feature values satisfy this value set is not likely to become septic. An exemplary value set of this could comprise biomarker A being greater than the first value and biomarker B being greater than a third value.

Where the data analysis algorithm is a neural network analysis and the final product of this neural network analysis is an appropriately weighted neural network, one value set is those ranges of biomarker profile feature values that will cause the weighted neural network to indicate that onset of sepsis is likely. Another value set is those ranges of biomarker profile feature values that will cause the weighted neural network to indicate that onset of sepsis is not likely.

"Preventing" or "prevention" refers to a reduction in the risk of acquiring a disease or disorder (i.e., causing at least one of the clinical symptoms of the disease not to develop in a subject that may be exposed to or predisposed to the disease but does not yet experience or display symptoms of the disease). Preferably, prevention refers to the use of a compound or composition in a subject not yet affected by the disease or disorder or not yet exhibiting a symptom of the disease or disorder, for instance a subject not yet infected or not yet exhibiting the symptoms of infection.

"Treating" or "treatment" of any disease or disorder refers, in one embodiment, to ameliorating the disease or disorder (i.e., arresting or reducing the development of the disease or at least one of the clinical symptoms thereof) that exists in a subject. In another embodiment, "treating" or "treatment" refers to ameliorating at least one physical parameter, which may be indiscernible by the subject. In yet another embodiment, "treating" or "treatment" refers to modulating the disease or disorder, either physically (e.g., stabilization of a discernible symptom) or physiologically (e.g., stabilization of a physical parameter) or both. In yet another embodiment, "treating" or "treatment" refers to delaying the onset of the disease or disorder.

The term "label" refers to a display of written, printed or graphic matter upon the immediate container of an article, for example the written material displayed on a vial containing a pharmaceutically active agent.

The term "labeling" refers to all labels and other written, printed or graphic matter upon any article or any of its containers or wrappers or accompanying such article, for example, a package insert or instructional audios or videos, e.g. videotapes or DVDs, accompanying or associated with a container of a pharmaceutically active agent.

"Acyl" refers to a radical —C(O)R, where R is alkyl.

"Alkyl," by itself or as part of another substituent, means, unless otherwise stated, a straight or branched chain hydrocarbon radical which may be fully saturated, mono- or polyunsaturated, having the number of carbon atoms designated (i.e., $C_1$-$C_{22}$ means one to twenty-two carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Physiologically acceptable salt" refers to a salt of a compound of the invention that is pharmaceutically acceptable and that possesses the desired pharmacological activity of the parent compound. Such salts include: (1) acid addition salts formed with organic or inorganic acids such as hydrochloric, hydrobromic, sulfuric, nitric, phosphoric, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, and barium hydroxide, ammonia or (b) coordinates with an organic base, such as aliphatic, alicyclic, or aromatic organic amines, such as methylamine, dimethylaminem, diethylamine, picoline, ethanolamine, diethanolamine, triethanolamine, N-methylglucamine and the like.

Salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, acetate, maleate, oxalate and the like. The term "physiologically acceptable cation" refers to a non-toxic, physiologically acceptable cationic counterion of an acidic functional group. Such cations are exemplified by sodium, potassium, calcium, magnesium, ammonium and tetraalkylammonium cations and the like.

"Solvate" refers to a compound of the present invention or a salt thereof, that further includes a stoichiometric or non-stoichiometric amount of solvent bound by non-covalent intermolecular forces. Where the solvent is water, the solvate is a hydrate.

It is to be understood that compounds having the same molecular formula but differing in the nature or sequence of bonding of their atoms or in the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, when it is bonded to four different groups, a pair of enantiomers is possible. An enantiomer can be characterized by the absolute configuration of its asymmetric center and is designated (R) or (S) according to the rules of Cahn and Prelog (Calm et al., 1966, *Angew. Chem.* 78:413-447, *Angew. Chem., Int. Ed. Engl.* 5:385-414 (errata: *Angew. Chem., Int. Ed. Engl.* 5:511); Prelog and Helmchen, 1982, *Angew. Chem.* 94:614-631, *Angew. Chem. Internat. Ed. Eng.* 21:567-583; Mata and Lobo, 1993, *Tetrahedron: Asymmetry* 4:657-668) or can be characterized by the manner in which the molecule rotates the plane of polarized light and is designated dextrorotatory or levorotatory (i.e., as (+)- or (−)-isomers, respectively). A chiral compound can exist as either individual enantiomer or as a mixture thereof. A mixture containing equal proportions of enantiomers is called a "racemic mixture".

In certain embodiments, the compounds of this invention may possess one or more asymmetric centers; such compounds can therefore be produced as the individual (R)- or (S)-enantiomer or as a mixture thereof. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art. In particular embodiments, the present invention provides the stereoisomers of the compounds depicted herein upon treatment with base.

5.2 Embodiments of the Invention

The present invention allows for the rapid and accurate diagnosis or prognosis of a systemic inflammatory condition by evaluating lysophosphatidylcholine in a subject. Amounts of lysophosphatidylcholine can be constructed from one or more biological samples of subjects at a single time point ("snapshot"), or multiple such time points, during the course of time the subject is at risk for developing a systemic inflammatory condition. Advantageously, the systemic inflammatory condition can be diagnosed or predicted prior to the onset of conventional clinical symptoms, thereby allowing for more effective therapeutic intervention.

5.2.1. Subjects

In certain embodiments of the invention, the subject is an animal, preferably a mammal, more preferably a non-human primate. In the most preferred embodiments, the subject is a human.

Although the methods of the invention can used for the diagnosis or prognosis of a systemic inflammatory condition in any subject, particularly useful subjects include those that are at risk for the systemic inflammatory condition. The subject can be at risk for the systemic inflammatory condition according to any criteria known to the practitioner of skill in the art.

In certain embodiments, the subject is SIRS-negative. In the context of this invention, SIRS-negative subjects include healthy subjects that, for any reason according to the judgment of a practitioner of the art, are in need of diagnosis or prognosis of sepsis. Such subjects include, but are not limited to, SIRS-negative patients in hospital intensive care units and similarly situated subjects. The methods of the invention can be used for the diagnosis or prognosis of SIRS, sepsis, severe sepsis, septic shock, multiple organ dysfunction or mortality. Further methods of the invention can be used to monitor a treatment or prevention for increased or decreased risk of SIRS, sepsis, severe sepsis, septic shock, multiple organ dysfunction or mortality. In particular embodiments, the subject is a patient that might be at risk for a systemic inflammatory condition, such as a patient of an intensive care unit.

In further embodiments, the subject is SIRS-positive. The methods of the invention can be used for the diagnosis or prognosis of sepsis, severe sepsis, septic shock, multiple organ dysfunction or mortality, or they can be used for the diagnosis or prognosis of conversion to SIRS-negative. Further methods of the invention can be used to monitor a treatment or prevention for increased or decreased risk of sepsis, severe sepsis, septic shock, multiple organ dysfunction or mortality, or to monitor for possible conversion to SIRS-negative.

In further embodiments, the subject has sepsis. The methods of the invention can be used for the diagnosis or prognosis of severe sepsis, septic shock, multiple organ dysfunction or mortality, or they can be used for the diagnosis or prognosis of conversion to SIRS-positive (and sepsis-negative) or conversion to SIRS-negative. Further methods of the invention can be used to monitor a treatment or prevention for increased or decreased risk of severe sepsis, septic shock, multiple organ dysfunction or mortality, or to monitor for possible conversion to SIRS-positive (and sepsis-negative) or conversion to SIRS-negative.

In further embodiments, the subject has severe sepsis. The methods of the invention can be used for the diagnosis or prognosis of septic shock, multiple organ dysfunction or mortality, or they can be used for the diagnosis or prognosis of conversion to sepsis or to SIRS-positive (and sepsis-negative) or to SIRS-negative. Further methods of the invention can be used to monitor a treatment or prevention for increased or decreased risk of septic shock, multiple organ dysfunction or mortality, or to monitor for possible conversion to sepsis or to SIRS-positive (and sepsis-negative) or to SIRS-negative.

In further embodiments, the subject has septic shock. The methods of the invention can be used for the diagnosis or prognosis of multiple organ dysfunction or mortality, or they can be used for the diagnosis or prognosis of conversion to severe sepsis, to sepsis, to SIRS-positive (and sepsis-negative) or to SIRS-negative. Further methods of the invention can be used to monitor a treatment or prevention for increased or decreased risk of multiple organ dysfunction or mortality, or to monitor for possible conversion to severe sepsis, to sepsis, to SIRS-positive (and sepsis-negative) or to SIRS-negative.

In further embodiments, the subject has multiple organ dysfunction. The methods of the invention can be used for the diagnosis or prognosis of mortality, or they can be used for the diagnosis or prognosis of conversion to septic shock, severe sepsis, to sepsis, to SIRS-positive (and sepsis-negative) or to SIRS-negative. Further methods of the invention can be used to monitor a treatment or prevention for increased or decreased risk of mortality, or to monitor for possible conversion to septic shock, severe sepsis, to sepsis, to SIRS-positive (and sepsis-negative) or to SIRS-negative.

In preferred embodiments, the subject is SIRS-negative (i.e. the subject can be healthy) but in need of diagnosis or prognosis of a systemic inflammatory condition according to the judgment of a practitioner of skill in the art. The subject could be, for instance, a patient in an intensive care unit. Similarly, in preferred embodiments, subjects are SIRS-negative, and methods of the invention are used to monitor prevention of a systemic inflammatory condition. For instance, in a SIRS-negative subject judged to be at risk for a systemic inflammatory condition, for example according to a method of the invention, a course of intervention could be administered to the subject to prevent a systemic inflammatory condition. Such prevention of a systemic inflammatory condition can be monitored with a method of the invention.

In further preferred embodiments, subjects are SIRS-positive, and methods of the invention are used for the diagnosis or prognosis of a further systemic inflammatory condition. Similarly, in preferred embodiments, subjects are SIRS-positive, and methods of the invention are used to monitor treatment of SIRS or prevention of the further systemic inflammatory condition. For instance, in a SIRS-positive subject judged to be at risk for a further systemic inflammatory condition, for example according to a method of the invention, a course of intervention could be administered to the subject to prevent the systemic inflammatory condition. Such prevention of the systemic inflammatory condition can be monitored with a method of the invention.

In specific embodiments of the invention, subjects at risk for developing sepsis or SIRS are screened using the methods of the invention. In accordance with these embodiments, the methods of the present invention can be employed to screen, for example, subjects admitted to an intensive care unit and/or those who have experienced some sort of trauma (such as, e.g., surgery, vehicular accident, gunshot wound, etc.).

In specific embodiments, a subject is screened using the methods and compositions of the invention as frequently as necessary (e.g., during their stay in an intensive care unit) for the diagnosis or prognosis of a systemic inflammatory condition. In a preferred embodiment, the subject is screened soon after they arrive in an intensive care unit. In some embodiments, the subject is screened daily after they arrive in an intensive care unit. In some embodiments, the subject is screened every 1 to 8 hours, 8 to 12 hours, 12 to 16 hours, or 16 to 24 hours after they arrive in an intensive care unit.

5.3 Total Lysophosphatidylcholine

In one aspect, the present invention provides prognosis or diagnosis of a systemic inflammatory condition based on total lysophosphatidylcholine.

In certain embodiments, total lysophosphatidylcholine in a sample from a subject is used for the prognosis or diagnosis of the systemic inflammatory condition. Total lysophosphatidylcholine refers to an amount that corresponds to all lysophosphatidylcholine (free or bound or both) in the sample. For instance, total lysophosphatidylcholine can refer to those molecules in the sample that are according to formula (I):

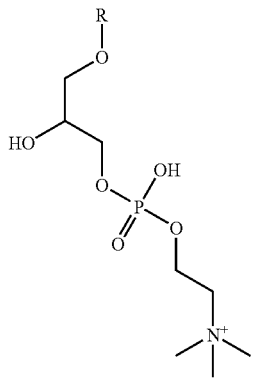

(I)

or any salt or solvate thereof, wherein R is any acyl group. The acyl group can be any acyl group known to those of skill in the art. Exemplary acyl groups include caproyl, lauroyl, myristoyl, palmitoyl, stearoyl, palmitoleyl, oleyl, arachidonyl and linoleyl. Preferably, total lysophosphatidylcholine includes at least 1-O-palmitoyl-2-lyso-sn-glycero-3-phosphocholine and 1-O-stearoyl-2-lyso-sn-glycero-3-phosphocholine. In typical embodiments, total lysophosphatidylcholine is measured without regard to the identity of the acyl group. Useful techniques are described herein.

In certain embodiments, total lysophosphatidylcholine alone is used for the prognosis or diagnosis of the systemic inflammatory condition. In further embodiments, one or more additional biomarkers are used for the prognosis or diagnosis of the systemic inflammatory condition. In further embodiments, one or more clinical measurements are additionally used for the prognosis or diagnosis of the systemic inflammatory condition. In certain embodiments, one or more additional biomarkers and one or more clinical measurements are additionally used for the prognosis or diagnosis of the systemic inflammatory condition.

The practitioner of skill can use any technique to measure or indicate total lysophosphatidylcholine in a sample. In certain embodiments, the practitioner of skill can measure an amount or value from a sample that correlates to total lysophosphatidylcholine. For instance, in certain samples from subjects, a fraction of total lysophosphatidylcholine can be free from other molecules while a further fraction of total lysophosphatidylcholine can be bound by other molecules. For example, a fraction of total lysophosphatidylcholine can be bound by albumin. The sample preparation and measurement techniques used by the practitioner of skill can affect the amount of lysophosphatidylcholine actually measured. For instance, precipitation and/or purification techniques car separate free and bound lysophosphatidylcholine. Detection techniques might be more sensitive to free lysophosphatidylcholine or to bound lysophosphatidylcholine. This amount measured can be correlated to the amount of total lysophosphatidylcholine in the sample according to methods available to the practitioner of skill. In certain embodiments, a measurement of free lysophosphatidylcholine is used to indicate the amount of total lysophosphatidylcholine in the sample. In certain embodiments, a measurement of bound lysophosphatidylcholine is used to indicate the amount of total lysophosphatidylcholine in the sample. In certain embodiments, a measurement of bound and free lysophosphatidylcholine is used to indicate the amount of total lysophosphatidylcholine in the sample. In certain embodiments, free lysophosphatidylcholine can be used for prognosis or diagnosis in the methods of the invention. In certain embodiments, bound lysophosphatidylcholine can be used for prognosis or diagnosis in the methods of the invention. In certain embodiments, free and bound lysophosphatidylcholine can be used for prognosis or diagnosis in the methods of the invention.

Each additional biomarker can be of any type of biomarker for a systemic inflammatory condition known to those of skill in the an including protein, peptide, nucleic acid, lipid, phospholipid and metabolite (e.g., protein, peptide, nucleic acid, nucleoside, lipid or phospholipid metabolite) biomarkers. Further exemplary biomarkers for the prognosis or diagnosis of a systemic inflammatory condition, and methods of their evaluation, are described in U.S. Patent Application Publication Nos. 20030194752, 20040096917, 20040097460, 20040106142, 20040157242, and U.S. Provisional Application Nos. 60/671,620, filed Apr. 15, 2005, 60/671,941, filed Apr. 15, 2005, and 60/674,046, filed Apr. 22, 2005, the contents of which are hereby incorporated by reference in their entireties. Further exemplary biomarkers for sepsis include endotoxin; bacterial DNA; acute phase proteins such as protein C, procalcitonin, LBP-LPS-binding protein; coagulation factors such as fibrin degrading products, antithrombin III, dimer D; membrane cell markers such as HLA-DR, CD-64, E-selectin; hormones such as cortisol. ACTH; soluble receptors such as CD-14, sTNFRI, sTNF-RII; and cytokines such as TNF, IL-6, IL-8 and IL-10; and others such as D-dimer, prothrombin time, activated partial thromboplastin time, plasminogen activator inhibitor-1, soluble thrombomodulin, IL-6, IL-10, IL-8, protein C, thrombin activatable fibrinolysis inhibitor, protein S, antithrombin, TNF-α. See, e.g., Kinasewitz et al., 2004, *Critical Care* 8:R82-R90, Bozza et al., 2005, *Mem. Inst. Oswaldo Cruz* 100(s)1:217-221, the contents of which are hereby incorporated by reference in their entireties. Preferred biomarkers include C-reactive protein, procalcitonin and IL-6.

In certain embodiments, the present invention provides methods of evaluating a panel of biomarkers from a subject for diagnosis or prognosis of a systemic inflammatory condition. The panel can comprise any number of biomarkers sufficient to make a diagnosis or prognosis of the systemic inflammatory condition according to the judgment of one of skill in the art. The panel should comprise total lysophosphatidylcholine. The panel can additionally comprise other biomarkers for the systemic inflammatory condition, including those described in the paragraph above. In some embodiments, the panel comprises 2, 3, 4, 5, 6, 7, 8, 9, 10, 15, 20 or 25 or more biomarkers for the systemic inflammatory condition. Each biomarker should be evaluated by techniques appropriate for the class of biomarker. Exemplary techniques are described herein, and other techniques should be apparent to those of skill in the art. In convenient embodiments, biomarkers of the same class, or biomarkers that can be evaluated by the same technique, can be evaluated together in the panel. For instance, in a particular embodiment, metabolite and/or protein biomarkers can be evaluated by immunoassay techniques in an array or chip format, as described below.

The clinical measurement for the systemic inflammatory condition can be any clinical measurement for the systemic inflammatory condition known to those of skill in the art. In certain embodiments, the clinical measurement is according to a clinical severity model for sepsis. Such models include, but are not limited to, the Acute Physiology and Chronic Health Evaluation score (APACHE, and its refinements APACHE II and III) (Knaus et al., 1985, *Crit. Care Med* 13: 818-829; Knaus et al., 1991, *Chest* 100: 1619-1636), the Mortality Prediction Model (MPM) (Lemeshow et al., 1993, *JAMA* 270: 2957-2963), the Simplified Acute Physiology (SAPS) score (Le Gall et al., 1984, *Crit. Care Med* 12: 975-977), the Multiple Organ Dysfunction Score (MODS) (Marshall et al., 1995, *Crit. Care Med* 23: 1638-1652), the Sequential Organ Failure Assessment (SOFA) score (Ferreira et al., 2002, *JAMA* 286: 1754-1758), the Logistical Organ Dysfunction Score (LODS) (Le Gall et al., 1996, *JAMA* 276: 802-810) and the predisposition, infection, response, and organ dysfunction (PIRO) concept (Levy et al., 2003, *Intensive Care Med* 29: 530-538) (the contents of each reference is hereby incorporated in its entirety). In certain embodiments, the clinical measurement comprises one or more measurements used by those of skill in the art to aid in the prognosis or diagnosis of sepsis. Such measurements include, but are not limited to, temperature, heart rate, white blood cell count, differential white blood cell count (monocytes, lymphocytes, granulocytes and/or neutrophils), immature neutrophil to total neutrophil ratio, platelet count, serum creatinine, urea, lactate, base excess, $pO_2$ and $HCO_3^-$.

5.4 Biomarker

In another aspect, the present invention provides prognosis or diagnosis of a systemic inflammatory condition with a lysophosphatidylcholine biomarker of the invention.

In certain embodiments, the biomarker is a 1-O-acyl-2-lyso-sn-glycero-3-phosphocholine. For instance, in certain embodiments the biomarker is a compound according to formula (I):

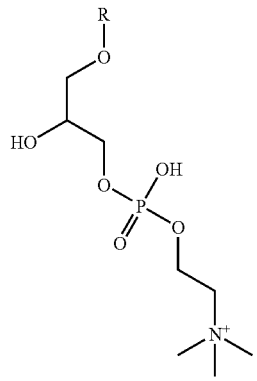

(I)

or any salt or solvate thereof, wherein R is an acyl group.

Exemplary salts of formula (I) are provided by formula (Ia):

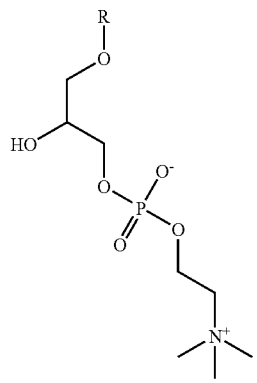

(Ia)

wherein said salt can be coordinated with any ion or ions known to those of skill in the art. The ion or ions can be physiological but need not be physiological. For instance, the ion or ion can result from contact with the salt during the preparation of the sample from the subject, as described below. In some embodiments, the salt is coordinated with an anion, for instance, a physiological anion known to those of skill in the art. Exemplary anions include chloride, bromide, phosphate, acetate, carbonate, bicarbonate and sulfate. In some embodiments, the salt is coordinated with a cation, for instance, a physiological cation, known to those of skill in the art. Exemplary cations include sodium, potassium, calcium, magnesium and ammonium. In some embodiments, as skill be recognized by those of skill in the art, the salt is coordinated with one or more anions and with one or more cations.

The acyl group can be any acyl group known to those of skill in the art. In certain embodiments the acyl group is saturated. Exemplary saturated acyl groups include caproyl, lauroyl, myristoyl, palmitoyl and stearoyl. In further embodiments, the acyl group is monounsaturated. Exemplary monounsaturated acyl groups include palmitoleyl and oleyl. In further embodiments, the acyl group is polyunsaturated. Exemplary polyunsaturated acyl groups include arachidonyl and linoleyl.

More systematically, in certain embodiments, the acyl group is $C_{10}$-$C_{22}$ acyl. In certain embodiments, the acyl group is $C_{14}$-$C_{22}$ acyl. Exemplary acyl groups include 16:0, 18:0, 18:1, 18:2, 20:4(n-6) and 22:6(n-3), according to nomenclature familiar to those of skill in the art. In such nomenclature, the first number indicates the number of carbon atoms in the acyl group, and the second number indicates the number of double bonds in the group. For instance, "18:1" indicates an acyl group with 18 carbon atoms and one double bond. Numbers in parentheses, if any, indicate the location of the double bond, and the notation "(n-x)" indicates a double bond x positions away from the terminal methyl of the longest chain of the fatty acid. See *Biochem. J.,* 1978, 171, 21-35; *Chem. Phys. Lipids,* 1978, 21, 159-173; *Eur. J. Biochem.,* 1977, 79, 11-21; *Hoppe-Seyler's Z. Physiol. Chem.,* 1977, 358, 617-631; *J. Lipid Res.,* 1978, 19, 114-128; Lipids, 1977, 12, 455-468; *Mol. Cell. Biochem.,* 1977, 17, 157-171; *Biochemical Nomenclature and Related Documents,* 2nd edition, Portland Press, 1992, pages 180-190, the contents of which are hereby incorporated by reference in their entireties.

In certain embodiments, the acyl group is $C_{14}$-$C_{22}$ acyl. In certain embodiments, the acyl group is $C_{16}$-$C_{20}$ acyl. In further embodiments, the acyl group is $C_{16}$-$C_{18}$ acyl. In certain embodiments, the acyl group is hexadecanoyl or octadecanoyl. In particular embodiments, the acyl group is $C_{16}$ acyl. In a preferred embodiment, the acyl group is hexadecanoyl. In further particular embodiments, the acyl group is $C_{18}$ acyl. In a preferred embodiment, the acyl group is octadecanoyl.

The biomarker can be any form of the biomarker from the subject, for instance any salt or solvate of the biomarker that can be identified by those of skill in the art. In preferred embodiments, the biomarker is in the form of a sodium salt.

In certain embodiments, the biomarker is a metabolite of a compound according to formula (I). For instance, the biomarker can be a precursor of a compound according to formula (I) known to those of skill in the art. The precursor can be one or two or three, or in some embodiments more, steps prior to the compound according to formula (I) in a biosynthetic pathway known to those of skill in the art. In further embodiments, the biomarker can be a downstream metabolite of a compound according to formula (I) in a biosynthetic pathway known to those of skill in the art. Me downstream metabolite can be one or two or three, or in some embodiments more, steps following the compound according to formula (I) in a biosynthetic pathway known to those of skill in the art. In certain embodiments, the biosynthetic pathway is a de novo pathway for the synthesis of platelet activating factor known to those of skill in the art. In further embodiments, the biosynthetic pathway is a remodeling pathway for the synthesis of platelet activating factor known to those of skill in the art.

In particular embodiments, the metabolite is a 1-O-acyl-2-O-acyl-sn-glycero-3-phosphocholine. In preferred embodiments, the 2-O-acyl group is any acyl group described above or acetyl. In particular embodiments, the metabolite is a 1-O-acyl-2-O-alkyl-sn-glycero-3-phosphocholine. In preferred embodiments, the 2-O-alkyl group is any group known to those of skill in the art to modify a glycero-3-phosphocholine, for instance any $C_{14}$-$C_{22}$ alkyl.

In certain embodiments, a single biomarker is used for the prognosis or diagnosis of the systemic inflammatory condition. In further embodiments, a plurality of biomarkers are used for the prognosis or diagnosis of the systemic inflammatory condition. The biomarkers in the plurality can be according to the invention as described above, or the plurality can comprise biomarkers according to the invention along with further biomarkers for the diagnosis or prognosis of a systemic inflammatory condition known to those of skill in the art. The biomarker can be of any type of biomarker for a systemic inflammatory condition known to those of skill in the art including protein, peptide, nucleic acid, lipid, phospholipid and metabolite (e.g., protein, peptide, nucleic acid, nucleoside, lipid or phospholipid metabolite) biomarkers.

Further exemplary biomarkers for the prognosis or diagnosis of a systemic inflammatory condition, and methods of their evaluation, are described in U.S. Patent Application Publication Nos. 20030194752, 20040096917, 20040097460, 20040106142, 20040157242, and U.S. Provisional Application Nos. 60/671,620, filed Apr. 15, 2005, 60/671,941, filed Apr. 15, 2005, and 60/674,046, filed Apr. 22, 2005, the contents of which are hereby incorporated by reference in their entireties. Further exemplary biomarkers for sepsis include endotoxin; bacterial DNA; acute phase proteins such as protein C, procalcitonin, LBP-LPS-binding protein; coagulation factors such as fibrin degrading products, antithrombin III, dimer D; membrane cell markers such as HLA-DR, CD-64, E-selectin; hormones such as cortisol, ACTH; soluble receptors such as CD-14, sTNFRI, sTNF-RII; and cytokines such as TNF, IL-6, IL-8 and IL-10; and others such as D-dimer, prothrombin time, activated partial thromboplastin time, plasminogen activator inhibitor-1, soluble thrombomodulin, IL-6, IL-10, IL-8, protein C, thrombin activatable fibrinolysis inhibitor, protein S, antithrombin, TNF-α. See, e.g., Kinasewitz et al., 2004, *Critical Care* 8:R82-R90, Bozza et al., 2005, *Mem. Inst. Oswaldo Cruz* 100(s)1: 217-221, the contents of which are hereby incorporated by reference in their entireties. Preferred biomarkers include C-reactive protein, procalcitonin and IL-6.

In certain embodiments, the present invention provides methods of evaluating a panel of biomarkers from a subject for diagnosis or prognosis of a systemic inflammatory condition. The panel can comprise any number of biomarkers sufficient to make a diagnosis or prognosis of the systemic inflammatory condition according to the judgment of one of skill in the art. The panel should comprise one or more biomarkers of the invention, for example, a biomarker according to formula I or formula Ia. The panel can additionally comprise other biomarkers for the systemic inflammatory condition, including those described in the paragraph above. In some embodiments, the panel comprises 2, 3, 4, 5, 6, 7, 8, 9, 10, 15, 20 or 25 or more biomarkers for the systemic inflammatory condition. Each biomarker should be evaluated by techniques appropriate for the class of biomarker. Exemplary techniques are described herein, and other techniques should be apparent to those of skill in the art. In convenient embodiments, biomarkers of the same class, or biomarkers that can be evaluated by the same technique, can be evaluated together in the panel. For instance, in a particular embodiment, metabolite and/or protein biomarkers can be evaluated by immunoassay techniques in an array or chip format, as described below.

5.5 Measurement of the Lysophosphatidylcholine

In this section and the sections that follow, unless specified otherwise, the term lysophosphatidylcholine refers to total lysophosphatidylcholine or to a lysophosphatidylcholine biomarker of the invention.

In certain embodiments of the invention, the method of measuring lysophosphatidylcholine is not critical. Accordingly, the present invention provides methods for the diagnosis or prognosis of a systemic inflammatory condition that comprise the single step of assessing risk for the systemic inflammatory condition from lysophosphatidylcholine.

Total lysophosphatidylcholine can be measured by one practicing a method of the invention in any manner whatsoever. Exemplary techniques are described herein. As described above, any technique that indicates lysophosphatidylcholine in the sample can be used in the methods of the invention. In certain embodiments, the methods are based on free lysophosphatidylcholine in the sample. In certain embodiments, the methods are based on bound lysophosphatidylcholine in the sample. In certain embodiments, the methods are based on free and bound lysophosphatidylcholine in the sample.

The amount of a lysophosphatidylcholine biomarker can be measured by one practicing a method of the invention in any manner whatsoever. Exemplary techniques are described herein.

When a plurality or panel of biomarkers is to be evaluated, each individual biomarker should be evaluated according to a technique suitable for that biomarker. In advantageous embodiments, biomarkers that can be evaluated by the same or by compatible techniques can be evaluated together. For instance, protein, peptide, lipid, phospholipid and metabolite biomarkers that can be evaluated by immunoassays can be evaluated together or in groups according to techniques known to those of skill in the art.

In one embodiment, only a single biological sample taken at a single point in time from the subject is used to make a prognosis or diagnosis of sepsis. In another embodiment, a plurality of biological samples taken at different points in time from the subject are used to make a prognosis or diagnosis of sepsis.

In a specific embodiment, the amount of lysophosphatidylcholine is obtained using samples collected from the subject at one time point. In another specific embodiment, the amount of lysophosphatidylcholine is obtained using samples obtained from the subject at separate time points. In one example, these samples are obtained from the subject either once or, alternatively, on a daily basis, or more frequently, e.g., every 2, 3, 4, 6, 8 or 12 hours.

Lysophosphatidylcholine can be obtained from any biological sample, which can be, by way of example and not of limitation, blood, plasma, serum, saliva, sputum, urine, cerebral spinal fluid, cells, a cellular extract, a tissue sample, a tissue biopsy, a stool sample or any sample that may be obtained from a subject using techniques well known to those of skill in the art. The precise biological sample that is taken from the subject may vary, but the sampling preferably is minimally invasive and is easily performed by conventional techniques.

The biological sample can be processed or purified according to the judgment of those of skill in the art based on, for example, the type of biomarker and the measurement technique. For instance, when the biomarker is a lipid or phospholipid metabolite, the sample can be processed by extraction and/or chromatography. When the biomarker is a protein or peptide, for example when a panel of biomarkers is to be evaluated, the sample can be processed by precipitation, centrifugation, filtration and/or chromatography. When the biomarker is a nucleic acid, for example when a panel of biomarkers is to be evaluated, the sample can be processed to isolate nucleic acids by extraction, precipitation and/or chromatography.

Some portion of the mixture of peptides, proteins, nucleic acids, phospholipids, and metabolites (for instance, metabolites or peptides, proteins, phospholipids or nucleosides) and/or other molecules of the sample can then be resolved as a biomarker profile. This can be accomplished by measuring amounts of the biomarkers in the biomarker profile. A biomarker profile comprises a plurality of one or more types of biomarkers (e.g., a phospholipid, an mRNA, a cDNA, a protein and/or a carbohydrate, etc.), or an indication thereof, together with amounts of the biomarkers. A biomarker profile can comprise at least one such biomarker or indication thereof. Multiple biomarkers can be in the same or different classes, such as, for example, phospholipid and a polypeptide.

These amounts can be determined through the use of any reproducible measurement technique or combination of measurement techniques. Such techniques include those that are well known in the art including any technique described herein. Typically, such techniques are used to measure amounts using a biological sample taken from a subject at a single point in time or multiple samples taken at multiple points in time. In a preferred embodiment, an exemplary technique to obtain a biomarker profile from a sample taken from a subject is immunoassay. Biomarker profiles can be generated using a kit, such as a kit described below.

In certain embodiments, methods of detection of the biomarker involve their detection via interaction with a biomarker-specific antibody. For example, antibodies directed to the biomarker of the invention. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used.

For example, antibodies, or fragments of antibodies, specific for a biomarker can be used to quantitatively or qualitatively detect the presence of a biomarker. This can be accomplished, for example, by immunofluorescence techniques. Antibodies (or fragments thereof) can, additionally, be employed histologically, as in immunofluorescence or immunoelectron microscopy, for in situ detection of a biomarker. In situ detection can be accomplished by removing a biological sample (e.g., a biopsy specimen) from a patient, and applying thereto a labeled antibody that is directed to a biomarker. The antibody (or fragment) is preferably applied by overlaying the antibody (or fragment) onto a biological sample. Through the use of such a procedure, it is possible to determine not only the presence of the biomarker, but also its distribution, in a particular sample. A wide variety of well-known histological methods (such as staining procedures) can be utilized to achieve such in situ detection.

Immunoassays for a biomarker typically comprise incubating a biological sample of a detectably labeled antibody capable of identifying a biomarker, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a biomarker can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a biomarker through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}I$, $^{131}I$, $^{35}S$ or $^{3}H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In advantageous embodiments, the antibodies can be in the form of an array. Such an array can be used for the measurement or detection of a plurality or panel of biomarkers simultaneously. The array can be any array for antibodies known to those of skill in the art. In certain embodiments, a plurality of antibodies can be in the form of an antibody chip for the detection of a plurality or panel of biomarkers. Exemplary antibody arrays and antibody chips are described in U.S. Patent Application Publication Nos. 20050048566, 20050054015, 20050037343, 20050095591, 20050100947, 20040161748, 20040097460, and 20040096917, the contents of which are hereby incorporated by reference in their entireties. Commercial antibody arrays can be used or adapted for the present invention, including, but not limited to, those available from Whatman Schliecher & Schuell, Eurogentec, Sigma Aldrich, Novagen and Chemicon International. Binding of antigen to antibody can proceed according to techniques suitable for the antibody array or antibody chip, including, but not limited to, fluorescence, surface plasmon resonance and mass spectrometry.

In another embodiment, specific binding molecules other than antibodies, such as aptamers, may be used to bind the biomarkers. In yet another embodiment, the biomarker profile may comprise a measurable aspect of an infectious agent (e.g., lipopolysaccharides or viral proteins) or a component thereof.

Amounts of biomarkers in a biomarker profile can also, for example, be generated by the use of one or more of the following methods described below. For example, methods may include nuclear magnetic resonance (NMR) spectroscopy, a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

In one embodiment, laser desorption/ionization time-of-flight mass spectrometry is used to determine the amount of a biomarker where the biomarker is a molecule that has been ionized and vaporized off an immobilizing support by incident laser radiation. A variety of laser desorption/ionization techniques are known in the art (see, e.g., Guttman et al., 2001, Anal. Chem. 73:1252-62 and Wei et al., 1999, Nature 399:243-246, which are hereby incorporated by reference).

Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 µL, with or without prior purification or fractionation. The lysates or sample can be concentrated or diluted prior to application onto the support surface. Laser desorption/ionization is then used to generate mass spectra of the sample, or samples, in as little as three hours.

Analysis by liquid chromatography-mass spectrometry produces a mass intensity spectrum, the peaks of which represent various components of the sample, each component having a characteristic mass-to-charge ratio (m/z) and retention time (r.t.). The presence of a peak with the m/z and retention time of a biomarker indicates that the marker is present. The peak representing a marker may be compared to a corresponding peak from another spectrum (e.g., from a control sample) to obtain a relative measurement. Any normalization technique in the art (e.g., an internal standard) may be used when a quantitative measurement is desired. In addition, deconvoluting software is available to separate overlapping peaks. The retention time depends to some degree on the conditions employed in performing the liquid chromatography separation.

In MALDI mass spectrometry (MALDI-MS), various mass analyzers can be used, e.g., magnetic sector/magnetic deflection instruments in single or triple quadrupole mode (MS/MS), Fourier transform and time of flight (TOF), including orthogonal time-of-flight (O-TOF), configurations as is known in the art of mass spectrometry. For the desorption/ionization process, numerous matrix/laser combinations can be used. Lontrap and reflectron configurations also can be employed.

Electrospray ionization mass spectrometry (ESI-MS) is broadly applicable for analysis of macromolecules, including proteins, nucleic acids, and carbohydrates (Fenn et al., 1989, *Science* 246:64-71; Crain et al., 1998, *Curr. Opin. Biotechnol.* 9:25-34; Smith et al., 1990, *Anal Chem.* 62:882-99; Han & Gross, 1994, *Proc Natl Acad Sci USA* 91: 10635-10639). Electrospray techniques have been used to separate and measure biomarkers like those of formula I and formula Ia (see Petkovic et al., 2001, *Anal Biochem.* 289(2):202-16; Pulfer & Murphy, 2003, Mass Spec Rev 22:332-364; Han & Gross, 1995, *J. Amer. Soc. Mass Spec.* 6:1202-1210; the contents of which are hereby incorporated by reference in their entireties).

For the following classes of metabolites, the following sources provide additional guidance on mass spectral analysis of such molecules and are incorporated by reference in their entirety: (1) lipids (see, e.g., Fenselau, C., *ACS Symp. Ser.*, 541:1-7 (1994)); (2) volatile metabolites (see, e.g., Lauritsen and Lloyd, D., *ACS Symp Ser.* 541:91-106 (1994)); (3) carbohydrates (see, e.g., Fox and Black, *ACS Symp. Ser.* 541: 107-131 (1994); (4) nucleic acids (see, e.g., Edmonds et al., *ACS Symp. Ser.*, 541:147-158 (1994); and (5) proteins (see, e.g., Vorm, O. et al., *Anal. Chem.* 66:3281-3287 (1994); and Vorm and Mann, *J. Am. Soc. Mass. Spectrom.* 5:955-958 (1994)). The contents of these publications are hereby incorporated by reference in their entireties.

In certain embodiments, species in the biological sample can be separated by liquid chromatography in conjunction with any of the mass spectrometry techniques described above. Such liquid chromatography/mass spectrometry techniques have proven useful for the separation of biomarkers such as proteins, peptides, nucleic acids, lipids, phospholipids and metabolites. For instance, since sensitive separation of phospholipid species has been achieved with LC/MS (see Kim et al., 1994, *Anal Chem.* 66(22):3977-82; Ma & Kim, 1995, *Anal Biochem.* 226(2):293-301; the contents of which are hereby incorporated by reference in their entireties), such techniques can be used to separate and measure a biomarker according to formula I or formula Ia.

In specific embodiments of the invention, biomarkers in a biomarker plurality or panel are nucleic acids. Such biomarkers and corresponding amounts of the biomarker profile may be generated, for example, by detecting the expression product (e.g., a polynucleotide or polypeptide) of one or more genes described herein. In a specific embodiment, the biomarkers and corresponding amounts in a biomarker profile are obtained by detecting and/or analyzing one or more nucleic acids using any method well known to those skilled in the art including, but by no means limited to, hybridization, microarray analysis, RT-PCR, nuclease protection assays and Northern blot analysis. As will be recognized by those of skill in the art, in convenient embodiments, the biological sample can be split, with one portion evaluated for nucleic acid biomarkers, and another portion evaluated for other biomarkers such as proteins, peptides, lipids, phospholipids and metabolites. In fact, the biological sample can be divided as many times as desired by the practitioner of skill to facilitate evaluation or measurement of each biomarker in a plurality or panel of biomarkers.

In certain embodiments of the invention, nucleic acid arrays are employed to generate amounts of biomarkers in a biomarker profile by detecting the expression of any one or more of the genes described herein. In one embodiment of the invention, a microarray, such as a cDNA microarray, is used to determine amounts of biomarkers in a biomarker profile. The diagnostic use of cDNA arrays is well known in the art. (See, e.g., Zou et. al., 2002, *Oncogene* 21:4855-4862; as well as Draghici, 2003, *Data Analysis Tools for DNA Microarrays*, Chapman & Hall/CRC, each of which is hereby incorporated by reference in its entirety). Exemplary methods for cDNA microarray analysis are described below, and in the examples in Section 6, infra.

In certain embodiments, the amounts for biomarkers in a biomarker profile are obtained by hybridizing to the array detectably labeled nucleic acids representing or corresponding to the nucleic acid sequences in mRNA transcripts present in a biological sample (e.g., fluorescently labeled cDNA synthesized from the sample) to a microarray comprising one or more probe spots.

Nucleic acid arrays, for example, microarrays, can be made in a number of ways, of which several are described herein below. Preferably, the arrays are reproducible, allowing multiple copies of a given array to be produced and results from said microarrays compared with each other. Preferably, the arrays are made from materials that are stable under binding (e.g., nucleic acid hybridization) conditions. Those skilled in the art will know of suitable supports, substrates or carriers for hybridizing test probes to probe spots on an array, or will be able to ascertain the same by use of routine experimentation.

Several chromatographic techniques may be used to separate biomarkers. For example, amplification products may be separated by agarose, agarose-acrylamide or polyacrylamide gel electrophoresis using conventional methods. See Sambrook et al., 2001. Several techniques for detecting biomarkers quantitatively without electrophoresis may also be used according to the invention (see, e.g., *PCR Protocols, A Guide to Methods and Applications*, Innis et al., 1990, Academic Press, Inc. N.Y., which is hereby incorporated by reference). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, *Physical Biochemistry Applications to Biochemistry and Molecular Biology*, 2nd ed., Wm. Freeman and Co., New York, N.Y., 1982, which is hereby incorporated by reference).

In certain embodiments, one or more of the biomarkers is a protein. In a specific embodiment, a biomarker profile is generated by detecting and/or analyzing one or more proteins and/or discriminating fragments thereof using any method known to those skilled in the art for detecting proteins including, but not limited to, protein microarray analysis, immunohistochemistry and mass spectrometry.

Standard techniques may be utilized for determining the amount of the protein or proteins of interest present in a sample. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired a protein from the sample to be analyzed can easily be isolated using techniques which are well known to those of skill in the art. Protein isolation methods can, for example, be such as those described in Harlow and Lane, 1988, *Antibodies: A Laboratory Manual*. Cold Spring Harbor Laboratory Press (Cold Spring Harbor, N.Y.), which is incorporated by reference herein in its entirety.

In certain embodiments, methods of detection of the protein or proteins of interest involve their detection via interaction with a protein-specific antibody. For example, antibodies directed to a protein of interest. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used. Exemplary immunoassays are described above.

In some embodiments, a protein chip assay (see, e.g., Zhu & Snyder, 2003, *Curr. Opin. Chem. Biol.* 7:55-63; Mitchell, 2002, *Nature Biotechnology* 20:225-229) is used to measure amounts for the biomarkers in the biomarker profile. See also, for example, Lin, 2004, *Modern Pathology*, 1-9; Li, 2004, *Journal of Urology* 171, 1782-1787; Wadsworth, 2004, *Clinical Cancer Research*, 10, 1625-1632; Prieto, 2003, *Journal of Liquid Chromatography & Related Technologies* 26, 2315-2323; Coombes, 2003, *Clinical Chemistry* 49, 1615-1623; Mian, 2003, *Proteomics* 3, 1725-1737; Lehre et al., 2003, *BJU International* 92, 223-225; and Diamond, 2003, *Journal of the American Society for Mass Spectrometry* 14, 760-765, which are hereby incorporated by reference in their entireties. Particularly useful in certain embodiments of the invention are antibody chips that facilitate detection by MALDI or SELDI (see, e.g, Wang, et al., 2001, *Int'l. J. of Cancer* 92:871-876; Figeys, 2002, *Proteomics* 2:373-382; Sonksen et al., 1998, *Anal. Chem.* 70:2731-6; Glökler, & Angenendt, 2003, *J. Chromatography B*, 797:229-240; the contents of which are hereby incorporated by reference in their entireties).

5.5.1. Antibodies Selective for Biomarkers of the Invention

Antibodies to the biomarkers of the invention can be produced or obtained according to any technique apparent to those of skill in the art. For instance, antibodies to phospholipids and metabolites of the invention can be prepared or isolated according to the techniques described in Mourdjeva et al., 2005 *Apoptosis* 10(1):209-17, von Landenberg et al., 1999, *J Autoimmun.* 13:215-23, or Menon et al., *J Autoimmun.* 10:43-57, the contents of which are hereby incorporated by reference in their entireties. Antibodies to polypeptides, or metabolites thereof, can be prepared according to standard techniques.

An isolated phospholipid of the invention, or a metabolite or fragment thereof, can be used as an immunogen to generate antibodies using standard techniques for polyclonal and monoclonal antibody preparation. An immunogen typically is used to prepare antibodies by immunizing a suitable subject, (e.g., rabbit, goat, mouse or other mammal). An appropriate immunogenic preparation can comprise, for example, recombinantly expressed or chemically synthesized polypeptide. The preparation can further include an adjuvant, such as Freud's complete or incomplete adjuvant, or similar immunostimulatory agent. In certain embodiments, to facilitate antibody production the phospholipid of the invention, or a metabolite or fragment thereof, can be coupled to a carrier, for instance a protein such as keyhole limpet hemacyanin, bovine serum albumin, thyroglobulin, and ovalbumin.

Polyclonal antibodies can be prepared by immunizing a suitable subject with a phospholipid of the invention, or a metabolite or fragment thereof, of the invention as an immunogen. The antibody titer in the immunized subject can be monitored over time by standard techniques, such as with an enzyme linked immunosorbent assay (ELISA) using immobilized polypeptide. If desired, the antibody molecules can be isolated from the subject (e.g., from the blood) and further purified by well-known techniques, such as protein A chromatography to obtain the IgG fraction. Alternatively, antibodies specific for a phospholipid of the invention, or a metabolite or fragment thereof, of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample comprising antibodies directed against a large number of different epitopes, thereby generating a substantially purified antibody composition, i.e., one that is substantially free of contaminating antibodies. By a substantially purified antibody composition is meant, in this context, that the antibody sample comprises at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975, *Nature* 256:495-497), the human B cell hybridoma technique (Kozbor et al., 1983, *Immunol Today* 4:72), the EBV-hybridoma technique (Cole et al., 1985, in *Monoclonal Antibodies and Cancer Therapy*, Alan R. Liss, Inc., pp. 77-96) or trioma techniques. The technology for producing hybridomas is well known (See, e.g., *Current Protocols in Immunology*, Coligan et al. (eds.) John Wiley & Sons, Inc., New York, N.Y. (1994)). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phase Antibody System, Catalog No. 27-9400-01; and the Stratagene SurfZAP Phage Display Kit, Catalog No. 240612). Additionally, examples of methods and reagents particularly amenable for use in generating and screening an antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, *BioTechnology* 9:1370-1372; Hay et al., 1992, *Hum Antibod Hybridomas* 3:81-85; Huse et al., 1989, *Science* 246: 1275-1281; Griffiths et al., 1993, *EMBO J.* 12:725-74.

Additionally, recombinant antibodies, such as chimeric and humanized monoclonal antibodies, comprising both human and nonhuman portions, which can be made using standard recombinant DNA techniques, are within the scope of the invention. A chimeric antibody is a molecule in which different portions are derived from different animal species, such as those having a variable region derived from a murine mAb and a human immunoglobulin constant region (see, e.g., Cabilly et al., U.S. Pat. No. 4,816,567; and Boss et al., U.S.

Pat. No. 4,816,397, which are incorporated herein by reference in their entirety). Humanized antibodies are antibody molecules from non-human species having one or more complementarity determining regions (CDRs) from the non-human species and a framework region from a human immunoglobulin molecule (see, e.g., Queen, U.S. Pat. No. 5,585,089, which is incorporated herein by reference in its entirety). Such chimeric and humanized monoclonal antibodies can be produced by recombinant DNA techniques known in the art, for example using methods described in PCT Publication No. WO 87/02671; European Patent Application 184,187; European Patent Application. 171,496; European Patent Application 173,494; PCT Publication No. WO 86/01533; U.S. Pat. No. 4,816,567; European Patent Application 125,023; Better et al., 1988, Science 240:1041-1043; Liu et al., 1987, Proc Natl Acad. Sci. 84:3439-3443; Liu et al., 1987, J. Immunol. 139:3521-3526; Sun et al., 1987, Proc Natl Acad. Sci. 84:214-218; Nishimura et al., 1987, Cancer Res. 47:999-1005; Wood et al., 1985, Nature 314:446-449; and Shaw et al., 1988, J. Natl. Cancer Inst. 80:1553-1559; Morrison, 1985, Science 229:1202-1207: Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1994, BioTechnology 12:899-903).

5.5.2. Enzymatic Assays for Biomarkers of the Invention

In advantageous embodiments, total lysophosphatidylcholine can be detected, measured or monitored by one or more enzymatic assays. The enzymatic assays can be any enzymatic assays known to those of skill in the art to be useful for detecting, measuring or monitoring one or more of the biomarkers of the invention.

In certain embodiments, the enzymatic assays can be according to published application JP 2002-17938 (Kishimoto et al., 2002, Method of Measuring Phospholipid), or according to Kishimoto et al., 2002, Clinical Biochem. 35:411-416, the contents of which are hereby incorporated by reference in their entireties.

In certain embodiments, total lysophosphatidylcholine can be measured by contacting a sample of the invention with an enzyme capable of hydrolyzing lysophosphatidylcholine to yield glycerophosphorylcholine. The enzyme can be any such enzyme known to those of skill in the art. Exemplary enzymes include lysophospholipases such as EC 3.1.1.5 (commercially available from, e.g., Asahi Chemical Co.). In certain embodiments, the lysophospholipase preferentially hydrolyzes lysophospholipids relative to other phospholipids. In certain embodiments, the lysophospholipase is from Bacillus. In certain embodiments, the lysophospholipase is according to JP 2002-17938.

The resulting glycerophosphorylcholine can be detected, measured or monitored according to any technique apparent to those of skill in the art. For instance, in certain embodiments, the glycerophosphorylcholine can be contacted with a glycerophosphorylcholine diesterase known to those of skill in the art (e.g. EC 3.1.4.2) under conditions suitable to yield choline. The resulting choline can be contacted with a choline oxidase known to those of skill in the art (e.g. EC 1.1.3.17) under conditions suitable to yield peroxide. Use of the choline oxidase enables the method to detect lysophosphatidylcholine in preference to other lysophospholipids such as lysophospholipids comprising serine or ethanolamine. The resulting peroxide can be detected by any technique apparent to those of skill in the art including, for example, colorimetric techniques.

The detection of hydrogen peroxide can be accomplished by any technique apparent to one of skill in the art. Exemplary techniques include chemiluminescence (Kiba et al., 2003, Analytical Science 19(6):823-827), fluorescence (Zhang et al., 199, Talanta 48(5):1031-1038; Chen et al., 2001, Analytica Chimica 434(1):51-58), and spectrophotometry (Pappas et al., 2002, Analytica Chimica 455(2):305-313). Other exemplary techniques include metal complexes (Paleologos, 2002, Analytical Chemistry 74(1):100-106) as well as redox mediated electrochemical detection (e.g., commercially available glucose meters).

In advantageous embodiments, peroxidase activity can be detected with a fluorogenic substrate. Such embodiments provide rapid and sensitive techniques for the detection of total lysophosphatidylcholine in the sample. These techniques thus provide rapid and sensitive assays for the diagnosis or prognosis of a systemic inflammatory condition as described herein. The fluorogenic substrate can be any fluorogenic substrate known to those of skill in the art to be capable of conversion to a fluorescent product by a peroxidase in the presence of peroxide under suitable conditions, e.g. with water and oxygen. In particular embodiments, the fluorogenic substrate is 10-acetyl-3,7-dihydroxyphenoxazine. This substrate can be obtained from commercial suppliers (e.g. Amplex Red, Invitrogen). Those of skill in the art will recognize that this fluorogenic substrate can be converted to the fluorescent product 7-hydroxy-3H-phenoxazin-3-one (resorufin), detectable by techniques apparent to those of skill in the art. Useful detection techniques include, of course, fluorescence detection. Preferably, the detection methods are carried out under conditions in which the product can be formed and detected. Useful conditions and results are described in the working examples below.

In certain embodiments, the glycerophosphorylcholine can be contacted with a glycerophosphorylcholine phosphodiesterase known to those of skill in the art under conditions suitable to yield glycerol-3-phosphate. The resulting glycerol-3-phosphate can be contacted with a glycerol-3-phosphate oxidase known to those of skill in the art under conditions suitable to yield peroxide. Useful glycerol-3-phosphate oxidases include those derived from *Streptococcus, Aerococcus*, and *Pediococcus*, and those described in JP 2002-17938. The resulting peroxide can be detected by any technique apparent to those of skill in the art including, for example, colorimetric techniques.

In certain embodiments, the glycerophosphorylcholine can be contacted with a glycerophosphorylcholine phosphodiesterase known to those of skill in the art under conditions suitable to yield glycerol-3-phosphate. The resulting glycerol-3-phosphate can be contacted with a glycerol-3-phosphate dehydrogenase known to those of skill in the art under conditions suitable to yield a detectable product. For instance, the contacting can be in the presence of $NAD^+$ to yield detectable NADH. The contacting can also be in the presence of $NADP^+$ to yield detectable NADPH.

Techniques for detecting, measuring or monitoring detectable products such as peroxide, NADH and NADPH are well known to those of skill in the art. Useful techniques are described in JP 2002-17938, Misaki, 1999, *Modern Medical Laboratory* 27(8): 973-980, (1999), Japanese Patent No. 1594750, Japanese Patent Laid-Open No. 05-229993, and Aoyama, 1997, *Journal of Medical Technology* 14: 1014-1019, the contents of which are hereby incorporated by reference in their entireties.

5.6 Diagnosis or Prognosis of the Systemic Inflammatory Condition

In certain methods of the invention, total lysophosphatidylcholine in the subject is used for the diagnosis or prognosis of the systemic inflammatory condition. As described above, total lysophosphatidylcholine can be measured directly, or a measurement can be made that correlates to the amount of total lysophosphatidylcholine. In certain embodiments, free lysophosphatidylcholine is measured. In certain embodiments, bound lysophosphatidylcholine is measured. In certain embodiments, free lysophosphatidylcholine and bound lysophosphatidylcholine are measured.

In certain methods of the invention, the amount of one or more lysophosphatidylcholine biomarkers in the subject is used for the diagnosis or prognosis of the systemic inflammatory condition.

In certain methods of the invention, the amount of total lysophosphatidylcholine and one or more lysophosphatidylcholine biomarkers in the subject are used for the diagnosis or prognosis of the systemic inflammatory condition.

In some embodiments, a single sample from the subject is sufficient for diagnosis or prognosis of the systemic inflammatory condition. In such embodiments, the amount of lysophosphatidylcholine can be compared to an internal reference in the biological sample that is present at a relatively constant amount in individuals similar to the subject. The internal reference can be any reference judged suitable to one of skill in the art and is preferably not related to the biomarker or to systemic inflammatory conditions. In certain embodiments, the internal reference is phosphatidylcholine, phosphatidylethanolamine or phosphatidylserine.

In some embodiments, a plurality of biological samples from the subject are evaluated for the diagnosis or prognosis of the systemic inflammatory condition. In such embodiments, change in the amount of lysophosphatidylcholine is indicative of risk for the systemic inflammatory condition.

In certain embodiments, increasing amounts of lysophosphatidylcholine indicate a decreasing risk for a systemic inflammatory condition. For instance, in certain embodiments, a second amount that is at least 110%, 125%, 150%, 175%, 200%, 300%, 400% or 500% of a previous amount indicates decreased risk for the systemic inflammatory condition.

In certain embodiments, decreasing amounts of lysophosphatidylcholine indicated an increasing risk for a systemic inflammatory condition. For instance, in certain embodiments, a second amount that is less than 95%, 90%, 80%, 75%, 50%, 33%, 25%, 20% or 10% of a previous amount indicates decreased risk for the systemic inflammatory condition.

In certain embodiments, diagnosis or prognosis of the systemic inflammatory condition can be based on a comparison of the amount of lysophosphatidylcholine in a sample of the subject to a reference amount of lysophosphatidylcholine. Reference amounts are described in the section below. Significantly, the amount of the reference amount need not be obtained or measured by a practitioner of a method of the invention. Instead, the reference amount can be identified by consultation of amounts of the reference in reference populations available to those of skill in the art. Such amounts can be published, for example, in scientific literature on electronic databases.

In preferred embodiments, the reference amount is measured by the same technique or a comparable technique used to measure the amount in the sample. For instance, preferably, if free lysophosphatidylcholine is measured in the sample, the reference amount can be based on free lysophosphatidylcholine in a reference subject or a reference population. For instance, preferably, if bound lysophosphatidylcholine is measured in the sample, the reference amount can be based on bound lysophosphatidylcholine. Of course, if total lysophosphatidylcholine and the reference amount are measured by different techniques, correlation of the two amounts should be within the ability of the practitioner of skill.

If a lysophosphatidylcholine biomarker is measured in the sample, the reference amount can be based on the lysophosphatidylcholine biomarker in a reference subject or reference population. Of course, if the lysophosphatidylcholine biomarker and the reference amount are measured by different techniques, correlation of the two amounts should be within the ability of the practitioner of skill When a reference amount is used, the difference between the reference amount and the amount in the test subject is used by a practitioner of skill in the art to make a diagnosis or prognosis of the systemic inflammatory condition. In certain embodiments, if the amount in the test subject is between 10-190%, 20-180%, 30-170%, 40-160%, 50-150%, 75-125%, 80-120%, 90-110% or 95-105% of the reference amount, diagnosis or prognosis of the systemic inflammatory condition is indicated.

If a cutoff reference amount is used, the difference between the cutoff and the amount in the test subject is used by a practitioner of skill in the art to make a diagnosis or prognosis of the systemic inflammatory condition. In certain embodiments, if the amount in the test subject is below, or substantially below, the cutoff reference amount, diagnosis or prognosis of the systemic inflammatory condition is indicated, and if the amount in the test subject is above, or substantially above, the cutoff reference amount, no diagnosis or prognosis of the systemic inflammatory condition would be indicated.

In certain embodiments, the difference between the amount of lysophosphatidylcholine in the test subject and the reference amount correlates inversely with risk for the systemic inflammatory condition. Such correlation can be determined by those of skill in the art.

When reference amounts from a plurality of reference subjects are used, the evaluation can be based on any statistical technique known to those of skill in the art. Similarly, when a plurality of biomarkers are used, the diagnosis or prognosis can be based on the plurality of amounts according to techniques known to those of skill in the art, such as those described in U.S. Patent Application Publication Nos. 20030194752, 20040096917, 20040097460, 20040106142, 20040157242, and U.S. Provisional Application Nos. 60/671,620, filed Apr. 15, 2005, 60/671,941, filed Apr. 15, 2005, and 60/674,046, filed Apr. 22, 2005, the contents of which are hereby incorporated by reference in their entireties.

5.7 Reference Biomarker

In certain methods of the invention, the amount of total lysophosphatidylcholine of the subject is compared to a corresponding reference amount of total lysophosphatidylcholine. The reference amount is typically the amount of total lysophosphatidylcholine in a reference subject (not the subject of the method) that has, or will have within a defined period of time, a known systemic inflammatory condition. While not intending to be bound by any particular theory of operation, the present invention is based, in part, on the discovery of a correlation between total lysophosphatidylcholine and a systemic inflammatory condition in a subject. Accordingly, one practicing a method of the invention can compare the amount of total lysophosphatidylcholine in a subject to a reference amount of total lysophosphatidylcholine in order to make a prognosis or diagnosis of the systemic inflammatory condition.

In certain methods of the invention, the amount of the lysophosphatidylcholine biomarker of the subject is compared to a corresponding reference amount of the biomarker. The reference amount is typically the amount of the same biomarker, or a derivative thereof, in a reference subject (not the subject of the method) that has, or will have within a defined period of time, a known systemic inflammatory condition. While not intending to be bound by any particular theory of operation, the present invention is based, in part, on the discovery of a correlation between a lysophosphatidylcholine biomarker of the invention and a systemic inflammatory condition in a subject. Accordingly, one practicing a method of the invention can compare the amount of a lysophosphatidylcholine biomarker in a subject to a reference amount of the lysophosphatidylcholine biomarker in order to make a prognosis or diagnosis of the systemic inflammatory condition.

Advantageously, in order to practice methods of the invention, one need not gather reference amounts of lysophosphatidylcholine in reference populations. Such reference amounts can be identified in sources available to those of skill in the art, such as public or private databases, or by reference to the data provided herein. As such, in the methods that use a reference amount of lysophosphatidylcholine, one need only make the comparison described in the method.

A reference amount can be measured according to techniques known to those of skill in the art including those described herein. Advantageously, in certain embodiments, the amount of lysophosphatidylcholine in the reference subject and the amount of lysophosphatidylcholine in the test subject are obtained by the same technique.

The reference subject can be any subject that presents, or that will present within a defined period of time, symptoms of the systemic inflammatory condition according to one of skill in the art. In certain embodiments, the reference amount is obtained at a time when the reference subject is presenting the symptoms. In certain embodiments, the reference amount can be obtained at a time before or a time after the reference subject presents symptoms of, or is diagnosed with, the systemic inflammatory condition. For instance, in certain embodiments, reference amounts are obtained from reference subjects 48, 36, 24 or 12 hours prior to the onset of sepsis. Those of skill in the art will recognize that such amounts can be obtained by measuring amounts in a reference population at risk for sepsis and following the diagnoses of the reference subject over time.

The reference subject can have any systemic inflammatory condition or can be free of a systemic inflammatory condition. In certain embodiments, the reference subject can be SIRS-negative or present symptoms of SIRS, sepsis, severe sepsis, septic shock, multiple organ dysfunction or mortality. Such reference amounts can be used for the diagnosis or prognosis of the condition.

Methods for the diagnosis of the systemic inflammatory condition are to be carried out according to the knowledge of those of skill the art. Such methods are routine and will not be described herein.

In certain embodiments, the diagnosis or prognosis of a systemic inflammatory condition is based on a cutoff reference amount. A cutoff reference amount is an absolute value for the amount that indicates risk for the systemic inflammatory condition. For instance, a cutoff reference amount of 100 for a biomarker of the invention can indicate risk for a systemic inflammatory condition when the test subject has an amount of the biomarker that is less than 100 (or greater than 100 in alternative embodiments). Cutoff reference amounts can be determined using statistical techniques known to those of skill in the art based on reference amounts obtained from reference subjects. For instance, a cutoff for a particular systemic inflammatory condition can be determined so that a new reference subject can have a diagnosis or prognosis within a confidence interval suitable to those of skill in the art, for instance with 60%, 70%, 80%, 85%, 90%, 95% or 99% confidence.

5.8 Methods of Monitoring Treatment or Prevention of Systemic Inflammatory Conditions In certain aspects, the present invention provides methods of monitoring a systemic inflammatory condition, or risk for the systemic inflammatory condition, in a subject in need thereof. In certain embodiments, the amount of lysophosphatidylcholine is obtained from the subject and used to assess the condition or risk for the condition.

In particular embodiments, the present invention provides methods of monitoring a treatment of a systemic inflammatory condition. The methods of the invention can be used to assess the effectiveness of the treatment and alter the treatment depending on the results of the method. Such methods generally comprise the step of measuring the amount of lysophosphatidylcholine to assess risk for a systemic inflammatory condition in a subject that has been, or will be, administered a treatment or prevent on of a systemic inflammatory condition.

In certain embodiments, the present invention provides methods of monitoring a treatment or prevention of SIRS, sepsis, severe sepsis, septic shock, multiple organ dysfunction or mortality. The treatment or prevention can be any treatment or prevention of SIRS, sepsis, severe sepsis, septic shock, multiple organ dysfunction or mortality known to those of skill.

In certain embodiments, the treatment or prevention comprises administration of antibiotics according to techniques known to those of skill. The antibiotic can be any antibiotic suitable for the treatment or prevention of the systemic inflammatory condition known to those of skill in the art. In some embodiments, the antibiotic can be effective against gram-positive bacteria such as gentamycin, ceftriaxone, tobramycin or ceftazidine. In some embodiments, the antibiotic can be effective against gram-negative bacteria such as vancomycin. In some embodiments, the antibiotic can be effective against anaerobic bacteria, such as metrionidazole.

In further embodiments, the treatment or prevention comprises administration of steroid according to techniques known to those of skill. The steroid can be any steroid suitable for the treatment or prevention of the systemic inflammatory condition known to those of skill in the art. In certain embodiments, the steroid is hydrocortisone or dexamethasone.

In further embodiments, the treatment or prevention comprises administration of a vasopressor or inotropic therapy according to techniques known to those of skill. The vasopressor or inotropic therapy can be any vasopressor or inotropic therapy suitable for the treatment or prevention of the systemic inflammatory condition known to those of skill in the art. In certain embodiments, the vasopressor or inotropic therapy is norepinephrine, dopamine or dobutaime.

In further embodiments, the treatment or prevention comprises administration of XIGRIS® (drotrecogin alfa (activated), Eli Lilly and Company). XIGRIS® is a recombinant form of human activated protein C approved by the United States Food and Drug Administration for the reduction of mortality in adult patients with severe sepsis.

In particular embodiments, the present invention provides methods of treating or preventing a systemic inflammatory condition. The methods comprise the steps of administering a treatment or prevention of the systemic inflammatory condition and monitoring risk or severity of the systemic inflammatory condition according to a method of the invention. Risk or severity of the systemic inflammatory condition can be assessed according to the methods described herein. In certain embodiments, further administration of the treatment or prevention can be adjusted based on a result of the monitoring according to the judgment of one of skill in the art.

In an embodiment, the present invention provides a method of treating or preventing a systemic inflammatory condition in a subject in need thereof comprising the steps of administering to the subject an effective amount of XIGRIS® and monitoring the systemic inflammatory condition according to a method of the invention. In certain embodiments, the systemic inflammatory condition is sepsis or severe sepsis.

In some embodiments, a plurality of amounts of lysophosphatidylcholine are obtained over time to monitor the systemic inflammatory condition. In certain embodiments, increasing amounts indicate decreased risk of the systemic inflammatory condition or decreased severity of the condition. For instance, in certain embodiments, a second amount that is at least 110%, 125%, 150%, 175%, 200%, 300%, 400% or 500% of a previous amount indicates decreased risk for the systemic inflammatory condition or decreased severity of the condition. In further embodiments, decreasing amounts indicate increased risk of the systemic inflammatory condition or increased severity of the condition. For instance, in certain embodiments, a second amount that is less than 95%, 90%, 80%, 75%, 50%, 33%, 25%, 20% or 10% of a previous amount indicates increased risk for the systemic inflammatory condition or increased severity of the condition.

In some embodiments, one or more amounts are obtained over time. In such embodiments, the difference between the amount of lysophosphatidylcholine and a reference amount of total lysophosphatidylcholine for a systemic inflammatory condition is used for diagnosis or prognosis of the systemic inflammatory condition. Comparison to the reference amount can be carried out as described above.

5.9 Kits for the Diagnosis or Prognosis, or Monitoring, of a Systemic Inflammatory Condition The invention also provides kits that are useful for the diagnosis or prognosis, or monitoring, of a systemic inflammatory condition in a subject. In some embodiments, the kits of the present invention comprise a reagent that specifically binds total lysophosphatidylcholine. The reagent may be part of an array, or the reagent may be packaged separately and/or individually. The kit may also comprise at least one internal standard to be used in evaluating total lysophosphatidylcholine. In particular embodiments, the kits comprise an array of antibodies or a chip of antibodies with specificity for one or more biomarkers in a plurality or panel of biomarkers of the invention.

The kits of the present invention may contain reagents that can be used to detect biomarkers contained in the biological samples from which the biomarker profiles are generated. In a specific embodiment, the invention provides a kit for predicting the development of sepsis in a test subject comprises an antibody that specifically binds total lysophosphatidylcholine. In accordance with this embodiment, the kit may comprise an antibody or functional fragment or derivative thereof (e.g., Fab, F(ab')$_2$, Fv, or scFv fragments) that preferentially binds total lysophosphatidylcholine. In certain embodiments, the antibodies may be detectably labeled.

In certain embodiments the kits comprise reagents useful for the detection of total lysophosphatidylcholine in a sample. In certain embodiments, the reagents comprise one or more enzymes and one or more substrates useful for detection of lysophosphatidylcholine. In particular embodiments, the kits can comprise a fluorogenic substrate useful for detection of total lysophosphatidylcholine. Certain kits comprise an enzyme or reagent capable of reacting lysophosphatidylcholine to form glycerophosphatidylcholine under suitable conditions, an enzyme or reagent capable of reacting glycerophosphatidylcholine to form choline under suitable conditions, an enzyme or reagent capable of reacting choline to form peroxide under suitable conditions, a peroxidase and a fluorogenic substrate of said peroxidase. Certain kits comprise a lysophospholipase, a glycerophosphatidylcholine diesterase, a choline oxidase, a peroxidase and 10-acetyl-3, 7-dihydroxyphenoxazine. Certain kits comprise EC 3.1.1.5, EC 3.1.4.2, EC 1.1.3.17, horseradish peroxidase and 10-acetyl-3,7-dihydroxyphenoxazine. The kits can further comprise one or more reference standards for evaluating the total lysophosphatidylcholine according to methods of the invention.

The invention also provides kits that are useful for the diagnosis or prognosis, or monitoring, of a systemic inflammatory condition in a subject. In some embodiments, the kits of the present invention comprise a reagent that specifically binds a biomarker of the present invention. The reagent may be part of an array, or the reagent may be packaged separately and/or individually. The kit may also comprise at least one internal standard to be used in evaluating a biomarker of the present invention. In particular embodiments, the kits comprise an array of antibodies or a chip of antibodies with specificity for one or more biomarkers in a plurality or panel of biomarkers of the invention.

The kits of the present invention may contain reagents that can be used to detect biomarkers contained in the biological samples from which the biomarker profiles are generated. In a specific embodiment, the invention provides a kit for predicting the development of sepsis in a test subject comprises an antibody that specifically binds a biomarker of the invention. In accordance with this embodiment, the kit may comprise an antibodies or functional fragment or derivative thereof (e.g., Fab, F(ab')$_2$, Fv, or scFv fragments) that specifically bind one or more of the biomarker of the invention. In certain embodiments, the antibodies may be detectably labeled.

In other embodiments of the invention, a kit may comprise a specific biomarker binding reagent, such as an aptamer. If the biomarkers comprise a nucleic acid, the kit may provide an oligonucleotide probe that is capable of forming a duplex with the biomarker or with a complementary strand of a biomarker. The oligonucleotide probe may be detectably labeled.

The kits of the present invention may also include reagents such as buffers, or other reagents that can be used in obtaining an amount of the biomarker. Prevention of the action of microorganisms can be ensured by the inclusion of various antibacterial and antifungal agents, for example, paraben, chlorobutanol, phenol sorbic acid, and the like. It may also be desirable to include isotonic agents such as sugars, sodium chloride, and the like.

In embodiments that use biomarkers in addition to lysophosphatidylcholine, such as nucleic acid biomarkers, the kits can advantageously comprise a microarray. In one embodiment this microarray comprises a plurality of probe spots for biomarkers to be evaluated with the kit. In some embodiments, the microarray consists of between about three and about one hundred probe spots on a substrate. In some embodiments, the microarray consists of between about three and about one hundred probe spots on a substrate. As used in this context, the term "about" means within five percent of the stated value, within ten percent of the stated value, or within twenty-five percent of the stated value.

In certain embodiments, the kits further comprise a label or labeling with instructions for carrying out a method of the invention. For example, the label or labeling can provide a reference amount or reference amounts of lysophosphatidylcholine corresponding to one or more systemic inflammatory conditions. The label or labeling can provide one or more cutoff reference amounts of lysophosphatidylcholine corresponding to one or more systemic inflammatory conditions. Further, the label or labeling can provide citations or links to sources of such reference amounts.

Some kits of the invention may further comprise a computer program product for use in conjunction with a computer system, wherein the computer program product comprises a computer readable storage medium and a computer program mechanism embedded therein. In such kits, the computer program mechanism comprises instructions for evaluating whether a one or more amounts of lysophosphatidylcholine of a test subject at risk for developing a systemic inflammatory condition satisfies a first value set. Satisfying the first value set predicts that the test subject is likely to develop the systemic inflammatory condition. In some kits, the computer program product further comprises instructions for evaluating whether the one or more amounts of lysophosphatidylcholine of the test subject satisfies a second value set. Satisfying the second value set predicts that the test subject is not likely to develop the systemic inflammatory condition.

5.10 Algorithms for the Diagnosis or Prognosis, or Monitoring, of a Systemic Inflammatory Condition The present invention provides total lysophosphatidylcholine and lysophosphatidylcholine biomarkers useful for the diagnosis, prognosis and monitoring of a systemic inflammatory condition. As described above, the lysophosphatidylcholine can be used alone or as part of a plurality or panel of biomarkers. A plurality or panel of biomarkers can comprise a lysophosphatidylcholine of the invention, biomarkers known to those of skill in the art to be useful, or both. In advantageous embodiments, these biomarkers are capable of discriminating between converters and nonconverters.

The identity of these biomarkers and their corresponding features (e.g., amount or expression values) can be used to develop a decision rule, or plurality of decision rules, that discriminate between converters and nonconverters. Data analysis algorithms can be used to construct a number of such decision rules. Data analysis algorithms use features (e.g., amount or expression values) of a subset of the biomarkers of the present invention across a training population that includes converters and nonconverters. Typically, a SIRS subject is considered a nonconverter when the subject does not develop sepsis in a defined time period (e.g., observation period). This defined time period can be, for example, twelve hours, twenty four hours, forty-eight hours, a day, a week, a month, or longer. Specific data analysis algorithms for building a decision rule, or plurality of decision rules, that discriminate between subjects that develop sepsis and subjects that do not develop sepsis during a defined period will be described in the subsections below. Once a decision rule has been built using these exemplary data analysis algorithms or other techniques known in the art, the decision rule can be used to classify a test subject into one of the two or more phenotypic classes (e.g., a converter or a nonconverter). This is accomplished by applying the decision rule to a biomarker profile obtained from the test subject. Such decision rules, therefore, have value as diagnostic indicators.

The present invention provides, in one aspect, for the evaluation of a biomarker profile from a test subject to biomarker profiles obtained from a training population. In some embodiments, each biomarker profile obtained from subjects in the training population, as well as the test subject, comprises a feature for each of a plurality of different biomarkers. In some embodiments, this comparison is accomplished by (i) developing a decision rule using the biomarker profiles from the training population and (ii) applying the decision rule to the biomarker profile from the test subject. As such, the decision rules applied in some embodiments of the present invention are used to determine whether a test subject having SIRS will or will not likely acquire sepsis.

In some embodiments of the present invention, when the results of the application of a decision rule indicate that the subject will likely acquire sepsis, the subject is diagnosed as a "sepsis" subject. If the results of an application of a decision rule indicate that the subject will not acquire sepsis, the subject is diagnosed as a "SIRS" subject. Thus, in some embodiments, the result in the above-described binary decision situation has four possible outcomes:

truly septic, where the decision rule indicates that the subject will acquire sepsis and the subject does in fact acquire sepsis during the definite time period (true positive, TP);

(ii) falsely septic, where the decision rule indicates that the subject will acquire sepsis and the subject, in fact, does not acquire sepsis during the definite time period (false positive, FP);

(iii) truly SIRS, where the decision rule indicates that the subject will not acquire sepsis and the subject, in fact, does not acquire sepsis during the definite time period (true negative, TN); or (iv) falsely SIRS, where the decision rule indicates that the subject will not acquire sepsis and the subject, in fact, does acquire sepsis during the definite time period (false negative, FN).

It will be appreciated that other definitions for TP, FP, TN, FN can be made. For example, TP could have been defined as instances where the decision rule indicates that the subject will not acquire sepsis and the subject, in fact, does not acquire sepsis during the definite time period. While all such alternative definitions are within the scope of the present invention, for ease of understanding the present invention, the definitions for TP, FP, TN, and FN given by definitions (i) through (iv) above will be used herein, unless otherwise stated.

As will be appreciated by those of skill in the art, a number of quantitative criteria can be used to communicate the performance of the comparisons made between a test biomarker profile and reference biomarker profiles (e.g., the application of a decision rule to the biomarker profile from a test subject). These include positive predicted value (PPV), negative predicted value (NPV), specificity, sensitivity, accuracy, and certainty. In addition, other constructs such a receiver operator curves (ROC) can be used to evaluate decision rule performance. As used herein:

PPV=TP/(TP+FP)
NPV=TN/(TN+FN)
specificity=TN/(TN+FP)
sensitivity=TP/(TP+FN)
accuracy=certainty=(TN+TP)/N Here, N is the number of samples compared (e.g., the number of test samples for which a determination of sepsis or SIRS is sought). For example, consider the case in which there are ten subjects for which SIRS/sepsis classification is sought. Biomarker profiles are constructed for each of the ten test subjects. Then, each of the biomarker profiles is evaluated by applying a decision rule, where the decision rule was developed based upon biomarker profiles obtained from a training population. In this example, N, from the above equations, is equal to 10. Typically, N is a number of samples, where each sample was collected from a different member of a population. This population can, in fact, be of two different types. In one type, the population comprises subjects whose samples and phenotypic data (e.g., feature values of biomarkers and an indication of whether or not the subject acquired sepsis) was used to construct or refine a decision rule. Such a population is referred to herein as a training population. In the other type, the population comprises subjects that were not used to construct the decision rule. Such a population is referred to herein as a validation population. Unless otherwise stated, the population represented by N is either exclusively a training population or exclusively a validation population, as opposed to a mixture of the two population types. It will be appreciated that scores such as accuracy will be higher (closer to unity) when they are based on a training population as opposed to a validation population. Nevertheless, unless otherwise explicitly stated herein, all criteria used to assess the performance of a decision rule (or other forms of evaluation of a biomarker profile from a test subject) including certainty (accuracy) refer to criteria that were measured by applying the decision rule corresponding to the criteria to either a training population or a validation population. Furthermore, the definitions for PPV, NPV, specificity, sensitivity, and accuracy defined above can also be found in Draghici, *Data Analysis Tools for DNA Microanalysis*, 2003, CRC Press LLC, Boca Raton, Fla., pp. 342-343, which is hereby incorporated by reference.

In some embodiments the training population comprises nonconverters and converters. In some embodiments, biomarker profiles are constructed from this population using biological samples collected from the training population at some time period prior to the onset of sepsis by the converters of the population. As such, for the converters of the training population, a biological sample can be collected two week before, one week before, four days before, three days before, one day before, or any other time period before the converters became septic. In practice, such collections are obtained by collecting a biological sample at regular time intervals after admittance into the hospital with a SIRS diagnosis. For example, in one approach, subjects who have been diagnosed with SIRS in a hospital are used as a training population. Once admitted to the hospital with SIRS, the biological samples are collected from the subjects at selected times (e.g., hourly, every eight hours, every twelve hours, daily, etc.). A portion of the subjects acquire sepsis and a portion of the subjects do not acquire sepsis. For the subjects that acquire sepsis, the biological sample taken from the subjects just prior to the onset of sepsis are termed the $T_{-12}$ biological samples. All other biological samples from the subjects are retroactively indexed relative to these biological samples. For instance, when a biological sample has been taken from a subject on a daily basis, the biological sample taken the day before the $T_{-12}$ sample is referred to as the $T_{-36}$ biological sample. Time points for biological samples for a nonconverter in the training population are identified by "time-matching" the nonconverter subject with a converter subject. To illustrate, consider the case in which a subject in the training population became clinically-defined as septic on his sixth day of enrollment. For the sake of illustration, for this subject, $T_{-36}$ is day four of the study, and the $T_{-36}$ biological sample is the biological sample that was obtained on day four of the study. Likewise, $T_{-36}$ for the matched nonconverter subject is deemed to be day four of the study on this paired nonconverter subject.

In some embodiments, N is more than one, more than five, more than ten, more than twenty, between ten and 100, more than 100, or less than 1000 subjects. A decision rule (or other forms of comparison) can have at least about 99% certainty, or even more, in some embodiments, against a training population or a validation population. In other embodiments, the certainty is at least about 97%, at least about 95%, at least about 90%, at least about 85%, at least about 80%, at least about 75%, or at least about 70% against a training population or a validation population. The useful degree of certainty may vary, depending on the particular method of the present invention. As used herein, "certainty" means "accuracy." In one embodiment, the sensitivity and/or specificity is at is at least about 97%, at least about 95%, at least about 90%, at least about 85%, at least about 80%, at least about 75%, or at least about 70% against a training population or a validation population. The number of features that may be used by a decision rule to classify a test subject with adequate certainty is typically about four. Depending on the degree of certainty sought, however, the number of features used in a decision rule can be more less, but in all cases is at least two. In one embodiment, the number of features that may be used by a decision rule to classify a test subject is optimized to allow a classification of a test subject with high certainty.

In the examples below, metabolite abundance data was collected for a plurality of biomarkers in each subject. That is, for each biomarker in a biomarker profile, a feature, metabolite abundance data for the biomarker, was measured. Decision rules are developed from such biomarker profiles from a training population using data analysis algorithms in order to predict sample phenotypes based on observed gene expression patterns. While new classification tools are constantly being developed, the existing body of pattern recognition and prediction algorithms provide effective data analysis algorithms for constructing decision rules. See, for example, National Research Council; Panel on Discriminant Analysis Classification and Clustering, Discriminant Analysis and Clustering, Washington, D.C.: National Academy Press, which is hereby incorporated by reference. Furthermore, the techniques described in Dudoit et al., 2002, "Comparison of discrimination methods for the classification of tumors using gene expression data." JASA 97; 77-87, hereby incorporated by reference in its entirety, can be used to develop such decision rules.

Relevant data analysis algorithms for developing a decision rule include, but are not limited to, discriminant analysis including linear, logistic, and more flexible discrimination techniques (see, e.g., Gnanadesikan, 1977, *Methods for Statistical Data Analysis of Multivariate Observations*, New York: Wiley 1977, which is hereby incorporated by reference in its entirety); tree-based algorithms such as classification and regression trees (CART) and variants (see, e.g., Breiman, 1984, *Classification and Regression Trees*, Belmont, Calif.: Wadsworth International Group, which is hereby incorporated by reference in its entirety, as well as Section 5.1.3, below); generalized additive models (see, e.g., Tibshirani, 1990, *Generalized Additive Models*, London: Chapman and Hall, which is hereby incorporated by reference in its entirety); and neural networks (see, e.g., Neal, 1996, *Bayesian Learning for Neural Networks*, New York: Springer-Verlag; and Insua, 1998, Feedforward neural networks for nonparametric regression In: *Practical Nonparametric and Semiparametric Bayesian Statistics*, pp. 181-194, New York: Springer, which is hereby incorporated by reference in its entirety, as well as Section 1.6, below).

In one embodiment, comparison of a test subject's biomarker profile to a biomarker profiles obtained from a training population performed, and comprises applying a decision rule. The decision rule is constructed using a data analysis algorithm, such as a computer pattern recognition algorithm. Other suitable data analysis algorithms for constructing decision rules include, but are not limited to, logistic regression (see Section 1.10, below) or a nonparametric algorithm that detects differences in the distribution of feature values (e.g., a Wilcoxon Signed Rank Test (unadjusted and adjusted)). The decision rule can be based upon two, three, four, five, 10, 20 or more features, corresponding to measured observables from one, two, three, four, five, 10, 20 or more biomarkers. In one embodiment, the decision rule is based on hundreds of features or more. Decision rules may also be built using a classification tree algorithm. For example, each biomarker profile from a training population can comprise at least three features, where the features are predictors in a classification tree algorithm (see Section 1.1, below). The decision rule predicts membership within a population (or class) with an accuracy of at least about at least about 70%, of at least about 75%, of at least about 80%, of at least about 85%, of at least about 90%, of at least about 95%, of at least about 97%, of at least about 98%, of at least about 99%, or about 100%.

Suitable data analysis algorithms are known in the art, some of which are reviewed in Hastie et al., supra. In a specific embodiment, a data analysis algorithm of the invention comprises Classification and Regression Tree (CART; Section 1.1, below), Multiple Additive Regression Tree (MART; Section 1.4, below), Prediction Analysis for Microarrays (PAM; Section 1.2, below) or Random Forest analysis (Section 1.1, below). Such algorithms classify complex spectra from biological materials, such as a blood sample, to distinguish subjects as normal or as possessing biomarker expression levels characteristic of a particular disease state. In other embodiments, a data analysis algorithm of the invention comprises ANOVA and nonparametric equivalents, linear discriminant analysis (Section 1.10, below), logistic regression analysis (Section 1.10, below), nearest neighbor classifier analysis (Section 1.9, below), neural networks (Section 1.6, below), principal component analysis (Section 1.8, below), quadratic discriminant analysis (Section 1.11, below), regression classifiers (Section 1.5, below) and support vector machines (Section 1.12, below). While such algorithms may be used to construct a decision rule and/or increase the speed and efficiency of the application of the decision rule and to avoid investigator bias, one of ordinary skill in the art will realize that computer based algorithms are not required to carry out the methods of the present invention.

Decision rules can be used to evaluate biomarker profiles, regardless of the method that was used to generate the biomarker profile. For example, suitable decision rules that can be used to evaluate biomarker profiles generated using gas chromatography, as discussed in Harper, "Pyrolysis and GC in Polymer Analysis," Dekker, New York (1985). Further, Wagner et al., 2002, *Anal. Chem.* 74:1824-1835 disclose a decision rule that improves the ability to classify subjects based on spectra obtained by static time-of-flight secondary ion mass spectrometry (TOF-SIMS). Additionally, Bright et al., 2002, *J. Microbiol. Methods* 48:127-38, hereby incorporated by reference in its entirety, disclose a method of distinguishing between bacterial strains with high certainty (79-89% correct classification rates) by analysis of MALDI-TOF-MS spectra. Dallugne, 2000, *Fresenius J. Anal. Chem.* 366:701-711, hereby incorporated by reference in its entirety, discusses the use of MALDI-TOF-MS and liquid chromatography-electrospray ionization mass spectrometry (LC/ESI-MS) to classify profiles of biomarkers in complex biological samples.

5.10.1. Decision Trees

One type of decision rule that can be constructed using the feature values of the biomarkers identified in the present invention is a decision tree. Here, the "data analysis algorithm" is any technique that can build the decision tree, whereas the final "decision tree" is the decision rule. A decision tree is constructed using a training population and specific data analysis algorithms. Decision trees are described generally by Duda, 2001, *Pattern Classification*, John Wiley & Sons, Inc., New York, pp. 395-396, which is hereby incorporated by reference. Tree-based methods partition the feature space into a set of rectangles, and then fit a model (like a constant) in each one.

The training population data includes the features (e.g., expression values, or some other observable) for the biomarkers of the present invention across a training set population. One specific algorithm that can be used to construct a decision tree is a classification and regression tree (CART). Other specific decision tree algorithms include, but are not limited to, ID3, C4.5, MART, and Random Forests. CART, ID3, and C4.5 are described in Duda, 2001, *Pattern Classification*, John Wiley & Sons, Inc., New York, pp. 396-408 and pp. 411-412, which is hereby incorporated by reference. CART, MART, and C4.5 are described in Hastie et al., 2001, *The Elements of Statistical Learning*, Springer-Verlag, New York, Chapter 9, which is hereby incorporated by reference in its entirety. Random Forests are described in Breiman, 1999, "Random Forests—Random Features," Technical Report 567, Statistics Department, U. C. Berkeley, September 1999, which is hereby incorporated by reference in its entirety.

In some embodiments of the present invention, decision trees are used to classify subjects using features for combinations of biomarkers of the present invention Decision tree algorithms belong to the class of supervised learning algorithms. The aim of a decision tree is to induce a classifier (a tree) from real-world example data. This tree can be used to classify unseen examples that have not been used to derive the decision tree. As such, a decision tree is derived from training data. Exemplary training data contains data for a plurality of subjects (the training population). For each respective subject there is a plurality of features the class of the respective subject (e.g., sepsis/SIRS). In one embodiment of the present invention, the training data is expression data for a combination of biomarkers across the training population.

The following algorithm describes an exemplary decision tree derivation:

```
Tree(Examples,Class,Features)
    Create a root node
    If all Examples have the same Class value, give the root this label
    Else if Features is empty label the root according to the most
    common value
    Else begin
        Calculate the information gain for each Feature
        Select the Feature A with highest information gain and make this
        the root
        Feature
        For each possible value, v, of this Feature
            Add a new branch below the root, corresponding to A = v
            Let Examples(v) be those examples with A = v
            If Examples(v) is empty, make the new branch a leaf node
            labeled with
            the most common value among Examples
            Else let the new branch be the tree created by
            Tree(Examples(v),Class,Features - {A})
    End
```

A more detailed description of the calculation of information gain is shown in the following. If the possible classes $v_i$ of the examples have probabilities $P(v_i)$ then the information content I of the actual answer is given by:

$$I(P(v_2), \ldots, P(v_n)) = \sum_{i=1}^{n} -P(v_i)\log_2 P(v_i)$$

The I-value shows how much information we need in order to be able to describe the outcome of a classification for the specific dataset used. Supposing that the dataset contains p positive (e.g. will develop sepsis) and n negative (e.g. will not develop sepsis) examples (e.g. subjects), the information contained in a correct answer is:

$$I\left(\frac{p}{p+n}, \frac{n}{p+n}\right) = -\frac{p}{p+n}\log_2\frac{p}{p+n} - \frac{n}{p+n}\log_2\frac{n}{p+n}$$

where $\log_2$ is the logarithm using base two. By testing single features the amount of information needed to make a correct classification can be reduced. The remainder for a specific feature A (e.g. representing a specific biomarker) shows how much the information that is needed can be reduced.

$$\text{Remainder}(A) = \sum_{i=1}^{v} \frac{p_i + n_i}{p+n} I\left(\frac{p_i}{p_i + n_i}, \frac{n_i}{p_i + n_i}\right)$$

"v" is the number of unique attribute values for feature A in a certain dataset, "i" is a certain attribute value, "$p_i$" is the number of examples for feature A where the classification is positive (e.g. will develop sepsis), "$n_i$" is the number of examples for feature A where the classification is negative (e.g. will not develop sepsis). The information gain of a specific feature A is calculated as the difference between the information content for the classes and the remainder of feature A:

$$\text{Gain}(A) = I\left(\frac{p}{p+n}, \frac{n}{p+n}\right) - \text{Remainder}(A)$$

The information gain is used to evaluate how important the different features are for the classification (how well they split up the examples), and the feature with the highest information.

In general there are a number of different decision tree algorithms, many of which are described in Duda, Pattern Classification, Second Edition, 2001, John Wiley & Sons, Inc. Decision tree algorithms often require consideration of feature processing, impurity measure, stopping criterion, and pruning. Specific decision tree algorithms include, but are not limited to classification and regression trees (CART), multivariate decision trees, ID3, and C4.5.

In one approach, when a decision tree is used, the gene expression data for a select combination of genes described in the present invention across a training population is standardized to have mean zero and unit variance. The members of the training population are randomly divided into a training set and a test set. For example, in one embodiment, two thirds of the members of the training population are placed in the training set and one third of the members of the training population are placed in the test set. The expression values for a select combination of biomarkers described in the present invention is used to construct the decision tree. Then, the ability for the decision tree to correctly classify members in the test set is determined. In some embodiments, this computation is performed several times for a given combination of biomarkers. In each computational iteration, the members of the training population are randomly assigned to the training set and the test set. Then, the quality of the combination of biomarkers is taken as the average of each such iteration of the decision tree computation.

In addition to univariate decision trees in which each split is based on a feature value for a corresponding biomarker, among the set of biomarkers of the present invention, or the relative feature values of two such biomarkers, multivariate decision trees can be implemented as a decision rule. In such multivariate decision trees, some or all of the decisions actually comprise a linear combination of feature values for a plurality of biomarkers of the present invention. Such a linear combination can be trained using known techniques such as gradient descent on a classification or by the use of a sum-squared-error criterion. To illustrate such a decision tree, consider the expression:

$$0.04x1+0.16x2<500$$

Here, x1 and x2 refer to two different features for two different biomarkers from among the biomarkers of the present invention. To poll the decision rule, the values of features x1 and x2 are obtained from the measurements obtained from the unclassified subject. These values are then inserted into the equation. If a value of less than 500 is computed, then a first branch in the decision tree is taken. Otherwise, a second branch in the decision tree is taken. Multivariate decision trees are described in Duda, 2001, *Pattern Classification*, John Wiley & Sons, Inc., New York, pp. 408-409, which is hereby incorporated by reference.

Another approach that can be used in the present invention is multivariate adaptive regression splines (MARS). MARS is an adaptive procedure for regression, and is well suited for the high-dimensional problems addressed by the present invention. MARS can be viewed as a generalization of stepwise linear regression or a modification of the CART method to improve the performance of CART in the regression setting. MARS is described in Hastie et al., 2001, *The Elements of Statistical Learning*, Springer-Verlag, New York, pp. 283-295, which is hereby incorporated by reference in its entirety.

5.10.2. Predictive Analysis of Microarrays (PAM)

One approach to developing a decision rule using feature values of biomarkers of the present invention is the nearest centroid classifier. Such a technique computes, for each class (sepsis and SIRS), a centroid given by the average feature levels of the biomarkers in the class, and then assigns new samples to the class whose centroid is nearest. This approach is similar to k-means clustering except clusters are replaced by known classes. This algorithm can be sensitive to noise when a large number of biomarkers are used. One enhancement to the technique uses shrinkage: for each biomarker, differences between class centroids are set to zero if they are deemed likely to be due to chance. This approach is implemented in the Prediction Analysis of Microarray, or PAM. See, for example, Tibshirani et al., 2002, *Proceedings of the National Academy of Science USA* 99; 6567-6572, which is hereby incorporated by reference in its entirety. Shrinkage is controlled by a threshold below which differences are considered noise. Biomarkers that show no difference above the noise level are removed. A threshold can be chosen by cross-validation. As the threshold is decreased, more biomarkers are included and estimated classification errors decrease, until they reach a bottom and start climbing again as a result of noise biomarkers—a phenomenon known as overfitting.

5.10.3. Bagging, Boosting, and the Random Subspace Method

Bagging, boosting, the random subspace method, and additive trees are data analysis algorithms known as combining techniques that can be used to improve weak decision rules. These techniques are designed for, and usually applied to, decision trees, such as the decision trees described in Section 1.1, above. In addition, such techniques can also be useful in decision rules developed using other types of data analysis algorithms such as linear discriminant analysis.

In bagging, one samples the training set, generating random independent bootstrap replicates, constructs the decision rule on each of these, and aggregates them by a simple majority vote in the final decision rule. See, for example, Breiman, 1996, Machine Learning 24, 123-140; and Efron & Tibshirani, *An Introduction to Boostrap*, Chapman & Hall, New York, 1993, which is hereby incorporated by reference in its entirety.

In boosting, decision rules are constructed on weighted versions of the training set, which are dependent on previous classification results. Initially, all features under consideration have equal weights, and the first decision rule is constructed on this data set. Then, weights are changed according to the performance of the decision rule. Erroneously classified features get larger weights, and the next decision rule is boosted on the reweighted training set. In this way, a sequence of training sets and decision rules is obtained, which is then combined by simple majority voting or by weighted majority voting in the final decision rule. See, for example, Freund & Schapire, "Experiments with a new boosting algorithm," Proceedings 13th International Conference on Machine Learning, 1996, 148-156, which is hereby incorporated by reference in its entirety.

To illustrate boosting, consider the case where there are two phenotypes exhibited by the population under study, phenotype 1 (e.g., acquiring sepsis during a defined time period), and phenotype 2 (e.g., SIRS only, meaning that the subject does acquire sepsis within a defined time period). Given a vector of predictor biomarkers (e.g., a vector of features that represent such biomarkers) from the training set data, a decision rule G(X) produces a prediction taking one of the type values in the two value set: {phenotype 1, phenotype 2}. The error rate on the training sample is $$\overline{err} = \frac{1}{N}\sum_{i=1}^{N} I(y_i \neq G(x_i))$$

where N is the number of subjects in the training set (the sum total of the subjects that have either phenotype 1 or phenotype 2). For example, if there are 49 organisms that acquire sepsis and 72 organisms that remain in the SIRS state, N is 121. A weak decision rule is one whose error rate is only slightly better than random guessing. In the boosting algorithm, the weak decision rule is repeatedly applied to modified versions of the data, thereby producing a sequence of weak decision rules $G_m(x)$, m=1, 2, . . . , M. The predictions from all of the decision rules in this sequence are then combined through a weighted majority vote to produce the final decision rule:

$$G(x) = \text{sign}\left(\sum_{m=1}^{M} \alpha_m G_m(x)\right)$$

Here $\alpha_1, \alpha_2, \ldots, \alpha_M$ are computed by the boosting algorithm and their purpose is to weigh the contribution of each respective decision rule Gm(x). Their effect is to give higher influence to the more accurate decision rules in the sequence.

The data modifications at each boosting step consist of applying weights $w_1, w_2, \ldots, w_n$ to each of the training observations $(x_i, y_i)$, i=1, 2, . . . , N. Initially all the weights are set to $w_i$=1/N, so that the first step simply trains the decision rule on the data in the usual manner. For each successive iteration m=2, 3, . . . , M the observation weights are individually modified and the decision rule is reapplied to the weighted observations. At step m, those observations that were misclassified by the decision rule $G_m$–1(x) induced at the previous step have their weights increased, whereas the weights are decreased for those that were classified correctly. Thus as iterations proceed, observations that are difficult to correctly classify receive ever-increasing influence. Each successive decision rule is thereby forced to concentrate on those training observations that are missed by previous ones in the sequence.

The exemplary boosting algorithm is summarized as follows:
1. Initialize the observation weights $w_i=1/N$, $i=1, 2, \ldots, N$.
2. For $m=1$ to $M$:
   (a) Fit a decision rule $G_m(x)$ to the training set using weights $w_i$.
   (b) Compute $$err_m = \frac{\sum_{i=1}^{N} w_i I(y_i \neq G_m(x_i))}{\sum_{i=1}^{N} w_i}$$

(c) Compute $\alpha_m = \log((1-err_m)/err_m)$.
   (d) Set $w_i \rightarrow w_i \cdot \exp[\alpha_m \cdot I(y_i \neq G_m(x_i))]$, $i=1, 2, \ldots, N$.
3. Output $$G(x) = \text{sign}\left(\sum_{m=1}^{M} \alpha_m G_m(x)\right)$$

In one embodiment in accordance with this algorithm, each object is, in fact, a factor. Furthermore, in the algorithm, the current decision rule $G_m(x)$ is induced on the weighted observations at line 2a. The resulting weighted error rate is computed at line 2b. Line 2c calculates the weight am given to $G_m(x)$ in producing the final classifier $G(x)$ (line 3). The individual weights of each of the observations are updated for the next iteration at line 2d. Observations misclassified by $G_m(x)$ have their weights scaled by a factor $\exp(\alpha m)$, increasing their relative influence for inducing the next classifier $G_m+1(x)$ in the sequence. In some embodiments, modifications of the Freund and Schapire, 1997, Journal of Computer and System Sciences 55, pp. 119-139, boosting methods are used. See, for example, Hasti et al., *The Elements of Statistical Learning*, 2001, Springer, New York, Chapter 10, which is hereby incorporated by reference in its entirety. For example, in some embodiments, feature preselection is performed using a technique such as the nonparametric scoring methods of Park et al., 2002, Pac. Symp. Biocomput. 6, 52-63, which is hereby incorporated by reference in its entirety. Feature preselection is a form of dimensionality reduction in which the genes that discriminate between classifications the best are selected for use in the classifier. Then, the LogitBoost procedure introduced by Friedman et al., 2000, Ann Stat 28, 337-407 is used rather than the boosting procedure of Freund and Schapire. In some embodiments, the boosting and other classification methods of Ben-Dor et al., 2000, Journal of Computational Biology 7, 559-583, hereby incorporated by reference in its entirety, are used in the present invention. In some embodiments, the boosting and other classification methods of Freund and Schapire, 1997, Journal of Computer and System Sciences 55, 119-139, hereby incorporated by reference in its entirety, are used.

In the random subspace method, decision rules are constructed in random subspaces of the data feature space. These decision rules are usually combined by simple majority voting in the final decision rule. See, for example, Ho, "The Random subspace method for constructing decision forests," IEEE Trans Pattern Analysis and Machine Intelligence, 1998; 20(8): 832-844, which is hereby incorporated by reference in its entirety.

5.10.4. Multiple Additive Regression Trees

Multiple additive regression trees (MART) represents another way to construct a decision rule that can be used in the present invention. A generic algorithm for MART is:
1. Initialize $$f_0(x) = \text{argmin}_\gamma \sum_{i=1}^{N} L(y_i, \gamma).$$

2. For $m=1$ to $M$:
   (a) For $I=1, 2, \ldots, N$ compute $$r_{im} = -\left[\frac{\partial L(y_i \cdot f(x_i))}{\partial f(x_i)}\right]_{f=f_{m-1}}$$

(b) Fit a regression tree to the targets $r_{im}$ giving terminal regions $R_{jm}$, $j=1, 2, \ldots, J_m$.
   (c) For $j=1, 2, \ldots, J_m$ compute $$\gamma_{jm} = \text{argmin}_\gamma \sum_{x_j \in R_{jm}} L(y_i, f_{m-1}(x_i) + \gamma).$$

(d) Update $$f_m(x) = f_{m-1}(x) + \sum_{j=1}^{J_m} \gamma_{jm} I(x \in R_{jm})$$

3. Ouput $$\hat{f}(x) = f_M(x).$$

Specific algorithms are obtained by inserting different loss criteria $L(y, f(x))$. The first line of the algorithm initializes to the optimal constant model, which is just a single terminal node tree. The components of the negative gradient computed in line 2(a) are referred to as generalized pseudo residuals, r. Gradients for commonly used loss functions are summarized in Table 10.2, of Hastie et al., 2001, *The Elements of Statistical Learning*, Springer-Verlag, New York, p. 321, which is hereby incorporated by reference. The algorithm for classification is similar and is described in Hastie et al., Chapter 10, which is hereby incorporated by reference in its entirety. Tuning parameters associated with the MART procedure are the number of iterations M and the sizes of each of the constituent trees $J_m$, $m=1, 2, \ldots, M$.

5.10.5. Decision Rules Derived by Regression

In some embodiments, a decision rule used to classify subjects is built using regression. In such embodiments, the decision rule can be characterized as a regression classifier, preferably a logistic regression classifier. Such a regression classifier includes a coefficient for each of the biomarkers (e.g., a feature for each such biomarker) used to construct the classifier. In such embodiments, the coefficients for the regression classifier are computed using, for example, a maximum likelihood approach. In such a computation, the features for the biomarkers (e.g., RT-PCR, microarray data) is used. In particular embodiments, molecular marker data from only two trait subgroups is used (e.g., trait subgroup a: will acquire sepsis in a defined time period and trait subgroup b: will not acquire sepsis in a defined time period) and the dependent variable is absence or presence of a particular trait in the subjects for which biomarker data is available.

In another specific embodiment, the training population comprises a plurality of trait subgroups (e.g., three or more trait subgroups, four or more specific trait subgroups, etc.). These multiple trait subgroups can correspond to discrete stages in the phenotypic progression from healthy, to SIRS, to sepsis, to more advanced stages of sepsis in a training population. In this specific embodiment, a generalization of the logistic regression model that handles multicategory responses can be used to develop a decision that discriminates between the various trait subgroups found in the training population. For example, measured data for selected molecular markers can be applied to any of the multi-category logit models described in Agresti, *An Introduction to Categorical Data Analysis,* 1996, John Wiley & Sons, Inc., New York, Chapter 8, hereby incorporated by reference in its entirety, in order to develop a classifier capable of discriminating between any of a plurality of trait subgroups represented in a training population.

5.10.6. Neural Networks

In some embodiments, the feature data measured for select biomarkers of the present invention (e.g., RT-PCR data, mass spectrometry data, microarray data) can be used to train a neural network. A neural network is a two-stage regression or classification decision rule. A neural network has a layered structure that includes a layer of input units (and the bias) connected by a layer of weights to a layer of output units. For regression, layer of output units typically includes just one output unit. However, neural networks can handle multiple quantitative responses in a seamless fashion.

In multilayer neural networks, there are input units (input layer), hidden units (hidden layer), and output units (output layer). There is, furthermore, a single bias unit that is connected to each unit other than the input units. Neural networks are described in Duda et al., 2001, *Pattern Classification,* Second Edition, John Wiley & Sons, Inc., New York; and Hastie et al., 2001, *The Elements of Statistical Learning,* Springer-Verlag, New York, each of which is hereby incorporated by reference in its entirety. Neural networks are also described in Draghici, 2003, *Data Analysis Tools for DNA Microarrays,* Chapman & Hall/CRC; and Mount, 2001, *Bioinformatics: sequence and genome analysis,* Cold Spring Harbor Laboratory Press, Cold Spring Harbor, N.Y., each of which is hereby incorporated by reference in its entirety. What is disclosed below is some exemplary forms of neural networks.

The basic approach to the use of neural networks is to start with an untrained network, present a training pattern to the input layer, and to pass signals through the net and determine the output at the output layer. These outputs are then compared to the target values; any difference corresponds to an error. This error or criterion function is some scalar function of the weights and is minimized when the network outputs match the desired outputs. Thus, the weights are adjusted to reduce this measure of error. For regression, this error can be sum-of-squared errors. For classification, this error can be either squared error or cross-entropy (deviation). See, e.g., Hastie et al., 2001, *The Elements of Statistical Learning,* Springer-Verlag, New York, which is hereby incorporated by reference in its entirety.

Three commonly used training protocols are stochastic, batch, and on-line. In stochastic training, patterns are chosen randomly from the training set and the network weights are updated for each pattern presentation. Multilayer nonlinear networks trained by gradient descent methods such as stochastic back-propagation perform a maximum likelihood estimation of the weight values in the classifier defined by the network topology. In batch training, all patterns are presented to the network before learning takes place. Typically, in batch training, several passes are made through the training data. In online training, each pattern is presented once and only once to the net.

In some embodiments, consideration is given to starting values for weights. If the weights are near zero, then the operative part of the sigmoid commonly used in the hidden layer of a neural network (see, e.g., Hastie et al., 2001, *The Elements of Statistical Learning,* Springer-Verlag, New York, hereby incorporated by reference) is roughly linear, and hence the neural network collapses into an approximately linear classifier. In some embodiments, starting values for weights are chosen to be random values near zero. Hence the classifier starts out nearly linear, and becomes nonlinear as the weights increase. Individual units localize to directions and introduce nonlinearities where needed. Use of exact zero weights leads to zero derivatives and perfect symmetry, and the algorithm never moves. Alternatively, starting with large weights often leads to poor solutions.

Since the scaling of inputs determines the effective scaling of weights in the bottom layer, it can have a large effect on the quality of the final solution. Thus, in some embodiments, at the outset all expression values are standardized to have mean zero and a standard deviation of one. This ensures all inputs are treated equally in the regularization process, and allows one to choose a meaningful range for the random starting weights. With standardization inputs, it is typical to take random uniform weights over the range $[-0.7, +0.7]$.

A recurrent problem in the use of three-layer networks is the optimal number of hidden units to use in the network. The number of inputs and outputs of a three-layer network are determined by the problem to be solved. In the present invention, the number of inputs for a given neural network will equal the number of biomarkers selected from the training population. The number of output for the neural network will typically be just one. However, in some embodiments more than one output is used so that more than just two states can be defined by the network. For example, a multi-output neural network can be used to discriminate between, healthy phenotypes, various stages of SIRS, and/or various stages of sepsis. If too many hidden units are used in a neural network, the network will have too many degrees of freedom and is trained too long, there is a danger that the network will overfit the data. If there are too few hidden units, the training set cannot be learned. Generally speaking, however, it is better to have too many hidden units than too few. With too few hidden units, the classifier might not have enough flexibility to capture the nonlinearities in the date; with too many hidden units, the extra weight can be shrunk towards zero if appropriate regularization or pruning, as described below, is used. In typical embodiments, the number of hidden units is somewhere in the range of 5 to 100, with the number increasing with the number of inputs and number of training cases.

One general approach to determining the number of hidden units to use is to apply a regularization approach. In the regularization approach, a new criterion function is constructed that depends not only on the classical training error, but also on classifier complexity. Specifically, the new criterion function penalizes highly complex classifiers; searching for the minimum in this criterion is to balance error on the training set with error on the training set plus a regularization term, which expresses constraints or desirable properties of solutions: $J=J_{pat}+\lambda J_{reg}$. The parameter $\lambda$ is adjusted to impose the regularization more or less strongly. In other words, larger values for $\lambda$ will tend to shrink weights towards zero: typically crossvalidation with a validation set is used to estimate λ. This validation set can be obtained by setting aside a random subset of the training population. Other forms of penalty have been proposed, for example the weight elimination penalty (see, e.g., Hastie et al., 2001, *The Elements of Statistical Learning*, Springer-Verlag, New York, hereby incorporated by reference).

Another approach to determine the number of hidden units to use is to eliminate—prune—weights that are least needed. In one approach, the weights with the smallest magnitude are eliminated (set to zero). Such magnitude-based pruning can work, but is nonoptimal; sometimes weights with small magnitudes are important for learning and training data. In some embodiments, rather than using a magnitude-based pruning approach, Wald statistics are computed. The fundamental idea in Wald Statistics is that they can be used to estimate the importance of a hidden unit (weight) in a classifier. Then, hidden units having the least importance are eliminated (by setting their input and output weights to zero). Two algorithms in this regard are the Optimal Brain Damage (OBD) and the Optimal Brain Surgeon (OBS) algorithms that use second-order approximation to predict how the training error depends upon a weight, and eliminate the weight that leads to the smallest increase in training error.

Optimal Brain Damage and Optimal Brain Surgeon share the same basic approach of training a network to local minimum error at weight w, and then pruning a weight that leads to the smallest increase in the training error. The predicted functional increase in the error for a change in full weight vector δw is:

$$\delta J = \left(\frac{\partial J}{\partial w}\right)^t \cdot \delta w + \frac{1}{2}\delta w^t \cdot \frac{\partial^2 J}{\partial w^2} \cdot \delta w - O(\|\delta w\|^3)$$

where:

$$\frac{\partial^2 J}{\partial w^2}$$

is the Hessian matrix. The first term vanishes at a local minimum in error; third and higher order terms are ignored. The general solution for minimizing this function given the constraint of deleting one weight is:

$$\delta w = -\frac{w_q}{[H^{-1}]_{qq}} H^{-1} \cdot u_q \text{ and } L_q = \frac{1}{2} \cdot \frac{w_q^2}{[H^{-1}]_{qq}}$$

Here, $u_q$ is the unit vector along the qth direction in weight space and $L_q$ is approximation to the saliency of the weight q—the increase in training error if weight q is pruned and the other weights updated δw. These equations require the inverse of H. One method to calculate this inverse matrix is to start with a small value, $$H_0^{-1} = \alpha^{-1} I$$

where α is a small parameter—effectively a weight constant. Next the matrix is updated with each pattern according to:

$$H_{m+1}^{-1} = H_m^{-1} - \frac{H_m^{-1} X_{m+1} X_{m+1}^T H_m^{-1}}{\frac{n}{a_m} + X_{m+1}^T H_m^{-1} X_{m+1}} \qquad \text{Eqn. 1}$$

where the subscripts correspond to the pattern being presented and $\alpha_m$ decreases with m. After the full training set has been presented, the inverse Hessian matrix is given by $H^{-1} = H_n^{-1}$ In algorithmic form, the Optimal Brain Surgeon method is:

begin initialize $n_H$, w, θ
   train a reasonably large network to minimum error
   do compute $H^{-1}$ by Eqn. 1

$$q* \leftarrow \arg\min_q w_q^2/(2[H^{-1}]_{qq}) \text{ (saliency } L_q)$$

$$w \leftarrow w - \frac{w_{q'}}{[H^{-1}]_{q'q'}} H^{-1} e_{q'} \text{ (saliency } L_q)$$

until J(w)>θ
   return w
end

The Optimal Brain Damage method is computationally simpler because the calculation of the inverse Hessian matrix in line 3 is particularly simple for a diagonal matrix. The above algorithm terminates when the error is greater than a criterion initialized to be θ. Another approach is to change line 6 to terminate when the change in J(w) due to elimination of a weight is greater than some criterion value. In some embodiments, the back-propagation neural network See, for example Abdi, 1994, "A neural network primer," J. Biol System. 2, 247-283, hereby incorporated by reference in its entirety.

5.10.7. Clustering

In some embodiments, features for select biomarkers of the present invention are used to cluster a training set. For example, consider the case in which ten features (corresponding to ten biomarkers) described in the present invention is used. Each member m of the training population will have feature values (e.g. expression values) for each of the ten biomarkers. Such values from a member m in the training population define the vector:

$X_{1m} X_{2m} X_{3m} X_{4m} X_{5m} X_{6m} X_{7m} X_{8m} X_{9m} X_{10m}$ where $X_{im}$ is the expression level of the $i_{th}$ biomarker in organism m. If there are m organisms in the training set, selection of i biomarkers will define m vectors. Note that the methods of the present invention do not require that each the expression value of every single biomarker used in the vectors be represented in every single vector m. In other words, data from a subject in which one of the $i_{th}$ biomarkers is not found can still be used for clustering. In such instances, the missing expression value is assigned either a "zero" or some other normalized value. In some embodiments, prior to clustering, the feature values are normalized to have a mean value of zero and unit variance. Those members of the training population that exhibit similar expression patterns across the training group will tend to cluster together. A particular combination of genes of the present invention is considered to be a good classifier in this aspect of the invention when the vectors cluster into the trait groups found in the training population. For instance, if the training population includes class a: subjects that do not develop sepsis, and class b: subjects that develop sepsis, an ideal clustering classifier will cluster the population into two groups, with one cluster group uniquely representing class a and the other cluster group uniquely representing class b.

Clustering is described on pages 211-256 of Duda and Hart, *Pattern Classification and Scene Analysis*, 1973, John Wiley & Sons, Inc., New York, (hereinafter "Duda 1973") which is hereby incorporated by reference in its entirety. As described in Section 6.7 of Duda 1973, the clustering problem is described as one of finding natural groupings in a dataset. To identify natural groupings, two issues are addressed. First, a way to measure similarity (or dissimilarity) between two samples is determined. This metric (similarity measure) is used to ensure that the samples in one cluster are more like one another than they are to samples in other clusters. Second, a mechanism for partitioning the data into clusters using the similarity measure is determined.

Similarity measures are discussed in Section 6.7 of Duda 1973, where it is stated that one way to begin a clustering investigation is to define a distance function and to compute the matrix of distances between all pairs of samples in a dataset. If distance is a good measure of similarity, then the distance between samples in the same cluster will be significantly less than the distance between samples in different clusters. However, as stated on page 215 of Duda 1973, clustering does not require the use of a distance metric. For example, a nonmetric similarity function s(x, x') can be used to compare two vectors x and x'. Conventionally, s(x, x') is a symmetric function whose value is large when x and x' are somehow "similar". An example of a nonmetric similarity function s(x, x') is provided on page 216 of Duda 1973.

Once a method for measuring "similarity" or "dissimilarity" between points in a dataset has been selected, clustering requires a criterion function that measures the clustering quality of any partition of the data. Partitions of the data set that extremize the criterion function are used to cluster the data. See page 217 of Duda 1973. Criterion functions are discussed in Section 6.8 of Duda 1973.

More recently, Duda et al., Pattern Classification, $2_{nd}$ edition, John Wiley & Sons, Inc. New York, has been published. Pages 537-563 describe clustering in detail. More information on clustering techniques can be found in Kaufman and Rousseeuw, 1990, *Finding Groups in Data: An Introduction to Cluster Analysis*, Wiley, New York, N.Y.; Everitt, 1993, *Cluster analysis* (3d ed.), Wiley, New York, N.Y.; and Backer, 1995, *Computer-Assisted Reasoning in Cluster Analysis*, Prentice Hall, Upper Saddle River, N.J. Particular exemplary clustering techniques that can be used in the present invention include, but are not limited to, hierarchical clustering (agglomerative clustering using nearest-neighbor algorithm, farthest-neighbor algorithm, the average linkage algorithm, the centroid algorithm, or the sum-of-squares algorithm), k-means clustering, fuzzy k-means clustering algorithm, and Jarvis-Patrick clustering.

5.10.8. Principle Component Analysis

Principal component analysis (PCA) has been proposed to analyze gene expression data. More generally, PCA can be used to analyze feature value data of biomarkers of the present invention in order to construct a decision rule that discriminates converters from nonconverters. Principal component analysis is a classical technique to reduce the dimensionality of a data set by transforming the data to a new set of variable (principal components) that summarize the features of the data. See, for example, Jolliffe, 1986, *Principal Component Analysis*, Springer, New York, which is hereby incorporated by reference. Principal component analysis is also described in Draghici, 2003, *Data Analysis Tools for DNA Microarrays*, Chapman & Hall/CRC, which is hereby incorporated by reference. What follows is non-limiting examples of principal components analysis.

Principal components (PCs) are uncorrelated and are ordered such that the $k_{th}$ PC has the kth largest variance among PCs. The $k_{th}$ PC can be interpreted as the direction that maximizes the variation of the projections of the data points such that it is orthogonal to the first k-1 PCs. The first few PCs capture most of the variation in the data set. In contrast, the last few PCs are often assumed to capture only the residual 'noise' in the data.

PCA can also be used to create a classifier in accordance with the present invention. In such an approach, vectors for the select biomarkers of the present invention can be constructed in the same manner described for clustering above. In fact, the set of vectors, where each vector represents the feature values (e.g., abundance values) for the select genes from a particular member of the training population, can be viewed as a matrix. In some embodiments, this matrix is represented in a Free-Wilson method of qualitative binary description of monomers (Kubinyi, 1990, *3D QSAR in drug design theory methods and applications*, Pergamon Press, Oxford, pp 589-638), and distributed in a maximally compressed space using PCA so that the first principal component (PC) captures the largest amount of variance information possible, the second principal component (PC) captures the second largest amount of all variance information, and so forth until all variance information in the matrix has been considered.

Then, each of the vectors (where each vector represents a member of the training population) is plotted. Many different types of plots are possible. In some embodiments, a one-dimensional plot is made. In this one-dimensional plot, the value for the first principal component from each of the members of the training population is plotted. In this form of plot, the expectation is that members of a first subgroup (e.g. those subjects that do not develop sepsis in a determined time period) will cluster in one range of first principal component values and members of a second subgroup (e.g., those subjects that develop sepsis in a determined time period) will cluster in a second range of first principal component values.

In one ideal example, the training population comprises two subgroups: "sepsis" and "SIRS." The first principal component is computed using the molecular marker expression values for the select biomarkers of the present invention across the entire training population data set. Then, each member of the training set is plotted as a function of the value for the first principal component. In this ideal example, those members of the training population in which the first principal component is positive are the "responders" and those members of the training population in which the first principal component is negative are "subjects with sepsis."

In some embodiments, the members of the training population are plotted against more than one principal component. For example, in some embodiments, the members of the training population are plotted on a two-dimensional plot in which the first dimension is the first principal component and the second dimension is the second principal component. In such a two-dimensional plot, the expectation is that members of each subgroup represented in the training population will cluster into discrete groups. For example, a first cluster of members in the two-dimensional plot will represent subjects that develop sepsis in a given time period and a second cluster of members in the two dimensional plot will represent subjects that do not develop sepsis in a given time period.

5.10.9. Nearest Neighbor Analysis

Nearest neighbor classifiers are memory-based and require no classifier to be fit. Given a query point $x_0$, the k training points $x_{(r)}$, r, ..., k closest in distance to $x_0$ are identified and then the point $x_0$ is classified using the k nearest neighbors. Ties can be broken at random. In some embodiments, Euclidean distance in feature space is used to determine distance as:

$$d_{(i)}=\|\chi_{(i)}-\chi_o\| \quad (1)$$

Typically, when the nearest neighbor algorithm is used, the expression data used to compute the linear discriminant is standardized to have mean zero and variance 1. In the present invention, the members of the training population are randomly divided into a training set and a test set. For example, in one embodiment, two thirds of the members of the training population are placed in the training set and one third of the members of the training population are placed in the test set. A select combination of biomarkers of the present invention represents the feature space into which members of the test set are plotted. Next, the ability of the training set to correctly characterize the members of the test set is computed. In some embodiments, nearest neighbor computation is performed several times for a given combination of biomarkers of the present invention. In each iteration of the computation, the members of the training population are randomly assigned to the training set and the test set. Then, the quality of the combination of biomarkers is taken as the average of each such iteration of the nearest neighbor computation.

The nearest neighbor rule can be refined to deal with issues of unequal class priors, differential misclassification costs, and feature selection. Many of these refinements involve some form of weighted voting for the neighbors. For more information on nearest neighbor analysis, see Duda, *Pattern Classification*, Second Edition, 2001, John Wiley & Sons, Inc; and Hastie, 2001, *The Elements of Statistical Learning*, Springer, New York, each of which is hereby incorporated by reference in its entirety.

5.10.10. Linear Discriminant Analysis

Linear discriminant analysis (LDA) attempts to classify a subject into one of two categories based on certain object properties. In other words, LDA tests whether object attributes measured in an experiment predict categorization of the objects. LDA typically requires continuous independent variables and a dichotomous categorical dependent variable. In the present invention, the feature values for the select combinations of biomarkers of the present invention across a subset of the training population serve as the requisite continuous independent variables. The trait subgroup classification of each of the members of the training population serves as the dichotomous categorical dependent variable.

LDA seeks the linear combination of variables that maximizes the ratio of between-group variance and within-group variance by using the grouping information. Implicitly, the linear weights used by LDA depend on how the feature values of a molecular marker across the training set separates in the two groups (e.g., a group a that develops sepsis during a defined time period and a group b that does not develop sepsis during a defined time period) and how these feature values correlate with the feature values of other biomarkers. In some embodiments, LDA is applied to the data matrix of the N members in the training sample by K biomarkers in a combination of biomarkers described in the present invention. Then, the linear discriminant of each member of the training population is plotted. Ideally, those members of the training population representing a first subgroup (e.g. those subjects that develop sepsis in a defined time period) will cluster into one range of linear discriminant values (e.g., negative) and those member of the training population representing a second subgroup (e.g. those subjects that will not develop sepsis in a defined time period) will cluster into a second range of linear discriminant values (e.g., positive). The LDA is considered more successful when the separation between the clusters of discriminant values is larger. For more information on linear discriminant analysis, see Duda, *Pattern Classification*, Second Edition, 2001, John Wiley & Sons, Inc; and Hastie, 2001, *The Elements of Statistical Learning*, Springer, New York; and Venables & Ripley, 1997, *Modern Applied Statistics with s-plus*, Springer, New York, each of which is hereby incorporated by reference in its entirety.

5.10.11. Quadratic Discriminant Analysis

Quadratic discriminant analysis (QDA) takes the same input parameters and returns the same results as LDA. QDA uses quadratic equations, rather than linear equations, to produce results. LDA and QDA are interchangeable, and which to use is a matter of preference and/or availability of software to support the analysis. Logistic regression takes the same input parameters and returns the same results as LDA and QDA.

5.10.12. Support Vector Machines

In some embodiments of the present invention, support vector machines (SVMs) are used to classify subjects using feature values of the genes described in the present invention. SVMs are a relatively new type of learning algorithm. See, for example, Cristianini and Shawe-Taylor, 2000, *An Introduction to Support Vector Machines*, Cambridge University Press, Cambridge; Boser et al., 1992, "A training algorithm for optimal margin classifiers," in *Proceedings of the $5_{th}$ Annual ACM Workshop on Computational Learning Theory*, ACM Press, Pittsburgh, Pa., pp. 142-152; Vapnik, 1998, *Statistical Learning Theory*, Wiley, New York; Mount, 2001, *Bioinformatics: sequence and genome analysis*, Cold Spring Harbor Laboratory Press, Cold Spring Harbor, N.Y., Duda, *Pattern Classification*, Second Edition, 2001, John Wiley & Sons, Inc.; and Hastie, 2001, *The Elements of Statistical Learning*, Springer, New York; and Furey et al., 2000, Bioinformatics 16, 906-914, each of which is hereby incorporated by reference in its entirety. When used for classification, SVMs separate a given set of binary labeled data training data with a hyper-plane that is maximally distance from them. For cases in which no linear separation is possible, SVMs can work in combination with the technique of 'kernels', which automatically realizes a non-linear mapping to a feature space. The hyperplane found by the SVM in feature space corresponds to a non-linear decision boundary in the input space.

In one approach, when a SVM is used, the feature data is standardized to have mean zero and unit variance and the members of a training population are randomly divided into a training set and a test set. For example, in one embodiment, two thirds of the members of the training population are placed in the training set and one third of the members of the training population are placed in the test set. The expression values for a combination of genes described in the present invention is used to train the SVM. Then the ability for the trained SVM to correctly classify members in the test set is determined. In some embodiments, this computation is performed several times for a given combination of molecular markers. In each iteration of the computation, the members of the training population are randomly assigned to the training set and the test set. Then, the quality of the combination of biomarkers is taken as the average of each such iteration of the SVM computation.

5.10.13. Evolutionary Methods

Inspired by the process of biological evolution, evolutionary methods of decision rule design employ a stochastic search for an decision rule. In broad overview, such methods create several decision rules—a population—from a combination of biomarkers described in the present invention. Each decision rule varies somewhat from the other. Next, the decision rules are scored on feature data across the training population. In keeping with the analogy with biological evolution, the resulting (scalar) score is sometimes called the fitness. The decision rules are ranked according to their score and the best decision rules are retained (some portion of the total population of decision rules). Again, in keeping with biological terminology, this is called survival of the fittest. The decision rules are stochastically altered in the next generation—the children or offspring. Some offspring decision rules will have higher scores than their parent in the previous generation, some will have lower scores. The overall process is then repeated for the subsequent generation: the decision rules are scored and the best ones are retained, randomly altered to give yet another generation, and so on. In part, because of the ranking, each generation has, on average, a slightly higher score than the previous one. The process is halted when the single best decision rule in a generation has a score that exceeds a desired criterion value. More information on evolutionary methods is found in, for example, Duda, *Pattern Classification*, Second Edition, 2001, John Wiley & Sons, Inc.

5.10.14. Other Data Analysis Algorithms

The data analysis algorithms described above are merely examples of the types of methods that can be used to construct a decision rule for discriminating converters from nonconverters. Moreover, combinations of the techniques described above can be used. Some combinations, such as the use of the combination of decision trees and boosting, have been described. However, many other combinations are possible. In addition, in other techniques in the art such as Projection Pursuit and Weighted Voting can be used to construct decision rules.

5.11 Devices for the Diagnosis or Prognosis, or Monitoring, of a Systemic Inflammatory Condition The present invention also provides devices useful for the diagnosis, prognosis or monitoring of a systemic inflammatory condition. Some devices of the present invention comprise a computer having a central processing unit and a memory coupled to the central processing unit. The memory stores instructions for evaluating whether a one or more amounts of one or more biomarkers of a test subject at risk for developing a systemic inflammatory condition satisfies a first value set. Satisfying the first value set predicts that the test subject is likely to develop the systemic inflammatory condition.

Figure 1:
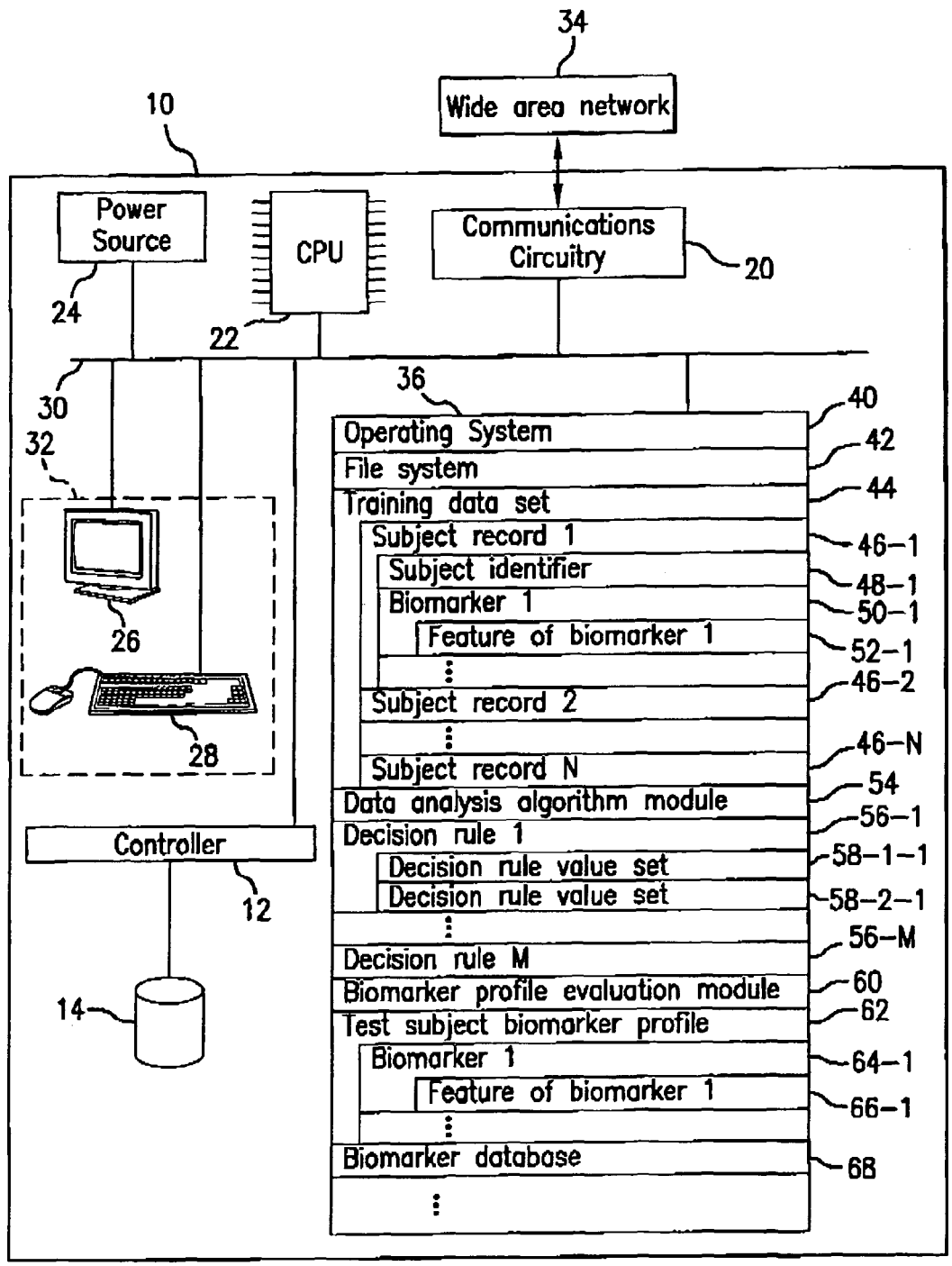
FIGS. 4-1 illustrates sensitivity and specificity versus threshold in a performance model according to the invention.

FIG. 1 details an exemplary system that supports the functionality described above. The system is preferably a computer system 10 having:

a central processing unit 22;
a main non-volatile storage unit 14, for example, a hard disk drive, for storing software and data, the storage unit 14 controlled by storage controller 12;
a system memory 36, preferably high speed random-access memory (RAM), for storing system control programs, data, and application programs, comprising programs and data loaded from non-volatile storage unit 14; system memory 36 may also include read-only memory (ROM);
a user interface 32, comprising one or more input devices (e.g., keyboard 28) and a display 26 or other output device;
a network interface card 20 for connecting to any wired or wireless communication network 34 (e.g., a wide area network such as the Internet);
an internal bus 30 for interconnecting the aforementioned elements of the system; and
a power source 24 to power the aforementioned elements.

Operation of computer 10 is controlled primarily by operating system 40, which is executed by central processing unit 22. Operating system 40 can be stored in system memory 36. In addition to operating system 40, in a typical implementation system memory 36 includes:

file system 42 for controlling access to the various files and data structures used by the present invention;
a training data set 44 for use in construction one or more decision rules in accordance with the present invention;
a data analysis algorithm module 54 for processing training data and constructing decision rules;
one or more decision rules 56;
a biomarker profile evaluation module 60 for determining whether a plurality of amounts in a biomarker profile of a test subject satisfies a first value set;
a test subject biomarker profile 62 comprising biomarkers 64 and, for each such biomarkers, amounts 66; and
a database 68 of select biomarkers of the present invention.

As illustrated in FIG. 1, computer 10 comprises software program modules and data structures. The data structures stored in computer 10 can include training data set 44, decision rules 56, test subject biomarker profile 62, and/or biomarker database 68. Each of these data structures can comprise any form of data storage system including, but not limited to, a flat ASCII or binary file, an Excel spreadsheet, a relational database (SQL), or an on-line analytical processing (OLAP) database (MDX and/or variants thereof). In some specific embodiments, such data structures are each in the form of one or more databases that include hierarchical structure (e.g., a star schema). In some embodiments, such data structures are each in the form of databases that do not have explicit hierarchy (e.g., dimension tables that are not hierarchically arranged).

In some embodiments, each of the data structures stored or accessible to system 10 are single data structures. In other embodiments, such data structures in fact comprise a plurality of data structures (e.g., databases, files, archives) that may or may not all be hosted by the same computer 10. For example, in some embodiments, training data set 44 comprises a plurality of Excel spreadsheets that are stored either on computer 10 and/or on computers that are addressable by computer 10 across wide area network 34. In another example, training data set 44 comprises a database that is either stored on computer 10 or is distributed across one or more computers that are addressable by computer 10 across wide area network 34.

It will be appreciated that many of the modules and data structures illustrated in FIG. 1 can be located on one or more remote computers. For example, some embodiments of the present application are web service-type implementations. In such embodiments, biomarker profile evaluation module 60 and/or other modules can reside on a client computer that is in communication with computer 10 via network 34. In some embodiments, for example, biomarker profile evaluation module 60 can be an interactive web page.

In some embodiments, training data set 44, decision rules 56, and/or biomarker database 68 illustrated in FIG. 1 are on a single computer (computer 10) and in other embodiments one or more of such data structures and module are hosted by one or more remote computers (not shown). Any arrangement of the data structures and software modules on one or more computers is within the scope of the present invention so long as these data structures and software modules are addressable with respect to each other across a network or by other electronic means. Thus, the present invention fully encompasses a broad array of computer systems.

6. EXAMPLES

6.1 Example 1

Analysis of Serum Metabolites of Sepsis and SIRS Patients

Examples 1 and 2 demonstrate the utility of biomarkers of the invention for the diagnosis and prognosis of sepsis and SIRS. Reference biomarker profiles were established for two populations of patient volunteers.

Patient Populations

Patients were divided into two populations. The first population ("the SIRS group") represents patients who developed SIRS and who entered into the present study at "Day 1" but who did not progress to sepsis during their hospital stay. The second population ("the sepsis group") represents patients who likewise developed SIRS and entered into the present study at Day 1 but who progressed to sepsis typically at least several days after entering the study.

Sample Collection

Blood samples were taken about every 24 hours from each study group. Clinical suspicion of sepsis in the sepsis group occurred at "time 0." The samples were taken at "time—12 hours", "time—36 hours" and "time—60 hours" preceding the day of clinical suspicion of the onset of sepsis in the sepsis group. That is, the samples from the sepsis group included those taken on the day of entry into the study (Day 1), 60 hours prior to clinical suspicion of sepsis (time—60 hours), 36 hours prior to clinical suspicion of sepsis (time—36 hours), and on the day of clinical suspicion of the onset of sepsis (time—12 hours).

Sample Preparation

To 200 µL of ice-cold methanol (stored at −20 C) was added 20 µL of human plasma. The mixture was then vortexed for 60 seconds before it was incubated at 4° C. for 20 minutes to aid the precipitation of plasma proteins. The mixture was then centrifuged at 13 k rpm for 10 minutes at 4° C. to pellet proteins. The supernatant (100 µL) containing metabolites was then transferred to an Eppendorf tube and evacuated to dry by a Speed-Vac. For mass spectrometry (MS) analysis, the metabolites were prepared with final dilution of 1:50 with respect to the original plasma in 50% methanol and 0.5% formic acid in de-ionized water with 200 nM of reserpine as an internal control.

Mass Spectrometry of Metabolites

The MS analysis of the serum metabolite extracts was performed on a Qstar XL MS/MS system (Applied Biosystems). The sample was infused into MS by the Nanomate (Advion Bioscience), an automated nano-electrospray system. The electrospray was performed at 1.5 kV spray voltage and 0.15 psi spray pressure. The MS spectrum was accumulated for 3 minutes with mass over charge (M/Z) ranging from 100 to 1200 Dalton.

6.2 Example 2

Diagnosis and Prognosis of Sepsis and SIRS with Biomarker 496.3 or Biomarker 518.3 of the Invention This Example provides time course studies of biomarkers 496.3 and 518.3 and demonstrates their utility for diagnosis, prognosis and monitoring of sepsis and SIRS. Biomarker 496.3 is 1-O-palmitoyl-2-lyso-sn-glycero-3-phosphocholine, and biomarker 518.3 is the sodium salt of 1-O-palmitoyl-2-lyso-sn-glycero-3-phosphocholine.

Blood was drawn daily from patients enrolled in this study up to 13 days from the day of entry into ICU as described in Example 1. The relative concentrations of the disclosed metabolite biomarkers in the patent were measured with ESI-MS after cold methanol extraction, also as described in Example 1.

Figure 2:
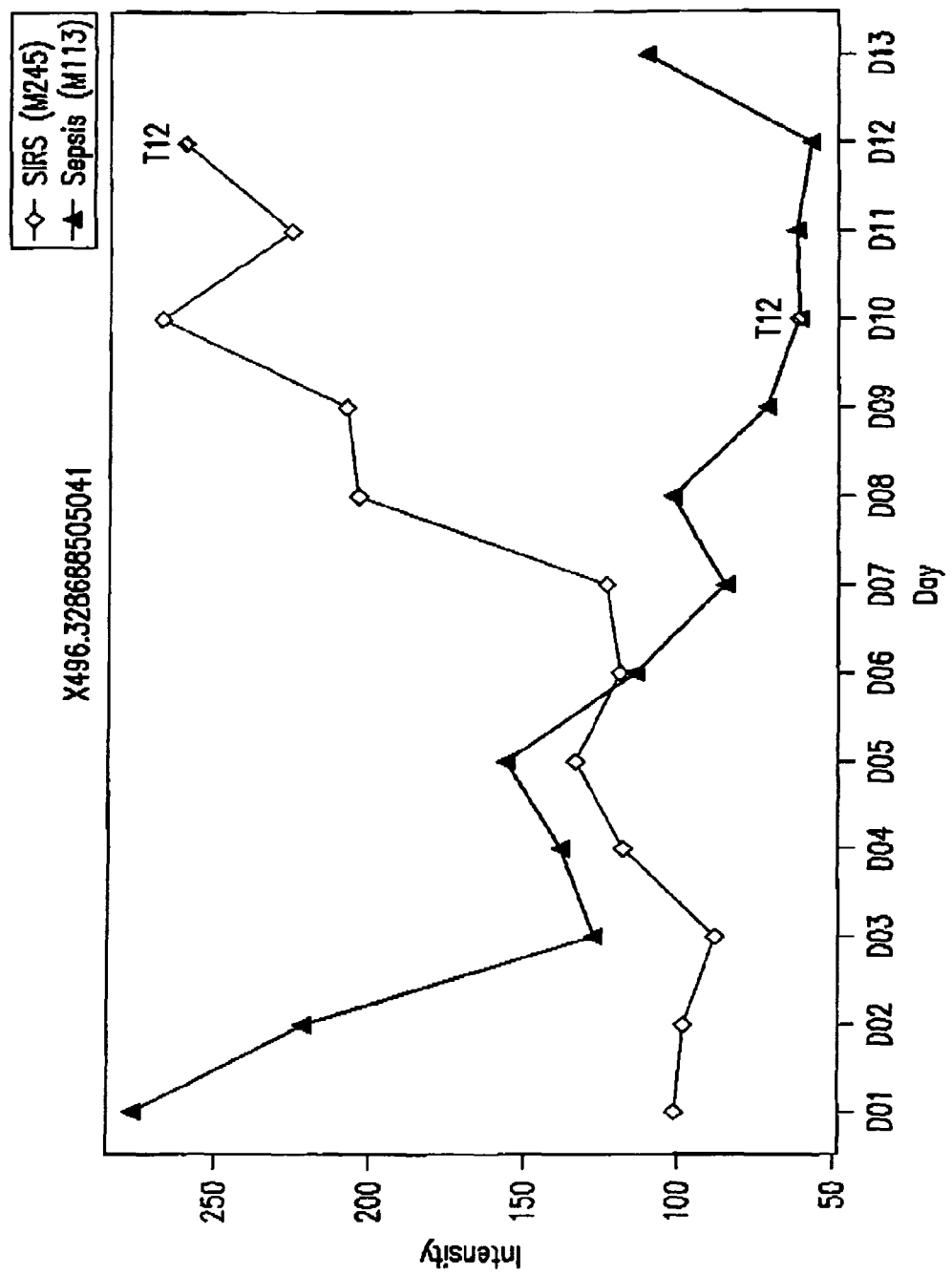
Figure 3:
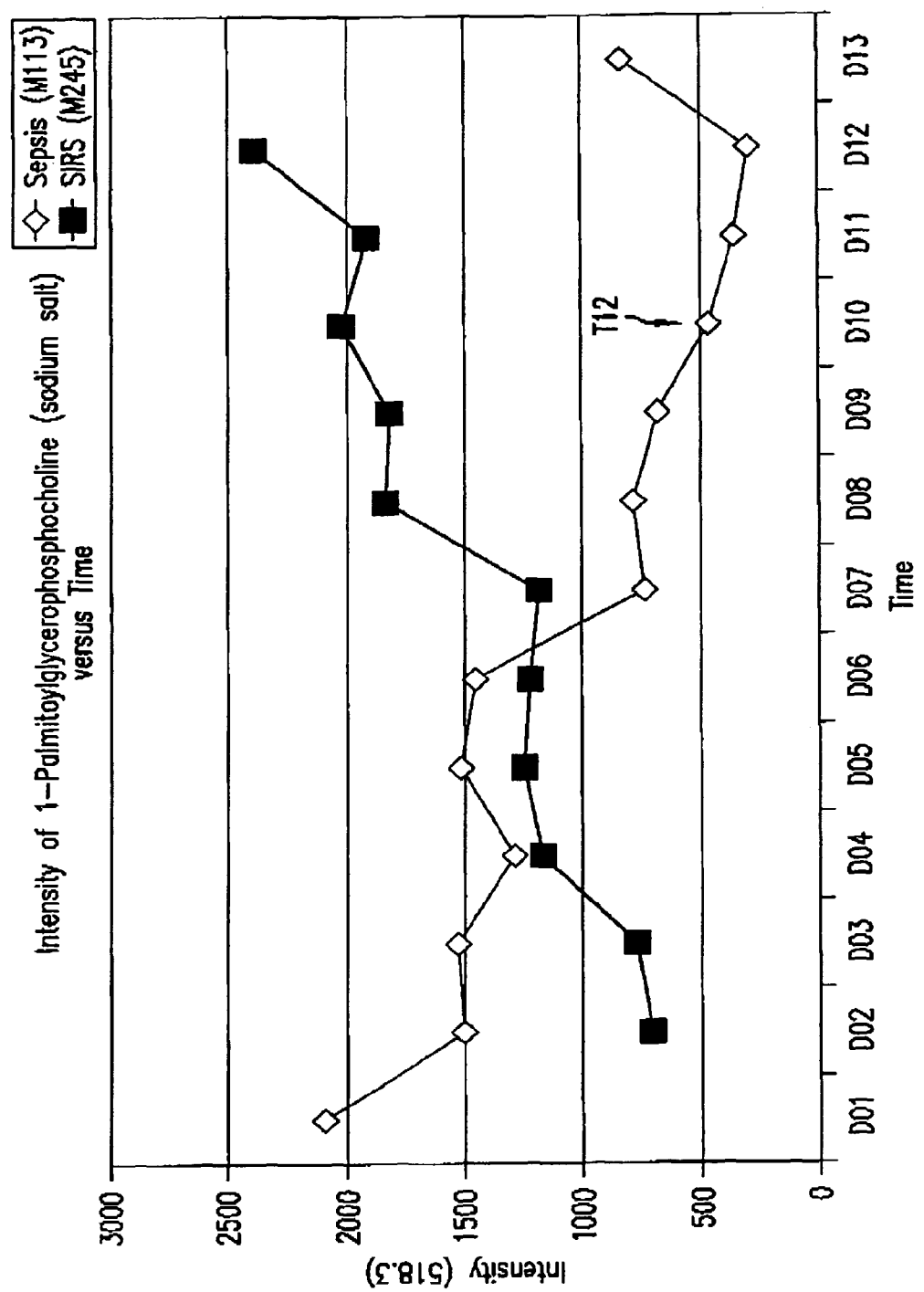

FIGS. 2 and 3 provide relative concentration changes of biomarkers 496.3 and 518.3 over a period of 13 days for sepsis patient M113 and SIRS patient M245.

As can be seen in FIG. 2, the concentration of biomarker 496.3 from the SIRS patient M245 gradually increases from day 1 to day 13, indicating a gradual recovery of the SIRS patient from an initial shock trauma.

On the other hand, the concentration of the same biomarker from the sepsis patient gradually decreases until two days after clinical diagnosis of sepsis on day 12. Also shown in FIG. 2, there is a sudden concentration drop of biomarker 518.3 between day 5 and day 7 for sepsis patient M113, indicating a starting or worsening of systemic infection.

As can be seen in FIG. 3, the concentration of biomarker 518.3 from the SIRS patient M245 gradually increases from day 1 to day 13, indicating a gradual recovery of the SIRS patient from an initial shock trauma.

On the other hand, the concentration of the same biomarker from the sepsis patient gradually decreases until two days after clinical diagnosis of sepsis on day 12. Also shown in FIG. 3, there is a sudden concentration drop of biomarker 518.3 between day 6 and day 7 for sepsis patient M113, indicating a starting or worsening of systemic infection.

Thus, it is possible to diagnose the onset c f sepsis for patient M113 between day 6 and day 7, which is about four days before clinical symptoms occurred. Sepsis patient M113 suffered a septic shock on day 12 before eventual recovery on day 13, as indicated by the recovery of biomarkers 496.3 and 518.3 (see FIGS. 2 and 3).

An early diagnosis of sepsis between day 6 and day 7 accompanied by an early therapeutic or prophylactic intervention could have saved the patient from septic shock, along with all the cost associated with the treatment of septic shock.

As demonstrated above, the amount of bio markers 496.3 and 518.3 were useful for the diagnosis and monitoring of SIRS in patients M245 (see days 1-13) and M113 (see days 1-6). In addition, biomarkers 496.3 and 518.3 were also useful for the diagnosis or prognosis of conversion to sepsis and septic shock in patient M113 (see days 6-12) and monitoring recovery from the same (see days 12-13).

6.3 Example 3

Identification of Biomarkers by MS/MS

The biomarkers were generally identified by performing tandem MS on the MS peak signals from the plasma samples. The MS/MS peak signals were then assigned to the corresponding fragments from the proposed biomarker. The biomarkers were finally confirmed by MS/MS spectra of commercially purchased compounds.

TABLE 1

MS/MS of 496.3 (1-O-palmitoyl-2-lyso-sn-glycero-3-phosphocholine)

| Ion Peak (Dalton) | Assigned Fragments |
|---|---|
| 496.34 | Parent Molecule Ion (MH$^+$) |
| 478.33 | MH$^+$ - H$_2$O |
| 313.27 | MH$^+$ - Phosphorylcholine |
| 184.07 | Phosphorylcholine |
| 104.11 | Choline |

TABLE 2

MS/MS of 524.3 (1-O-stearoyl-2-lyso-sn-glycero-3-phosphocholine)

| Ion Peak (Dalton) | Assigned Fragments |
|---|---|
| 524.37 | Parent Molecule Ion (MH$^+$) |
| 506.35 | MH$^+$ - H$_2$O |
| 341.02 | MH$^+$ - Phosphorylcholine |
| 184.07 | Phosphorylcholine |
| 104.11 | Choline |

6.4 Example 4

Least Squares Performance of
1-O-palmitoyl-2-lyso-sn-glycero-3-phosphocholine
as a Diagnostic for Sepsis Using Least Squares
Analysis This example demonstrates how well assays based on the marker 1-O-palmitoyl-2-lyso-sn-glycero-3-phosphocholine perform for the diagnosis of sepsis. In these exemplary assays, least squares curve fits are used to model the data and diagnose sepsis imminence. The performance of the models demonstrates the utility of the methods of the invention for the diagnosis, prognosis and monitoring of systemic inflammatory conditions in subjects.

The assays evaluated two features in the subjects, 1-O-palmitoyl-2-lyso-sn-glycero-3-phosphocholine with an apparent molecular weight of 496.3 and the corresponding sodium salt with an apparent molecular weight of 518.3.

There were 55 total patients, of which 23 were 23 SIRS patients and 32 were sepsis patients. Tables 4-1 and 4-2 below provides distributions of the race, gender, age, and septic status for these samples.

TABLE 4-1

| Status | Gender | African American | Caucasian | Other |
|---|---|---|---|---|
| SIRS | Female | 0 | 5 | 0 |
|  | Male | 6 | 10 | 2 |
| Sepsis | Female | 0 | 11 | 0 |
|  | Male | 5 | 16 | 0 |

TABLE 4-2

| Group | Minimum | Mean | Median | Std. Dev. | Maximum |
|---|---|---|---|---|---|
| SIRS | 18 | 52.5 | 57 | 19.4 | 84 |
| Sepsis | 19 | 40.7 | 40 | 18.4 | 79 |

Patients were scored at time points based on the imminence of sepsis. SIRS patients were scored 0. At the date of entry, sepsis patients were scored 1. Two days prior to the onset of sepsis, patients were scored 2. One day prior to the onset of sepsis patients were scored J. Immediately prior to the onset of sepsis, patients were scored 4.

"Lagged" features were constructed from features for each patient over their time course. Lag 0 data for a given patient at a given time is the data from that patient at that time only. Lag 1 data for that patient at that time is the lag 0 data, as well as data from the previous time point for that patient. Similarly, lag 2 data for that patient at that time is data available from that patient at that time as well as the two previous time points.

One consequence of constructing lags higher than 0 is that data for patients at early time points is incomplete, as lagged data is unavailable. These cases are dropped from analysis. Therefore lag 0 data is complete, lag 1 data has no cases from the first available time point, and lag 2 data has no cases from the first or second available time point. Higher lags yield more information per patient at a given time, but fewer cases to train on. Of course, the higher the lag, the longer the time before a prediction can be made, although that prediction may ultimately be more accurate.

Many multiple linear regression models were fitted, varying included features as well as model-complexity parameters, using the SPSA. (simultaneous perturbation stochastic approximation) optimization routine. For multiple regression models, no complexity parameter is available. Models were selected to optimize mean squared error loss.

A modeling recipe with a small expected loss will generally give better patient results (more accurate calls, calls earlier, etc.) than a modeling recipe with a high expected loss. However, the loss itself doesn't tell us which patients will be called, or when. To assess this, cross-validation is carried out with the identified modeling recipe. Patients are partitioned into K groups (typically 10), each of similar size and having a similar number of SIRS and septic patients. (All data from a given patient is allotted to the same group.) A model is fitted according to the recipe, leaving out each group in turn. The fitted model is then applied to the left-out patient data at each time point, and predicted SI values are calculated. Next, a sequence of thresholds is applied to each predicted SI value. For each threshold, we can then determine whether a patient's predicted SI value ever exceeded the threshold, and if so, when. The predicted results from all patients are then assembled to form aggregate sensitivity and specificity estimates for all thresholds.

6.4.1. Lag 0 Results

Features selected by the estimated best model include features with apparent molecular weights of 496.3 and 518.3. As shown in Example 3 above, these features correspond to the marker 1-O-palmitoyl-2-lyso-sn-glycero-3-phosphocholine and the corresponding sodium salt.

Iteration 1000 is estimated to have the best performance. The selected features and model complexity at this iteration are estimated to yield loss 1.4482. This model recipe was evaluated with 10-fold cross-validation. FIG. 4-1 illustrates the sensitivity and specificity that would be attained with respect to patients over their whole time course. Table 4-3 presents data from selected points. Table 4-4 summarizes estimated rates of time of first call of imminent sepsis, for the thresholds selected for high sensitivity, high overall agreement, and high specificity, respectively.

Table 4-3 provides estimated sensitivity and specificity for thresholds selected for high sensitivity (lowest threshold), high specificity (highest threshold), and high overall agreement.

TABLE 4-3

| Threshold | Sensitivity | Specificity |
|---|---|---|
| 1.329 | 96.88 | 13.04 |
| 1.7107 | 75 | 52.17 |
| 2.1145 | 6.25 | 91.3 |

Table 4-4 provides estimated distribution of first sepsis imminence call times for selected thresholds giving high sensitivity, high agreement, and high specificity, respectively. Day 1 is day of entry, Day 2 is the next day tested, etc. "I" indicates no sepsis imminence call during the course of the study.

TABLE 4-4

| | | Day of Study: | | | | |
|---|---|---|---|---|---|---|
| | | 1 | 2 | 3 | 4 | I |
| Sensitivity | Sepsis | 28 | 2 | 0 | 1 | 1 |
| | SIRS | 19 | 1 | 0 | 0 | 3 |
| Agreement | Sepsis | 10 | 4 | 5 | 5 | 8 |
| | SIRS | 7 | 1 | 0 | 3 | 12 |
| Specificity | Sepsis | 0 | 0 | 0 | 2 | 30 |
| | SIRS | 0 | 0 | 1 | 1 | 21 |

FIG. 4-2 illustrates evolution of feature inclusion parameters during the optimization. While the last iteration is typically best, the process is random and the best iteration is estimated; in this case, iteration 1000 is estimated to be best.

6.4.2. Lag 1 Results

Features selected by the estimated best model include features with apparent molecular weights of 496.3 and 518.3. As shown in Example 3 above, these features correspond to the marker 1-O-palmitoyl-2-lyso-sn-glycero-3-phosphocholine and the corresponding sodium salt.

Iteration 1000 is estimated to have the best performance. The selected features and model complexity at this iteration are estimated to yield loss 1.4638. This model recipe was evaluated with 10-fold cross-validation. FIG. 4-3 illustrates the sensitivity and specificity that would be attained with respect to patients over their whole time course. Table 4-5 presents data from selected points. Table 4-6 summarizes estimated rates of time of first call of imminent sepsis, for the thresholds selected for high sensitivity, high overall agreement, and high specificity, respectively.

Table 4-5 provides estimated sensitivity and specificity for thresholds selected for high sensitivity (lowest threshold), high specificity (highest threshold), and high overall agreement.

TABLE 4-5

| Threshold | Sensitivity | Specificity |
|---|---|---|
| 1.7107 | 90.62 | 30.43 |
| 2.1145 | 75 | 65.22 |
| 2.2587 | 62.5 | 91.3 |

Table 4-6 provides estimated distribution of first sepsis imminence call times for selected thresholds giving high sensitivity, high agreement, and high specificity, respectively. Day 1 is day of entry, Day 2 is the next day tested, etc. "I" indicates no sepsis imminence call during the course of the study.

TABLE 4-6

| | | Day of Study: | | | | |
|---|---|---|---|---|---|---|
| | | 1 | 2 | 3 | 4 | I |
| Sensitivity | Sepsis | 0 | 21 | 4 | 4 | 3 |
| | SIRS | 0 | 5 | 3 | 8 | 7 |
| Agreement | Sepsis | 0 | 8 | 10 | 6 | 8 |
| | SIRS | 0 | 1 | 0 | 7 | 15 |
| Specificity | Sepsis | 0 | 5 | 8 | 7 | 12 |
| | SIRS | 0 | 0 | 0 | 2 | 21 |

FIGS. 4-4 and 4-5 illustrate evolution of feature inclusion parameters during the optimization. While the last iteration is typically best, the process is random and so we estimate the best iteration; in this case, iteration 1000 is estimated to be best.

6.4.3. Lag 2 Results

Features selected by the estimated best model include features with apparent molecular weights of 496.3 and 518.3. As shown in Example 3 above, these features correspond to the marker 1-O-palmitoyl-2-lyso-sn-glycero-3-phosphocholine and the corresponding sodium salt.

Iteration 1000 is estimated to have the best performance. The selected features and model complexity at this iteration are estimated to yield loss 1.6208. This model recipe was evaluated with 10-fold cross-validation. FIG. 4-6 illustrates the sensitivity and specificity that would be attained with respect to patients over their whole time course. Table 4-7 presents data from selected points. Table 4-8 summarizes estimated rates of time of first call of imminent sepsis, for the thresholds selected for high sensitivity, high overall agreement, and high specificity, respectively.

Table 4-7 provides estimated sensitivity and specificity for thresholds selected for high sensitivity (lowest threshold), high specificity (highest threshold), and high overall agreement.

TABLE 4-7

| Threshold | Sensitivity | Specificity |
|---|---|---|
| 1.7107 | 90.62 | 26.09 |
| 2.3465 | 68.75 | 69.57 |
| 2.5329 | 59.38 | 91.3 |

Table 4-8 provides estimated distribution of first sepsis imminence call times for selected thresholds giving high sensitivity, high agreement, and high specificity, respectively. Day 1 is day of entry, Day 2 is the next day tested, etc. "I" indicates no sepsis imminence call during the course of the study.

TABLE 4-8

| | | Day of Study: | | | | |
|---|---|---|---|---|---|---|
| | | 1 | 2 | 3 | 4 | I |
| Sensitivity | Sepsis | 0 | 0 | 24 | 5 | 3 |
| | SIRS | 0 | 0 | 8 | 9 | 6 |
| Agreement | Sepsis | 0 | 0 | 19 | 3 | 10 |
| | SIRS | 0 | 0 | 0 | 7 | 16 |
| Specificity | Sepsis | 0 | 0 | 11 | 8 | 13 |
| | SIRS | 0 | 0 | 0 | 2 | 21 |

FIGS. 4-7 through 4-9 illustrate evolution of feature inclusion parameters during the optimization. While the last itera-

6.5 Example 5

Performance of 1-O-palmitoyl-2-lyso-sn-glycero-3-phosphocholine as a Diagnostic for Sepsis Using Neural Net Analysis This example demonstrates how well assays based on the marker 1-O-palmitoyl-2-lyso-sn-glycero-3-phosphocholine perform for the diagnosis of sepsis. In these exemplary assays, neural net curve fits are used to model the data and diagnose sepsis imminence. The performance of the models demonstrates the utility of the methods of the invention for the diagnosis, prognosis and monitoring of systemic inflammatory conditions in subjects.

The assays evaluated two features in the subjects, 1-O-palmitoyl-2-lyso-sn-glycero-3-phosphocholine with an apparent molecular weight of 496.3 and the corresponding sodium salt with an apparent molecular weight of 518.3.

There were 55 total patients, of which 23 were 23 SIRS patients and 32 were sepsis patients. Tables 5-1 and 5-2 below provide distributions of the race, gender, age, and septic status for these samples.

TABLE 5-1

| Status | Gender | African American | Caucasian | Other |
|---|---|---|---|---|
| SIRS | Female | 0 | 5 | 0 |
|  | Male | 6 | 10 | 2 |
| Sepsis | Female | 0 | 11 | 0 |
|  | Male | 5 | 16 | 0 |

TABLE 5-2

| Group | Minimum | Mean | Median | Std. Dev. | Maximum |
|---|---|---|---|---|---|
| SIRS | 18 | 52.5 | 57 | 19.4 | 84 |
| Sepsis | 19 | 40.7 | 40 | 18.4 | 79 |

Patients were scored at time points based on the imminence of sepsis ("SI"). SIRS patients were scored 0. At the date of entry, sepsis patients were scored 1. Two days prior to the onset of sepsis, patients were scored 2. One day prior to the onset of sepsis patients were scored J. Immediately prior to the onset of sepsis, patients were scored 4.

"Lagged" features were constructed from features for each patient over their time course. Lag 0 data for a given patient at a given time is the data from that patient at that time only. Lag 1 data for that patient at that time is the lag 0 data, as well as data from the previous time point for that patient. Similarly, lag 2 data for that patient at that time is data available from that patient at that time as well as the two previous time points.

One consequence of constructing lags higher than 0 is that data for patients at early time points is incomplete, as lagged data is unavailable. These cases are dropped from analysis. Therefore lag 0 data is complete, lag 1 data has no cases from the first available time point, and lag 2 data has no cases from the first or second available time point. Higher lags yield more information per patient at a given time, but fewer cases to train on. Of course, the higher the lag, the longer the time before a prediction can be made, although that prediction may ultimately be more accurate.

Many neural net models were fitted, varying included features as well as model-complexity parameters, using the SPSA (simultaneous perturbation stochastic approximation) optimization routine. For neural net models, complexity is governed by the number of hidden nodes and weight decay. Models were selected to optimize mean squared error loss.

A modeling recipe with a small expected loss will generally give better patient results (more accurate calls, calls earlier, etc.) than a modeling recipe with a high expected loss. However, the loss itself doesn't tell us which patients will be called, or when. To assess this, cross-validation is carried out with the identified modeling recipe. Patients are partitioned into K groups (typically 10), each of similar size and having a similar number of SIRS and septic patients. (All data from a given patient is allotted to the same group.) A model is fitted according to the recipe, leaving out each group in turn. The fitted model is then applied to the left-out patient data at each time point, and predicted SI values are calculated. Next, a sequence of thresholds is applied to each predicted SI value. For each threshold, we can then determine whether a patient's predicted SI value ever exceeded the threshold, and if so, when. The predicted results from all patients are then assembled to form aggregate sensitivity and specificity estimates for all thresholds.

6.5.1. Lag 0 Results

Features selected by the estimated best model include features with apparent molecular weights of 496.3 and 518.3. As shown in Example 3 above, these features correspond to the marker 1-O-palmitoyl-2-lyso-sn-glycero-3-phosphocholine and the corresponding sodium salt. Model complexity parameters identified are 5 hidden nodes and weight decay 0.3003.

Iteration 1000 is estimated to have the best performance. The selected features and model complexity at this iteration are estimated to yield loss 1.3537. This model recipe was evaluated with 10-fold cross-validation. FIGS. 5-1 illustrates the sensitivity and specificity that would be attained with respect to patients over their whole time course. Table 5-3 presents data from selected points. Table 5-4 summarizes estimated rates of time of first call of imminent sepsis, for the thresholds selected for high sensitivity, high overall agreement, and high specificity, respectively.

Table 5-3 provides estimated sensitivity and specificity for thresholds selected for high sensitivity (lowest threshold), high specificity (highest threshold), and high overall agreement.

TABLE 5-3

| Threshold | Sensitivity | Specificity |
|---|---|---|
| 1.1336 | 96.88 | 4.35 |
| 2.0036 | 68.75 | 69.57 |
| 2.5551 | 37.5 | 91.3 |

Table 5-4 provides estimated distribution of first sepsis imminence call times for selected thresholds giving high sensitivity, high agreement, and high specificity, respectively. Day 1 is day of entry, Day 2 is the next day tested, etc. "I" indicates no sepsis imminence call during the course of the study.

TABLE 5-4

|  |  | Day of Study: | | | | |
|---|---|---|---|---|---|---|
|  |  | 1 | 2 | 3 | 4 | I |
| Sensitivity | Sepsis | 21 | 6 | 3 | 1 | 1 |
|  | SIRS | 17 | 2 | 0 | 3 | 1 |

TABLE 5-4-continued

|  |  | Day of Study: | | | | |
|---|---|---|---|---|---|---|
|  |  | 1 | 2 | 3 | 4 | I |
| Agreement | Sepsis | 5 | 2 | 9 | 6 | 10 |
|  | SIRS | 3 | 1 | 0 | 3 | 16 |
| Specificity | Sepsis | 1 | 0 | 4 | 7 | 20 |
|  | SIRS | 0 | 1 | 0 | 1 | 21 |

FIG. 5-2 illustrates evolution of feature inclusion parameters during the optimization. While the last iteration is typically best, the process is random and the best iteration is estimated; in this case, iteration 1000 is estimated to be best.

6.5.2. Lag 1 Results

Features selected by the estimated best model include features with apparent molecular weights of 496.3 and 518.3. As shown in Example 3 above, these features correspond to the marker 1-O-palmitoyl-2-lyso-sn-glycero-3-phosphocholine and the corresponding sodium salt. Model complexity parameters identified are 4 hidden nodes and weight decay 1.0563.

Iteration 847 is estimated to have the best performance. The selected features and model complexity at this iteration are estimated to yield loss 1.3603. This model recipe was evaluated with 10-fold cross-validation. FIG. 5-3 illustrates the sensitivity and specificity that would be attained with respect to patients over their whole time course. Table 5-5 presents data from selected points. Table 5-6 summarizes estimated rates of time of first call of imminent sepsis, for the thresholds selected for high sensitivity, high overall agreement, and high specificity, respectively.

Table 5-5 provides estimated sensitivity and specificity for thresholds selected for high sensitivity (lowest threshold), high specificity (highest threshold), and high overall agreement.

TABLE 5-5

| Threshold | Sensitivity | Specificity |
|---|---|---|
| 1.3215 | 90.62 | 26.09 |
| 2.1481 | 68.75 | 69.57 |
| 2.5311 | 59.38 | 91.3 |

Table 5-6 provides estimated distribution of first sepsis imminence call times for selected thresholds giving high sensitivity, high agreement, and high specificity, respectively. Day 1 is day of entry, Day 2 is the next day tested, etc. "I" indicates no sepsis imminence call during the course of the study.

TABLE 5-6

|  |  | Day of Study: | | | | |
|---|---|---|---|---|---|---|
|  |  | 1 | 2 | 3 | 4 | I |
| Sensitivity | Sepsis | 0 | 21 | 3 | 5 | 3 |
|  | SIRS | 0 | 6 | 2 | 9 | 6 |
| Agreement | Sepsis | 0 | 10 | 9 | 3 | 10 |
|  | SIRS | 0 | 1 | 0 | 6 | 16 |
| Specificity | Sepsis | 0 | 7 | 5 | 7 | 13 |
|  | SIRS | 0 | 0 | 0 | 2 | 21 |

FIGS. 5-4 through 5-5 illustrate evolution of feature inclusion parameters during the optimization. While the last iteration is typically best, the process is random and so we estimate the best iteration; in this case, iteration 847 is estimated to be best.

6.5.3. Lag 2 Results

Features selected by the estimated best model include features with apparent molecular weights of 496.3 and 518.3. As shown in Example 3 above, these features correspond to the marker 1-O-palmitoyl-2-lyso-sn-glycero-3-phosphocholine and the corresponding sodium salt. Model complexity parameters identified are 3 hidden nodes and weight decay 1.6457.

Iteration 1000 is estimated to have the best performance. The selected features and model complexity at this iteration are estimated to yield loss 1.5287. This model recipe was evaluated with 10-fold cross-validation. FIG. 5-6 illustrates the sensitivity and specificity that would be attained with respect to patients over their whole time course. Table 5-7 presents data from selected points. Table 5-8 summarizes estimated rates of time of first call of imminent sepsis, for the thresholds selected for high sensitivity, high overall agreement, and high specificity, respectively.

Table 5-7 provides estimated sensitivity and specificity for thresholds selected for high sensitivity (lowest threshold), high specificity (highest threshold), and high overall agreement.

TABLE 5-7

| Threshold | Sensitivity | Specificity |
|---|---|---|
| 1.0748 | 90.62 | 13.04 |
| 2.1886 | 68.75 | 65.22 |
| 2.6667 | 62.5 | 91.3 |

Table 5-8 provides estimated distribution of first sepsis imminence call times for selected thresholds giving high sensitivity, high agreement, and high specificity, respectively. Day 1 is day of entry, Day 2 is the next day tested, etc. "I" indicates no sepsis imminence call during the course of the study.

TABLE 5-8

|  |  | Day of Study: | | | | |
|---|---|---|---|---|---|---|
|  |  | 1 | 2 | 3 | 4 | I |
| Sensitivity | Sepsis | 0 | 0 | 27 | 2 | 3 |
|  | SIRS | 0 | 0 | 11 | 9 | 3 |
| Agreement | Sepsis | 0 | 0 | 19 | 3 | 10 |
|  | SIRS | 0 | 0 | 2 | 6 | 15 |
| Specificity | Sepsis | 0 | 0 | 13 | 7 | 12 |
|  | SIRS | 0 | 0 | 0 | 2 | 21 |

FIGS. 5-7 through 5-9 illustrate evolution of feature inclusion parameters during the optimization. While the last iteration is typically best, the process is random and so we estimate the best iteration; in this case, iteration 1000 is estimated to be best.

6.6 Example 6

Colorimetric Enzymatic Assay for Total Lysophosphatidylcholine Determination

Patient Populations

Patients were divided into two populations. The first population ("the SIRS group") represents patients who developed SIRS and who entered into the present study at "Day 1" but who did not progress to sepsis during their hospital stay. The second population ("the sepsis group") represents patients who likewise developed SIRS and entered into the present study at Day 1 but who progressed to sepsis typically at least several days after entering the study.

Sample Collection

Blood samples were taken about every 24 hours from each study group. Clinical suspicion of sepsis in the sepsis group occurred at "time 0." The samples were taken at "time 12 hours", "time 36 hours" and "time—60 hours" preceding the day of clinical suspicion of the onset of sepsis in the sepsis group. That is, the samples from the sepsis group included those taken on the day of entry into the study (Day 1), 60 hours prior to clinical suspicion of sepsis (time 60 hours), 36 hours prior to clinical suspicion of sepsis (time 36 hours), and on the day of clinical suspicion of the onset of sepsis (time—12 hours).

Sources of Reagents

Lysophospholipase (EC 3.1.1.5) was obtained from Asachi Chemical Co. (Tokyo, Japan). Glycerophosphorylcholine phosphodiesterase (GPCP; EC 3.1.4.2), choline oxidase (COD; EC 1.1.3.17), peroxidase (EC 1.11.1.7), sodium N-ethyl-N-(2-hydroxy-3-sulfopropyl)-3-methylaniline dehydrate (TOOS) and 4-aminoantipyrine were purchased from Aldrich (Milwaukee, Wis.). 1-Palmitoyl-2-hydroxy-phosphatidylcholine was obtained from Avanti Polar-Lipids Inc. (Alabaster, Ala.). 10-acetyl-3,7-dihydroxyphenoxazine was obtained from Invitrogen (Carlsbad, Calif.).

Mechanism

In the assay mechanism shown in Scheme 1 (FIG. 6), one lysophosphatidylcholine (LPC) molecule can go through a series of enzymatic reactions to yield two hydrogen peroxide molecules. The resulting hydrogen peroxide can oxidize 4-aminoantipyrine in the presence of N-ethyl-N-(2-hydroxy-3-sulfopropyl)-3-methylaniline dehydrate sodium salt (TOOS) to produce a quinoneimine dye. The absorbance intensity of quinoneimine can be measured at wavelength of 590 nm.

Reagents

Reagent A comprises 100 mM Tris-HCl (pH 8.0), 0.01% Triton X-100, 1 mM calcium chloride, 3 mM TOOS(N-Ethyl-N-(2-hydroxy-3-sulfopropyl)-3-methylaniline, sodium salt, dihydrate), 10 K Units/L peroxidase, 0.1 K Units/L GPCP (glycerophosphorylcholine phosphodiesterase), and 10 K Units/L COD (choline oxidase). Reagent B comprises 100 mM Tris-HCl (pH 8.0), 0.01% Triton X-100, 5 mM 4-aminoantipyrine and 30 K Units/L lysophospholipase.

LPC Colorimetric Enzymatic Assay

An 8 µl plasma sample was pre-incubated with 240 µl of reagent A for 5 minutes at 37° C., and the absorbance between 570 nm (primary wavelength) and 700 nm (secondary wavelength) was measured in a plate reader (Perkin-Elmer Victor3). Reaction was started by addition of 80 µl of reagent B. After 5 minutes, the absorbance between 570 nm and 700 nm was measured. The total LPC concentration was determined with the aid of a calibration curve from sequential dilution of 500 µmol/L of 1-palmitoyl-2-hydroxy-phosphatidylcholine.

Results

| Sample | Rep1 (absorbance) | Rep2 (absorbance) | Mean (absorbance) |
|---|---|---|---|
| STD1: 600 µM | 0.449 | 0.445 | 0.447 |
| STD2: 400 µM | 0.336 | 0.334 | 0.335 |
| STD3: 200 µM | 0.169 | 0.233 | 0.201 |
| STD6: 0 µM | 0.071 | 0.116 | 0.094 |
| Healthy subject | 0.231 | 0.223 | 0.228 |
| Patient 113 D10 (sepsis) | 0.081 | 0.078 | 0.080 |
| Patient 237 D09 (SIRS) | 0.165 | 0.193 | 0.179 |

As shown in the table above, a sepsis patient and a SIRS patient have lower LPC concentrations compared to a normal healthy subject. The LPC concentration in the sepsis patient is further decreased compared to the SIRS patient. Both differences were seen in a larger set of samples.

6.7 Example 7

Fluorescent Enzymatic Assay For Total LPC Determination

Patient Populations

Patients were divided into two populations. The first population ("the SIRS group") represents patients who developed SIRS and who entered into the present study at "Day 1" but who did not progress to sepsis during their hospital stay. The second population ("the sepsis group") represents patients who likewise developed SIRS and entered into the present study at Day 1 but who progressed to sepsis typically at least several days after entering the study.

Sample Collection

Blood samples were taken about every 24 hours from each study group. Clinical suspicion of sepsis in the sepsis group occurred at "time 0." The samples were taken at "time 12 hours", "time 36 hours" and "time—60 hours" preceding the day of clinical suspicion of the onset of sepsis in the sepsis group. That is, the samples from the sepsis group included those taken on the day of entry into the study (Day 1), 60 hours prior to clinical suspicion of sepsis (time 60 hours), 36 hours prior to clinical suspicion of sepsis (time 36 hours), and on the day of clinical suspicion of the onset of sepsis (time—12 hours).

Sources of Reagents

Lysophospholipase (EC 3.1.1.5) was obtained from Asachi Chemical Co. (Tokyo, Japan). Glycerophosphorylcholine phosphodiesterase (GPCP; EC 3.1.4.2), choline oxidase (COD; EC 1.1.3.17), peroxidase (EC 1.11.1.7), sodium N-ethyl-N-(2-hydroxy-3-sulfopropyl)-3-methylaniline dehydrate (TOOS) and 4-aminoantipyrine were purchased from Aldrich (Milwaukee, Wis.). 1-Palmitoyl-2-hydroxy-phosphatidylcholine was obtained from Avanti Polar-Lipids Inc. (Alabaster, Ala.). 10-acetyl-3,7-dihydroxyphenoxazine was obtained from Invitrogen (Carlsbad, Calif.).

Mechanism

Similar to the colorimetric enzymatic assay, one LPC molecule can yield through a series of enzymatic reactions two hydrogen peroxide molecules (Scheme 1; see FIG. 6). The resulting hydrogen peroxide can then oxidize 10-acetyl-3,7-dihydroxyphenoxazine to a fluorescent product, 7-hydroxy-3H-phenoxazine-3-one. The fluorescent intensity of 7-hydroxy-3H-phenoxazine-3-one can be measured at 590 nm with an excitation wavelength around 530 nm.

Reagents

Reagent A comprises 100 mM Tris-HCl (pH 8.0), 0.01% Triton X-100, 10 mM magnesium chloride, 0.1 K units/L GPCP (glycerophosphorylcholine phosphodiesterase), 10 K units/L peroxidase, 10 K units/L of COD (choline oxidase) and 20 mM 10-acetyl-3,7-dihydroxyphenoxazine. Reagent B comprises 100 mM Tris-HCl (pH 8.0), 0.01% Triton X-100 and 30 K units/L of lysophospholipase.

240 μL of Reagent A are added to each well of a black 96 microplate for fluorescence. 8 μL of each sample and or standards are added into each well containing Reagent A. 80 μL of Reagent B are added into each well. The resulting mixture is incubated for 60 minutes or longer at 37° C., protected from light. Fluorescence is read on the Perkin Elmer Victor 3 Plate reader with an excitation wavelength of 530 nm, an emission wavelength of 590 nm, lamp energy of '10000', and emission aperture 'Small'. Total LPC is determined with the aid of a calibration curve from sequentially diluted 500 μmmol/L of 1-palmitoyl-2-hydroxy-phosphatidylcholine in a buffer solution comprising 100 mM Tris-HCl (pH 8.0), 0.01% Triton X-100 and 10 mM magnesium chloride.

Results

The total LPC concentrations for 29 sepsis and 22 SIRS subjects on the day of entry, T-60, T-36 and T-12 (the day of clinical suspicion of the onset of sepsis) intervals are shown in FIG. 7. As can be seen in from the FIG. 7, the total LPC concentration for most SIRS patients gradually increases from the day of entry, indicating a gradual recovery of each SIRS patient from an initial shock trauma. On the other hand, the total LPC concentration for most sepsis patients starts dropping or levels two days before the day of clinical suspicion of the onset of sepsis (T-12).

In this data set, clinic prognosis of sepsis can be made according to the methods of the invention one to two days before the onset of sepsis with 90% specificity and 60% sensitivity, using the following criteria:

LPC concentration ($D_n$)<60 μM on the day of the call (n day); and $D_n$-$D_{n-1}$<0 μM (LPC concentration went down or leveled off).

An early diagnosis of sepsis accompanied by an early therapeutic or prophylactic intervention could have saved the patient from septic shock along with all the cost associated with the treatment of septic shock.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for the diagnosis of sepsis in a SIRS-positive patient comprising the steps of:
measuring over time a plurality of amounts of total lysophosphatidylcholine in fluid or tissue of the SIRS-positive patient; and
diagnosing sepsis in the SIRS-positive patient, based on the measurements of the plurality of amounts of total lysophosphatidylcholine;
wherein the measuring and diagnosing steps are made prior to laboratory confirmation of a clinically significant infection causative of sepsis; and
wherein a decrease in the plurality of amounts of total lysophosphatidylcholine measured over time, such that a second amount is less than 75% of a previous amount over a 24 hour interval, indicates diagnosis of sepsis.

2. The method of claim 1 wherein said lysophosphatidylcholine comprises 1-O-palmitoyl-2-lyso-sn-glycero-3-phosphocholine and 1-O-stearoyl-2-lyso-sn-glycero-3-phosphocholine.

3. The method of claim 1 where total free lysophosphatidylcholine indicates the amount of total lysophosphatidylcholine.

4. The method of claim 1 where total bound lysophosphatidylcholine indicates the amount of total lysophosphatidylcholine.

5. The method of claim 1 where total free and bound lysophosphatidylcholine indicates the amount of total lysophosphatidylcholine.

6. A method for the diagnosis of sepsis in a SIRS-positive patient comprising the steps of:
measuring over time a plurality of amounts of a compound according to formula (I)

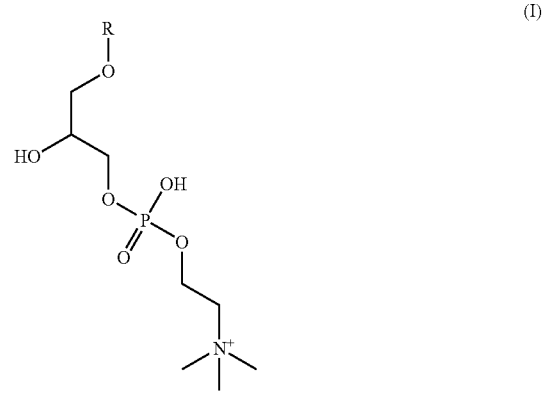

or a salt or solvate thereof, wherein R is $C_{16}$-$C_{18}$ acyl, in fluid or tissue of the SIRS-positive patient; and
diagnosing sepsis in the SIRS-positive patient, based on the measurements of the plurality of amounts of the compound;
wherein the measuring and diagnosing steps are made prior to laboratory confirmation of a clinically significant infection causative of sepsis; and
wherein a decrease in the plurality of amounts of the compound measured over time, such that a second amount is less than 75% of a previous amount over a 24 hour interval, indicates diagnosis of sepsis.

7. The method of claim 6 wherein R is saturated acyl.
8. The method of claim 6 wherein R is $C_{16}$ saturated acyl.
9. The method of claim 6 wherein R is $C_{18}$ saturated acyl.
10. The method of claim 6 wherein R is unbranched $C_{16}$-$C_{18}$ acyl.
11. The method of claim 6 wherein R is palmitoyl.
12. The method of claim 6 wherein R is stearoyl.
13. The method of claim 1 or 6 additionally comprising the measurement of one or more biomarkers, wherein said biomarker is other than lysophosphatidylcholine.
14. The method of claim 1 or 6 wherein the amount is measured by spectrometry, chromatography, immunoassay, electrophoresis or enzymatic assay.
15. The method of claim 1 or 6 wherein the fluid or tissue is blood, plasma, saliva, serum, sputum, urine, cells, cellular extract or tissue biopsy.
16. The method of claim 1 or 6 further comprising using one or more clinical measurements.

17. The method of claim 16 wherein the clinical measurement is selected from the group consisting of respiratory rate, temperature, heart rate, white blood cell count, monocyte count, lymphocyte count, granulocyte count, neutrophil count, immature neutrophil to total neutrophil ratio, platelet count, serum creatinine concentration, urea concentration, lactate concentration, base excess, $pO_2$ and $HCO_3^-$.

18. The method of claim 16 wherein the clinical measurement is according to a clinical severity model for sepsis.

19. The method of claim 18 wherein the clinical model is selected from the group consisting of the Acute Physiology and Chronic Health Evaluation, the Acute Physiology and Chronic Health Evaluation II, the Acute Physiology and Chronic Health Evaluation III, the Mortality Prediction Model, the Simplified Acute Physiology score, the Multiple Organ Dysfunction Score, the Sequential Organ Failure Assessment score, the Logistical Organ Dysfunction Score, and the predisposition, infection, response, and organ dysfunction concept.

20. A method for the diagnosis of sepsis in a SIRS-positive patient comprising the steps of:
measuring the amount of total lysophosphatidylcholine in fluid or tissue of the SIRS-positive patient;
comparing the amount of total lysophosphatidylcholine in fluid or tissue of the SIRS-positive patient to a reference amount indicative of the amount of total lysophosphatidylcholine in fluid or tissue of an individual that has sepsis; and
diagnosing sepsis in the SIRS-positive patient, based on the comparison of the amount of total lysophosphatidylcholine to the reference amount;
wherein the amount of total lysophosphatidylcholine in fluid or tissue of the SIRS-positive patient is measured about every 24 hours;
wherein the measuring, comparing and diagnosing steps are made prior to laboratory confirmation of a clinically significant infection causative of sepsis;
wherein the reference amount is a cut-off reference amount that is 60 µM lysophosphatidylcholine; and
wherein an amount less than the cut-off reference amount indicates diagnosis of sepsis.

21. A method for the diagnosis of sepsis in a SIRS-positive patient comprising the steps of:
measuring the amount of a compound according to formula (I)

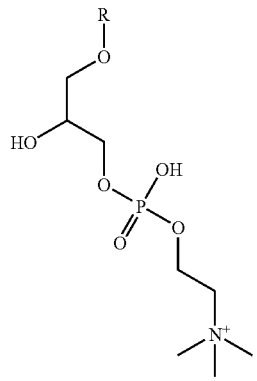

or a salt or solvate thereof, wherein R is $C_{16}$-$C_{18}$ acyl, in fluid or tissue of the SIRS-positive patient;
comparing the amount of the compound to a reference amount indicative of the amount of the compound in fluid or tissue of an individual that has sepsis; and
diagnosing sepsis in the SIRS-positive patient, based on the comparison of the amount of the compound to the reference amount;
wherein the amount of the compound in fluid or tissue of the SIRS-positive patient is measured about every 24 hours;
wherein the measuring, comparing and diagnosing steps are made prior to laboratory confirmation of a clinically significant infection causative of sepsis;
wherein the reference amount is a cut-off reference amount that is 60 µM lysophosphatidylcholine; and
wherein an amount less than the cut-off reference amount indicates diagnosis of sepsis.

22. The method of claim 20 or 21 wherein the individual is sepsis-positive.

23. The method of claim 1 or 20, wherein the step of measuring total lysophosphatidylcholine further comprises:
detecting lysophosphatidylcholine in the SIRS-positive patient by contacting a sample from fluid or tissue of the SIRS-positive patient with:
an enzyme or reagent capable of reacting lysophosphatidylcholine to form glycerophosphatidylcholine;
an enzyme or reagent capable of reacting glycerophosphatidylcholine to form choline;
an enzyme or reagent capable of reacting choline, water and oxygen to form peroxide;
a peroxidase; and
a fluorogenic substrate of said peroxidase;
under conditions suitable for formation of a fluorescent product wherein the fluorescent product indicates lysophosphatidylcholine.

24. The method of claim 23 wherein said enzyme or reagent capable of reacting lysophosphatidylcholine to form glycerophosphatidylcholine is a lysophospholipase.

25. The method of claim 23 wherein said enzyme or reagent capable of converting lysophosphatidylcholine to glycerophosphatidylcholine is EC 3.1.1.5.

26. The method of claim 23 wherein said enzyme or reagent capable of reacting glycerophosphatidylcholine to form choline is a glycerophosphatidylcholine diesterase.

27. The method of claim 23 wherein said enzyme or reagent capable of reacting glycerophosphatidylcholine to form choline is EC 3.1.4.2.

28. The method of claim 23 wherein said enzyme or reagent capable of reacting choline to form peroxide is a choline oxidase.

29. The method of claim 23 wherein said enzyme or reagent capable of reacting choline to peroxide is EC 1.1.3.17.

30. The method of claim 23 wherein said peroxidase is horseradish peroxidase.

31. The method of claim 23 wherein said fluorogenic substrate is 10-acetyl-3,7-dihydroxyphenoxazine and said fluorescent product is 7-hydroxy-3H-phenoxazin-3-one.

32. The method of claim 23 wherein said fluorescent product is detected by fluorescence detection.

33. The method of claim 23 wherein the sample is contacted with a lysophospholipase, a glycerophosphatidylcholine diesterase, a choline oxidase, a peroxidase and 10-acetyl-3,7-dihydroxyphenoxazine under conditions suitable for formation of 7-hydroxy-3H-phenoxazin-3-one wherein 7-hydroxy-3H-phenoxazin-3-one indicates lysophosphatidylcholine.

34. The method of claim 23 wherein the sample is contacted with EC 3.1.1.5, EC 3.1.4.2, EC 1.1.3.17, horseradish peroxidase and 10-acetyl-3,7-dihydroxyphenoxazine under conditions suitable for formation of 7-hydroxy-3H-phenoxazin-3-one wherein 7-hydroxy-3H-phenoxazin-3-one indicates lysophosphatidylcholine.

35. The method of claim 23 wherein the amount of fluorescent product indicates the amount of lysophosphatidylcholine.

36. A method for the diagnosis of sepsis in a SIRS-positive patient comprising the steps of:
   measuring the amount of total lysophosphatidylcholine in fluid or tissue of the SIRS-positive patient;
   comparing the amount of total lysophosphatidylcholine in fluid or tissue of the SIRS-positive patient to a reference amount indicative of the amounts of total lysophosphatidylcholine in fluids or tissues of a plurality of individuals that have sepsis; and
   diagnosing sepsis in the SIRS-positive patient, based on the comparison of the amount of total lysophosphatidylcholine to the reference amount;
   wherein the amount of total lysophosphatidylcholine in fluid or tissue of the SIRS-positive patient is measured about every 24 hours;
   wherein the measuring, comparing and diagnosing steps are made prior to laboratory confirmation of a clinically significant infection causative of sepsis;
   wherein the reference amount is a cut-off reference amount that is 60 µM lysophosphatidylcholine; and
   wherein an amount less than the cut-off reference amount indicates diagnosis of sepsis.

37. A method for the diagnosis of sepsis in a SIRS-positive patient comprising the steps of
   monitoring over time the amount of total lysophosphatidylcholine in fluid or tissue of the SIRS-positive patient; and
   diagnosing sepsis in the SIRS-positive patient, based on the monitoring of the amount of total lysophosphatidylcholine;
   wherein the monitoring and diagnosing steps are made prior to laboratory confirmation of a clinically significant infection causative of sepsis; and
   wherein a decrease in the amount of total lysophosphatidylcholine monitored over time, such that a second amount is less than 75% of a previous amount over a 24 hour interval, indicates diagnosis of sepsis.

38. A method for the diagnosis of sepsis in a SIRS-positive patient comprising the steps of:
   evaluating over time the amount of total lysophosphatidylcholine in fluid or tissue of the SIRS-positive patient; and
   diagnosing sepsis in the SIRS-positive patient, based on the evaluation of the amount of total lysophosphatidylcholine;
   wherein the evaluating and diagnosing steps are made prior to laboratory confirmation of a clinically significant infection causative of sepsis; and
   wherein a decrease in the amount of total lysophosphatidylcholine evaluated over time, such that a second amount is less than 75% of a previous amount over a 24 hour interval, indicates diagnosis of sepsis.

39. A method for the diagnosis of sepsis in a SIRS-positive patient comprising the steps of
   measuring the amount of a compound according to formula (I)

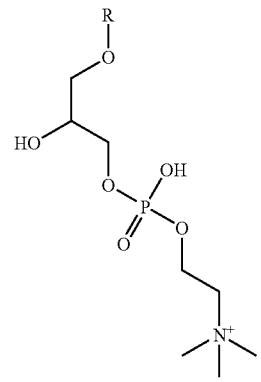

or a salt or solvate thereof, wherein R is $C_{16}$-$C_{18}$ acyl, in fluid or tissue of the SIRS-positive patient;
   comparing the amount of the compound to a reference amount indicative of the amounts of the compound in fluids or tissues of a plurality of individuals that have sepsis; and
   diagnosing sepsis in the SIRS-positive patient, based on the comparison of the amount of the compound to the reference amount;
   wherein the amount of the compound in fluid or tissue of the SIRS-positive patient is measured about every 24 hours;
   wherein the measuring, comparing and diagnosing steps are made prior to laboratory confirmation of a clinically significant infection causative of sepsis;
   wherein the reference amount is a cut-off reference amount that is 60 µM lysophosphatidylcholine; and
   wherein an amount less than the cut-off reference amount indicates diagnosis of sepsis.

40. A method for the diagnosis of sepsis in a SIRS-positive patient comprising the steps of:
   monitoring over time the amount of a compound according to formula (I)

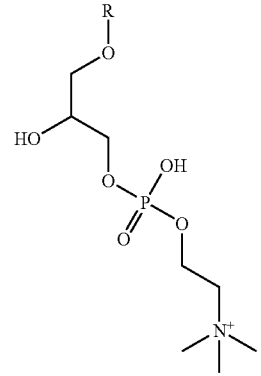

or a salt or solvate thereof, wherein R is $C_{16}$-$C_{18}$ acyl, in fluid or tissue of the SIRS-positive patient; and
   diagnosing sepsis in the SIRS-positive patient, based on the monitoring of the amount of the compound;
   wherein the monitoring and diagnosing steps are made prior to laboratory confirmation of a clinically significant infection causative of sepsis; and wherein a decrease in the amount of the compound monitored over time, such that a second amount is less than 75% of a previous amount over a 24 hour interval, indicates diagnosis of sepsis.

41. A method for the diagnosis of sepsis in a SIRS-positive patient comprising the steps of:

evaluating over time the amount of a compound according to formula (I)

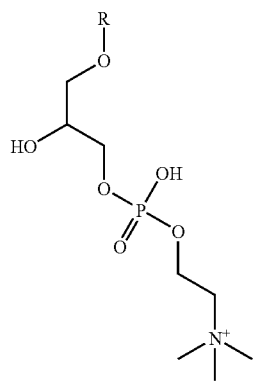

(I)

or a salt or solvate thereof, wherein R is $C_{16}$-$C_{18}$ acyl, in fluid or tissue of the SIRS-positive patient; and diagnosing sepsis in the SIRS-positive patient, based on the evaluation of the amount of the compound;

wherein the evaluating and diagnosing steps are made prior to laboratory confirmation of a clinically significant infection causative of sepsis; and wherein a decrease in the amount of the compound evaluated over time, such that a second amount is less than 75% of a previous amount over a 24 hour interval, indicates diagnosis of sepsis.

42. A method for the diagnosis of sepsis in a SIRS-positive patient comprising the steps of:

measuring over time a plurality of amounts of a compound according to formula (I)

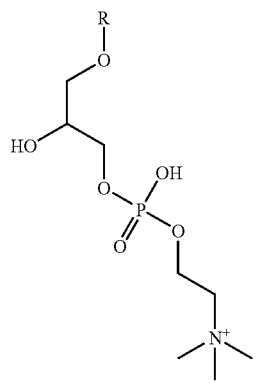

(I)

or a salt or solvate thereof, wherein R is $C_{10}$-$C_{22}$ acyl, in fluid or tissue of the SIRS-positive patient; and diagnosing sepsis in the SIRS-positive patient, based on the measurements of the plurality of amounts of the compound;

wherein the measuring and diagnosing steps are made prior to laboratory confirmation of a clinically significant infection causative of sepsis; and wherein a decrease in the plurality of amounts of the compound measured over time, such that a second amount is less than 75% of a previous amount over a 24 hour interval, indicates diagnosis of sepsis.

43. The method of claim 42 wherein R is $C_{14}$-$C_{22}$ acyl.

44. The method of claim 42 wherein R is $C_{16}$-$C_{20}$ acyl.

45. A method for the diagnosis of sepsis in a SIRS-positive patient comprising the steps of:

measuring the amount of a compound according to formula (I)

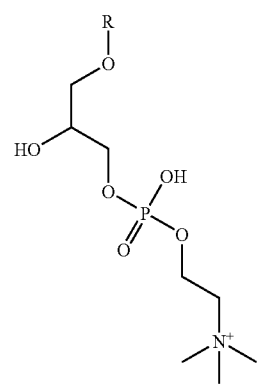

(I)

or a salt or solvate thereof, wherein R is $C_{10}$-$C_{22}$ acyl, in fluid or tissue of the SIRS-positive patient;

comparing the amount of the compound to a reference amount indicative of the amount of the compound in fluid or tissue of an individual that has sepsis; and diagnosing sepsis in the SIRS-positive patient, based on the comparison of the amount of the compound to the reference amount;

wherein the amount of the compound in fluid or tissue of the SIRS-positive patient is measured about every 24 hours;

wherein the measuring, comparing and diagnosing steps are made prior to laboratory confirmation of a clinically significant infection causative of sepsis;

wherein the reference amount is a cut-off reference amount that is 60 µM lysophosphatidylcholine; and wherein an amount less than the cut-off reference amount indicates diagnosis of sepsis.

46. The method of claim 45 wherein R is $C_{14}$-$C_{22}$ acyl.

47. The method of claim 45 wherein R is $C_{16}$-$C_{20}$ acyl.

48. A method for the diagnosis of sepsis in a SIRS-positive patient comprising the steps of:

measuring the amount of a compound according to formula (I)

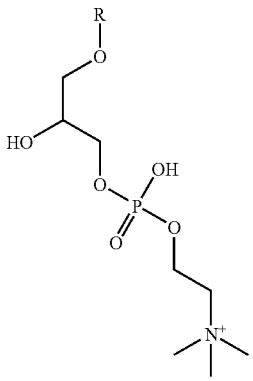

(I)

or a salt or solvate thereof, wherein R is $C_{10}$-$C_{22}$ acyl, in fluid or tissue of the SIRS-positive patient;
  comparing the amount of the compound to a reference amount indicative of the amounts of the compound in fluids or tissues of a plurality of individuals that have sepsis; and
  diagnosing sepsis in the SIRS-positive patient, based on the comparison of the amount of the compound to the reference amount;
  wherein the amount of the compound in fluid or tissue of the SIRS-positive patient is measured about every 24 hours;
  wherein the measuring, comparing and diagnosing steps are made prior to laboratory confirmation of a clinically significant infection causative of sepsis;
  wherein the reference amount is a cut-off reference amount that is 60 μM lysophosphatidylcholine; and
  wherein an amount less than the cut-off reference amount indicates diagnosis of sepsis.

49. The method of claim 48 wherein R is $C_{14}$-$C_{22}$ acyl.
50. The method of claim 48 wherein R is $C_{16}$-$C_{20}$ acyl.
51. A method for the diagnosis of sepsis in a SIRS-positive patient comprising the steps of:
  monitoring over time the amount of a compound according to formula (I)

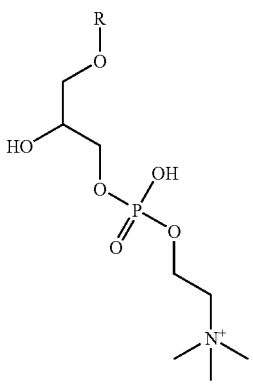

(I)

or a salt or solvate thereof, wherein R is $C_{10}$-$C_{22}$ acyl, in fluid or tissue of the SIRS-positive patient; and
  diagnosing sepsis in the SIRS-positive patient, based on the monitoring of the amount of the compound;
  wherein the monitoring and diagnosing steps are made prior to laboratory confirmation of a clinically significant infection causative of sepsis; and
  wherein a decrease in the amount of the compound monitored over time, such that a second amount is less than 75% of a previous amount over a 24 hour interval, indicates diagnosis of sepsis.

52. The method of claim 51 wherein R is $C_{14}$-$C_{22}$ acyl.
53. The method of claim 51 wherein R is $C_{16}$-$C_{20}$ acyl.
54. A method for the diagnosis of sepsis in a SIRS-positive patient comprising the steps of:
  evaluating over time the amount of a compound according to formula (I)

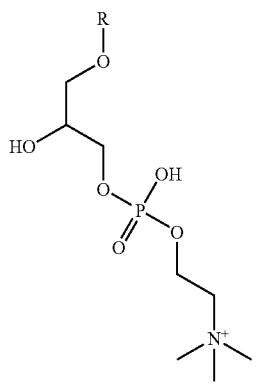

(I)

or a salt or solvate thereof, wherein R is $C_{10}$-$C_{22}$ acyl, in fluid or tissue of the SIRS-positive patient; and
  diagnosing sepsis in the SIRS-positive patient, based on the evaluation of the amount of the compound;
  wherein the evaluating and diagnosing steps are made prior to laboratory confirmation of a clinically significant infection causative of sepsis; and
  wherein a decrease in the amount of the compound evaluated over time, such that a second amount is less than 75% of a previous amount over a 24 hour interval, indicates diagnosis of sepsis.

55. The method of claim 54 wherein R is $C_{14}$-$C_{22}$ acyl.
56. The method of claim 54 wherein R is $C_{16}$-$C_{20}$ acyl.
57. A method for the diagnosis of sepsis in a SIRS-positive patient comprising the steps of:
  measuring over time a plurality of amounts of total lysophosphatidylcholine in fluid or tissue of the SIRS-positive patient;
  measuring one or more clinical measurements of the SIRS-positive patient; and
  diagnosing sepsis in the SIRS-positive patient, based on the measurements of the plurality of amounts of total lysophosphatidylcholine and the measurement of the clinical measurement(s);
  wherein the measuring and diagnosing steps are made prior to laboratory confirmation of a clinically significant infection causative of sepsis; and
  wherein a decrease in the plurality of amounts of total lysophosphatidylcholine measured over time, such that a second amount is less than 75% of a previous amount over a 24 hour interval, indicates diagnosis of sepsis.

58. The method of claim 57 wherein the one or more clinical measurement(s) are selected from the group consisting of respiratory rate, temperature, heart rate, white blood cell count, monocyte count, lymphocyte count, granulocyte count, neutrophil count, immature neutrophil to total neutrophil ratio, platelet count, serum creatinine concentration, urea concentration, lactate concentration, base excess, $pO_2$ and $HCO_3^-$ concentration.

59. The method of claim 57 wherein one clinical measurement is measured.

60. The method of claim 59 wherein respiratory rate is measured.

61. The method of claim 59 wherein temperature is measured.

62. The method of claim 57 wherein more than one clinical measurement is measured.

63. The method of claim 62 wherein respiratory rate and temperature are measured.

64. The method of claim 57 further comprising measuring one or more biomarkers in fluid or tissue of the SIRS-positive patient, wherein the biomarkers are selected from the group consisting of endotoxin, bacterial DNA, protein C, procalcitonin, LBP-LPS-binding protein, fibrin degrading products, antithrombin III, dimer D, HLA-DR, CD-64, E-selectin, cortisol, ACTH, CD-14, sTNF-RI, sTNF-RII, TNF, IL-6, IL-8 and IL-10, D-dimer, prothrombin time, activated partial thromboplastin time, plasminogen activator inhibitor-1, soluble thrombomodulin, thrombin activatable fibrinolysis inhibitor, protein S, antithrombin and TNF-α.

65. A method for the diagnosis of sepsis in a SIRS-positive patient comprising the steps of:
measuring over time a plurality of amounts of a compound according to formula (I)

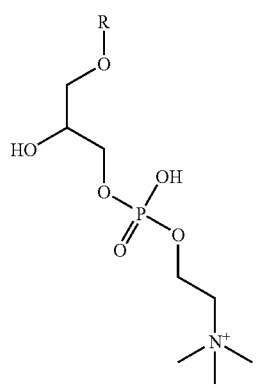

or a salt or solvate thereof, wherein R is $C_{10}$-$C_{22}$ acyl, in fluid or tissue of the SIRS-positive patient;
measuring one or more clinical measurements of the SIRS-positive patient; and
diagnosing sepsis in the SIRS-positive patient, based on the measurements of the plurality of amounts of the compound and the measurement of the clinical measurement(s);
wherein the measuring and diagnosing steps are made prior to laboratory confirmation of a clinically significant infection causative of sepsis; and
wherein decrease in the plurality of amounts of the compound measured over time, such that a second amount is less than 75% of a previous amount over a 24 hour interval, indicates diagnosis of sepsis.

66. The method of claim 65 wherein the clinical measurement(s) are selected from the group consisting of respiratory rate, temperature, heart rate, white blood cell count, monocyte count, lymphocyte count, granulocyte count, neutrophil count, immature neutrophil to total neutrophil ratio, platelet count, serum creatinine concentration, urea concentration, lactate concentration, base excess, $pO_2$ and $HCO_3^-$ concentration.

67. The method of claim 65 wherein one clinical measurement is measured.

68. The method of claim 67 wherein respiratory rate is measured.

69. The method of claim 67 wherein temperature is measured.

70. The method of claim 65 wherein more than one clinical measurement is measured.

71. The method of claim 70 wherein respiratory rate and temperature are measured.

72. The method of claim 65 further comprising measuring one or more biomarkers in fluid or tissue of the SIRS-positive patient, wherein the biomarkers are selected from the group consisting of endotoxin, bacterial DNA, protein C, procalcitonin, LBP-LPS-binding protein, fibrin degrading products, antithrombin III, dimer D, HLA-DR, CD-64, E-selectin, cortisol, ACTH, CD-14, sTNF-RI, sTNF-RII, TNF, IL-6, IL-8 and IL-10, D-dimer, prothrombin time, activated partial thromboplastin time, plasminogen activator inhibitor-1, soluble thrombomodulin, thrombin activatable fibrinolysis inhibitor, protein S, antithrombin and TNF-α.

73. The method of claim 59 or claim 65 wherein the amount is measured by spectrometry, chromatography, immunoassay, electrophoresis or enzymatic assay.

74. The method of claim 57 or claim 65 wherein the fluid or tissue is blood, plasma, saliva, serum, sputum, urine, cells, cellular extract or tissue biopsy.

75. A method for the diagnosis of sepsis in a SIRS-positive patient comprising the steps of:
monitoring or evaluating over time the amount of total lysophosphatidylcholine in fluid or tissue of the SIRS-positive patient;
monitoring or evaluating one or more clinical measurements of the SIRS-positive patient; and
diagnosing sepsis in the SIRS-positive patient, based on the monitoring or evaluation of the amount of total lysophosphatidylcholine and the monitoring or evaluation of the clinical measurement(s);
wherein the monitoring or evaluating and diagnosing steps are made prior to laboratory confirmation of a clinically significant infection causative of sepsis; and
wherein a decrease in the amount of total lysophosphatidylcholine monitored or evaluated over time, such that a second amount is less than 75% of a previous amount over a 24 hour interval, indicates diagnosis of sepsis.

76. The method of claim 75 wherein the clinical measurement(s) are selected from the group consisting of respiratory rate, temperature, heart rate, white blood cell count, monocyte count, lymphocyte count, granulocyte count, neutrophil count, immature neutrophil to total neutrophil ratio, platelet count, serum creatinine concentration, urea concentration, lactate concentration, base excess, $pO_2$ and $HCO_3^-$ concentration.

77. The method of claim 75 wherein one clinical measurement is monitored or evaluated.

78. The method of claim 77 wherein respiratory rate is monitored or evaluated.

79. The method of claim 77 wherein temperature is monitored or evaluated.

80. The method of claim 75 wherein more than one clinical measurement is monitored or evaluated.

81. The method of claim 80 wherein respiratory rate and temperature are monitored or evaluated.

82. The method of claim 75 further comprising monitoring or evaluating one or more biomarkers in fluid or tissue of the SIRS-positive patient, wherein the biomarkers are selected from the group consisting of endotoxin, bacterial DNA, protein C, procalcitonin, LBP-LPS-binding protein, fibrin degrading products, antithrombin III, dimer D, HLA-DR, CD-64, E-selectin, cortisol, ACTH, CD-14, sTNF-RI, sTNF-RII, TNF, IL-6, IL-8 and IL-10, D-dimer, prothrombin time, activated partial thromboplastin time, plasminogen activator inhibitor-1, soluble thrombomodulin, thrombin activatable fibrinolysis inhibitor, protein S, antithrombin and TNF-α.

83. A method for the diagnosis of sepsis in a SIRS-positive patient comprising the steps of:
monitoring or evaluating over time the amount of a compound according to formula (I)

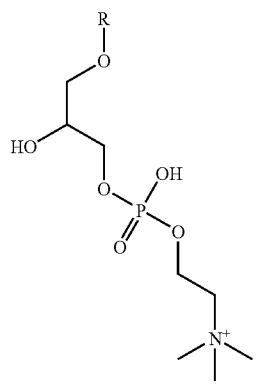

(I)

or a salt or solvate thereof, wherein R is $C_{10}$-$C_{22}$ acyl, in fluid or tissue of the SIRS-positive patient;
monitoring or evaluating one or more clinical measurements of the SIRS-positive patient; and
diagnosing sepsis in the SIRS-positive patient, based on the monitoring or evaluation of the amount of the compound and the monitoring or evaluation of the clinical measurement(s);
wherein the monitoring and evaluating and diagnosing steps are made prior to laboratory confirmation of a clinically significant infection causative of sepsis; and
wherein a decrease in the amount of the compound monitored or evaluated over time, such that a second amount is less than 75% of a previous amount over a 24 hour interval, indicates diagnosis or of sepsis.

84. The method of claim 83 wherein the clinical measurement(s) are selected from the group consisting of respiratory rate, temperature, heart rate, white blood cell count, monocyte count, lymphocyte count, granulocyte count, neutrophil count, immature neutrophil to total neutrophil ratio, platelet count, serum creatinine concentration, urea concentration, lactate concentration, base excess, $pO_2$ and $HCO_3^-$ concentration.

85. The method of claim 83 wherein one clinical measurement is monitored or evaluated.

86. The method of claim 85 wherein respiratory rate is monitored or evaluated.

87. The method of claim 85 wherein temperature is monitored or evaluated.

88. The method of claim 83 wherein more than one clinical measurement is monitored or evaluated.

89. The method of claim 88 wherein respiratory rate and temperature are monitored evaluated.

90. The method of claim 83 further comprising monitoring or evaluating one or more biomarkers in fluid or tissue of the SIRS-positive patient, wherein the biomarkers are selected from the group consisting of endotoxin, bacterial DNA, protein C, procalcitonin, LBP-LPS-binding protein, fibrin degrading products, antithrombin III, dimer D, HLA-DR, CD-64, E-selectin, cortisol, ACTH, CD-14, sTNF-RI, sTNF-RII, TNF, IL-6, IL-8 and IL-10, D-dimer, prothrombin time, activated partial thromboplastin time, plasminogen activator inhibitor-1, soluble thrombomodulin, thrombin activatable fibrinolysis inhibitor, protein S, antithrombin and TNF-α.

91. The method of claim 1 wherein the measurements of the plurality of amounts of total lysophosphatidylcholine are made every 2 hours, 3 hours, 4 hours, 6 hours, 8 hours, 12 hours, or 24 hours prior to laboratory confirmation of a clinically significant infection causative of sepsis.

92. The method of claim 6 wherein the measurements of the plurality of amounts of the compound are made every 2 hours, 3 hours, 4 hours, 6 hours, 8 hours, 12 hours, or 24 hours prior to laboratory confirmation of a clinically significant infection causative of sepsis.

93. The method of claim 1 wherein the measurements of the plurality of amounts of total lysophosphatidylcholine are made every 1 to 8 hours, 8 to 12 hours, 12 to 16 hours, or 16 to 24 hours after the SIRS-positive patient arrives in an intensive care unit.

94. The method of claim 6 wherein the measurements of the plurality of amounts of the compound are made every 1 to 8 hours, 8 to 12 hours, 12 to 16 hours, or 16 to 24 hours after the SIRS-positive patient arrives in an intensive care unit.

95. The method of claim 1, wherein a decrease in the plurality of amounts of total lysophosphatidylcholine measured 24 hours prior to laboratory confirmation of a clinically significant infection causative of sepsis indicates diagnosis of sepsis.

96. The method of claim 1 or 20, wherein a positive culture result for an organism in the fluid or tissue of the SIRS-positive patient is laboratory confirmation of a clinically significant infection causative of sepsis.

* * * * *